United States Patent [19]

Evers et al.

[11] 4,045,491

[45] Aug. 30, 1977

[54] α-OXY(OXO) SULFIDES AND ETHERS
[75] Inventors: William J. Evers, Red Bank; Howard H. Heinsohn, Jr., Hazlet, both of N.J.
[73] Assignee: International Flavors & Fragrances Inc., New York, N.Y.
[21] Appl. No.: 730,538
[22] Filed: Oct. 7, 1976
[51] Int. Cl.$^2$ .......................................... C07C 49/175
[52] U.S. Cl. ............................... 260/594; 260/590 D; 260/488 CD; 260/488 F; 260/611 R; 260/609 R; 260/455 R; 260/481 R; 260/593 R; 426/650; 252/522; 252/89 R; 252/108; 424/65; 424/59; 424/70; 424/76
[58] Field of Search ........................... 260/593 R, 594
[56] References Cited

U.S. PATENT DOCUMENTS

| 3,773,524 | 11/1973 | Katz et al. | 260/593 R |
| 3,819,712 | 6/1974 | Lamparsky et al. | 260/593 R |
| 3,946,080 | 3/1976 | Demole | 260/593 R |

Primary Examiner—James O. Thomas, Jr.
Assistant Examiner—James H. Reamer
Attorney, Agent, or Firm—Arthur L. Liberman; Franklin D. Wolffe

[57] ABSTRACT

Described are α-oxy(oxo) sulfides and ethers having the generic structure:

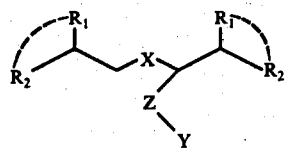

wherein X is one of:

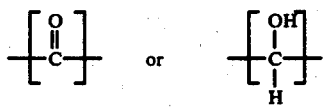

Z is one of sulfur or oxygen; when $R_1$ and $R_2$ are taken separately, $R_1$ is hydrogen or methyl, and $R_2$ is methyl; and when $R_1$ and $R_2$ are taken together, $R_1$ and $R_2$ form phenyl moieties; and Y is one of $C_1$-$C_4$ alkyl, $C_3$ or $C_4$ alkenyl, acetyl, methoxycarbonylmethyl, or 1,3-diethylacetonyl.

Addition of one or more α-oxy(oxo) sulfides and ethers to foodstuff flavorings or foodstuffs is indicated to produce the following aroma and flavor characteristics, in the alternative or taken together:

Aroma

Green/spicey, Sweet, Fruity, Fresh/fruity, Gooseberry, Concord grape, Grape, Almond, Nutty, Cereal-like, Lachrymatory onion-like, Oniony, Green onion-like, Leek, Broccoli-like, Grapefruit, Celery stalk-like, Floral, Rosey, Woody, Blackcurrant, Buchu leaf oil-like, Citronellal-like, Neroli-like, Bergamot-like, Violet leaves-like, Jasmin-like, Melony, Cucumber-like, Green, Vegetable, Sweet/floral.

Flavor

Spicey, Sweet, Fruity, Milk caramel-like (dulce de leche-like), Gooseberry, Broccoli-like, Nutty, Cereal-like, Oniony, Grape, Concord grape, Citrusy, Grapefruit-like, Green fruit-like, Mandarin-like, Petitgrain-like, Blackcurrant, Minty, Astringent, Coriander-like, Green, Piney, Citronellal-like, Violet leaves-like, Melony, Green fruit-like, Cucumber, Green, Floral, Floral/green, Vegetable, Garlic with lasting mouthfeel and with, in many cases, an oniony aftertaste. The compounds of our invention are useful in augmenting or enhancing the flavor and aroma nuances of berry flavors, cereal-like flavors, nut flavors, broccoli flavors, onion flavors, citrus flavors (including neroli, bergamot, lime), jasmin flavors, grapefruit flavors, concord grape flavors, blackcurrant flavors, milk caramel flavors (e.g., dulce de leche-like flavors), vegetable flavors, cucumber flavors, celery flavors and spice flavors.

Addition of a number of these α-oxy(oxo) sulfides and ethers in perfumes, colognes or perfumed articles imparts thereto sweet, green, floral, herbal, vegetative, basil-like, minty, melony, grapefruit, fruity and alliaceous aromas with yara, neroli and/or verdima-like nuances.

9 Claims, 38 Drawing Figures

NMR SPECTRUM FOR EXAMPLE I-B

SOLVENT: CDCL$_3$
SWEEP WIDTH: 2000Hz

IR SPECTRUM FOR EXAMPLE I-B

NMR SPECTRUM FOR EXAMPLE I-C

IR SPECTRUM FOR EXAMPLE I(C)

NMR SPECTRUM FOR EXAMPLE I(D)

IR SPECTRUM FOR EXAMPLE I(D)

NMR SPECTRUM FOR EXAMPLE II(C)

SOLVENT: CDCL₃
SWEEP WIDTH: 1500 Hz.

I R SPECTRUM FOR EXAMPLE II(C)

IR SPECTRUM FOR EXAMPLE II(D)

NMR SPECTRUM FOR EXAMPLE II(E)

SOLVENT: $CDCL_3$
SWEEP WIDTH: 2000 Hz.

IR SPECTRUM FOR EXAMPLE II(E)

NMR SPECTRUM FOR EXAMPLE II(F)

IR SPECTRUM FOR EXAMPLE II(F)

IR SPECTRUM IIG

NMR SPECTRUM FOR EXAMPLE II(G)

SOLVENT: $CDCL_3$
SWEEP WIDTH: 1500 Hz.

IR SPECTRUM FOR EXAMPLE II(G)

NMR SPECTRUM FOR EXAMPLE II(I)

IR SPECTRUM FOR EXAMPLE II(I)

NMR SPECTRUM FOR EXAMPLE III (A)

IR SPECTRUM FOR EXAMPLE III (A)

NMR SPECTRUM FOR EXAMPLE III(B)

IR SPECTRUM FOR EXAMPLE III(B)

NMR SPECTRUM FOR EXAMPLE IV

SOLVENT: CDCl₃
SWEEP WIDTH: 2000 Hz.

IR SPECTRUM FOR EXAMPLE IV

N M R SPECTRUM FOR EXAMPLE V(B)

I R SPECTRUM FOR EXAMPLE V(B)

NMR SPECTRUM FOR EXAMPLE VI(A)

IR SPECTRUM FOR EXAMPLE VI(A)

NMR SPECTRUM FOR EXAMPLE VI(B)

IR SPECTRUM FOR EXAMPLE VI(B)

NMR SPECTRUM FOR EXAMPLE VII

SOLVENT: CDCL$_3$
SWEEP WIDTH: 2000 Hz

IR SPECTRUM FOR EXAMPLE VII

NMR SPECTRUM FOR EXAMPLE XXII(A)

IR SPECTRUM FOR EXAMPLE XXII(A)

NMR SPECTRUM FOR EXAMPLE XXIII

IR SPECTRUM FOR EXAMPLE XXIII

α-OXY(OXO) SULFIDES AND ETHERS

BACKGROUND OF THE INVENTION

The present invention relates to α-oxy(oxo) sulfides and ethers.

There has been considerable work performed related to substances to (or in) various consumable materials including foodstuffs. These substances are used to diminish the use of natural materials, some of which may be in short supply and to provide more uniform properties in the finished product. The following flavor and aroma notes are desirable, particularly in berry fruit flavored foodstuffs, vegetable flavored foodstuffs, spicey foodstuffs and citrus fruit flavored foodstuffs:

Aroma

Green/spicey,
Sweet,
Fruity,
Fresh/fruity,
Gooseberry,
Concord grape,
Grape,
Almond,
Nutty,
Cereal-like,
Lachrymatory onion-like,
Oniony,
Green onion-like,
Leek,
Broccoli-like,
Grapefruit,
Celery stalk-like,
Floral,
Rosey,
Woody,
Blackcurrant,
Buchu leaf oil-like,
Citronellal-like,
Neroli-like,
Burgamot-like,
Violet leaves-like,
Jasmin-like,
Melony,
Cucumber-like,
Green,
Vegetable,
Sweet/floral.

Flavor

Spicey,
Sweet,
Fruity,
Milk caramel-like (dulce de leche-like),
Gooseberry,
Broccoli-like,
Nutty,
Cereal-like,
Oniony,
Grape,
Concord grape,
Citrusy,
Grapefruit-like,
Green fruit-like,
Mandarin-like,
Petitgrain-like,
Blackcurrant,
Minty,
Astringent,
Coriander-like,
Green,
Piney,
Citronellal-like,
Violet leaves-like,
Melony,
Green fruit-like,
Cucumber,
Green,
Floral,
Floral/green,
Vegetable,
Garlic.

Furthermore there is a continuing search for materials having desirable fragrance properties. Such materials are sought either to replace costly natural materials or to provide new fragrances or perfume types which have not heretofore been available. Especially desirable qualities for substances having interesting hyacinth fragrances, or narcisse fragrances, or violet fragrances, or oriental vetivert fragrances, or otto of rose fragrances are stability and persistence, particularly in a wide variety of perfumed articles (e.g., soaps, detergents and powders), perfume compositions and colognes, ease of manufacture and intensity of aroma.

Prior to this last decade it was the general opinion among those skilled in the art that compounds containing the mercapto or -SH moiety or substituted mercapto or -SR moiety (where R is an organic group such as alkyl or acetyl) were desirable for use in conjunction with foodstuff flavors only where alliaceous flavors were concerned, or where meaty flavors were concerned or where coffee-type flavors were concerned, and were not desirable for use in conjunction with other more delicate type flavors, e.g., blackcurrant, citrus and vegetable. However, within the last decade certain mercapto compounds have been ascertained to be useful, for example, in blackcurrant and buchu leaf oil-like flavors. In addition, within the last decade such compounds have been ascertained to be highly useful in perfumery also.

Thus, for example, British Pat. Nos. 1,423,914 and 1,423,915 issued on Feb. 4, 1976, teach that certain mercapto derivatives which are aliphatic or cycloaliphatic compounds having the formula:

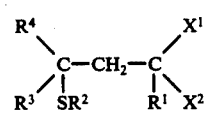

wherein $X^1$ represents a hydroxyl group or an acyl-oxy group, and $X^2$ represents a hydrogen atom; $R^1$, $R^2$, $R^3$ and $R^4$ may be the same or different and each represents a hydrogen atom or a univalent aliphatic hydrocarbyl group; or $R^1$ and $R^3$ or $R^4$, together with the intervening carbon atoms, constitute a cycloaliphatic ring, are useful as perfuming agents as exemplified by adding 3-methylthio-hexanol to a perfume base composition of the Fleuri type wherein the 3-methylthio-hexanol is said to give rise to a green, fruity aroma reminiscent of that of rhubarb.

Furthermore, for example, Canadian Pat. No. 983,050 issued on Feb. 3, 1976, teaches that 3,7-dimethyl-octa-2,6-dienyl-mercaptan (thiogeraniol) of the formula:

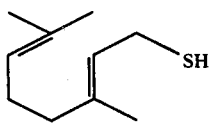

is used in making up a "synthetic buchu leaf oil" and imparts to a lavender type composition a greener and more herbal fragrance. U.S.S.R. Pat. No. 345,677 teaches that para-menthane-8-thiol-3-one is useful as a synthetic flack currant flavoring for foodstuffs. This compound has the structure:

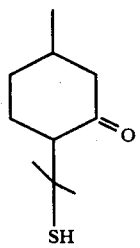

German Offenlegungschrift Pat. No. 2,316,456, published on Oct. 11, 1973 discloses the use of certain thio alcohols or their corresponding esters in perfumery and in perfumed articles, such as detergents, cosmetics and waxes. Such mercapto alcohols having the generic structure:

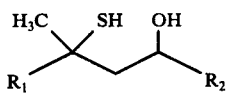

wherein $R_1$ is a hydrocarbon moiety having from 1 up to 7 carbon atoms and $R_2$ is one of hydrogen, methyl or ethyl.

U.S. Pat. Nos. 3,950,429 issued on Apr. 13, 1976, and 3,952,062 issued on Apr. 20, 1976, disclose certain alkylthiosubstituted oxo-terpenoids having 10 carbon atoms in the terpenoid skeleton as useful in perfumery and in flavors, particularly for providing vegetable notes. The generic structure of the compounds is as follows:

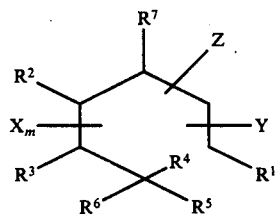

wherein
$R^1$ represents hydrogen or together with $R^4$ represents a C—C bond,
$R^2$ represents hydrogen or together with $R^6$ represents a dimethylmethylene group, or, when $R^6$ is isopropyl, together with $R^5$ represents a C—C bond,
$R^3$ represents hydrogen or together with $R^6$ represents a dimethylmethylene group,
$R^4$ represents hydrogen or together with $R^1$ represents a C—C bond,
$R^5$ represents hydrogen or, when $R^6$ signifies isopropyl, together with $R^2$ represents a C—C bond,
$R^6$ represents isopropyl or together with $R^2$ or with $R^3$ represents a dimethylmethylene group,
$R^7$ represents methyl,
X represents a C—C double bond taking the place of a C—C single bond,
$m$ = 0 to 2,
Y represents oxo bound to a primary or secondary C-atom and Z represents mercapto or lower alkylthio located in the $\beta$-position to the carbonyl function, provided that when $R^2$, $R^3$ and $R^5$ represent hydrogen, $R^6$ represents isopropyl, $R^4$ together with $R^1$ represents a C—C bond, Y is $\beta$ to the carbon atom bearing the substituent $R^7$, $m=0$, Z is $\alpha$ to the carbon atom bearing the substituent $R^5$ and $\beta$ to the carbon atom bearing the substituent $R^3$, then Z represents alkylthio.

However, none of the disclosure of the prior art contains a teaching to the effect that compounds having the generic structure:

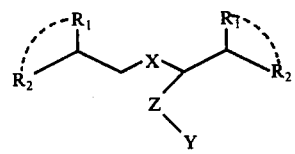

wherein X is one of:

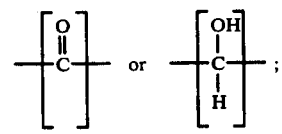

Z is one of sulfur or oxygen; when $R_1$ and $R_2$ are taken separately, $R_1$ is hydrogen or methyl, and $R_2$ is methyl; and when $R_1$ and $R_2$ are taken together, $R_1$ and $R_2$ form phenyl moieties; and Y is one of $C_1$-$C_4$ alkyl, $C_3$ or $C_4$ alkenyl, acetyl, methoxycarbonylmethyl, or 1,3-diethylacetonyl have the ability to create the following aroma and flavor notes in foodstuffs:

Aroma

Green/spicey,
Sweet,
Fruity,
Fresh/fruity,
Gooseberry,
Concord grape,
Grape,
Almond,
Nutty,
Cereal-like,
Lachrymatory onion-like,
Oniony,
Green onion-like,
Leek,
Broccoli-like,
Grapefruit,
Celery stalk-like,
Floral,
Rosey,
Woody,
Blackcurrant,
Buchu leaf oil-like,
Citronellal-like, Neroli-like,
Bergamot-like,
Violet leaves-like,
Jasmin-like,
Melony,
Cucumber-like,
Green,
Vegetable,
Sweet/floral.

Flavor

Spicey,
Sweet,
Fruity,
Milk caramel-like (dulce de leche-like),
Gooseberry,
Broccoli-like,
Nutty,
Cereal-like,
Oniony,
Grape,
Concord grape,
Citrusy,
Grapefruit-like,
Green fruit-like,
Mandarin-like,
Petitgrain-like,
Blackcurrant,
Minty,
Astringent,
Coriander-like,
Green,
Piney,
Citronellal-like,
Violet leaves-like,
Melony,
Green fruit-like,
Cucumber,
Green,
Floral,
Floral-green,
Vegetable,
Garlic.

Furthermore, other substituted mercaptans in the prior art which are shown to be useful in perfumery are indicated to have rhubarb-like, or berry, or other floral-type fragrances, e.g., ionone and irone derivatives having the structure:

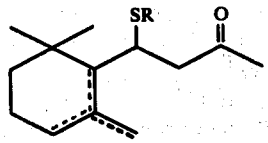

Furthermore, certain α-mercaptoketones disclosed in the prior art, but only in meat flavors. Thus, U.S. Pat. No. 3,773,524 issued on Nov. 20, 1973, discloses the use of α-ketothiols of the formula:

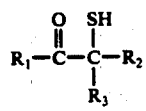

wherein $R_1$ is methyl or ethyl; and $R_2$ and $R_3$ are hydrogen, methyl or ethyl to alter the meat flavor and aroma of foodstuffs. U.S. Pat. NO. 3,892,878, issued on July 1, 1975, discloses the use of certain hydroxy-mercaptoalkanes to alter the flavor of foodstuffs, for example, 2-mercapto-3-butanol used in meat flavors. The genus disclosed by U.S. Pat. No. 3,892,878 is as follows:

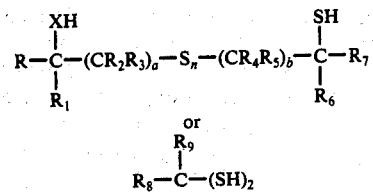

wherein X is oxygen or sulfur, $n$ is 0 or 1, $R_1$-$R_7$ are the same or different and each is hydrogen or lower alkyl of 1-4 carbon atoms, $a$ and $b$ are the same or different and each represents an integer of from 0 to 10 when $n$ is 0 and when $n$ is 1, $a$ and $b$ are the same or different and each represents an integer of from 1 to 10. 3-mercaptoheptanon-4 is disclosed per se in U.S. Pat. No. 2,888,487, issued on May 26, 1959. 3-mercapto-2,6-dimethyl-heptan-4-one is disclosed in Chem. Abstracts 6478 (d) Vol. 62, 1965 (abstract of Asinger, Diem and Schaefer, Monatsh, Chem. 95 (4-5), 1335-54 (1964). Beilstein E-IV-1 discloses 2-mercapto-2,4-dimethyl-pentan-3-on page 4039, 1-mercapto-octan-2-on at page 4040; and 1-mercapto-nonan-2-on at page 4052 and 1-mercapto-undecan-2-on at page 4060.

U.S. Pat. No. 3,922,366 issued on Nov. 25, 1975, discloses the enhancement of foodstuffs by addition of a small but effective flavor modifying amount of a compound of the general formula:

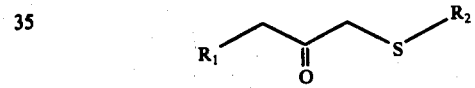

wherein $R_1$ is hydrogen or alkyl and $R_2$ is alkyl or furfuryl. The flavor nuances which are enhanced or altered are those which are found in coffee flavors and aromas.

Furthermore, none of the disclosure of the prior art contains a teaching to the effect that compounds having the generic structure:

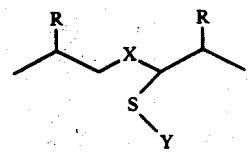

wherein R is one of methyl or hydrogen; X is one of

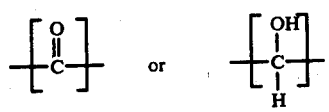

and Y is one of methyl, methallyl having the structure:

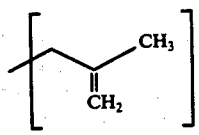

n-propyl, 2-methyl-1-propyl or acetyl, has the ability to create an intense sweet and/or green and/or floral and/or herbal and/or vegetative and/or basil-like and/or minty and/or melony and/or grapefruit and/or fruity and/or alliaceaus aroma with yara and/or neroli and/or verdima nuances as is carried out using the instant invention. Furthermore, other substituted mercaptans in the prior art which are shown to be useful in perfumery and other mercaptans in the prior art which are shown to be useful in perfumery are indicated to have rhubarb-like or berry or other type floral fragrances, e.g., ionone and irone derrivatives having the structure:

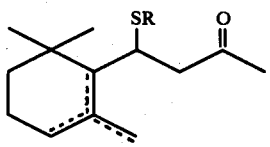

as disclosed in British Pat. No. 1,327,320, published on Aug. 22, 1973, wherein one of the dashed lines represents a double bond, and where R is hydrogen or alkyl.

THE INVENTION

The invention comprises one or more compounds having the structure:

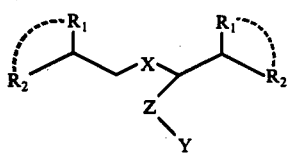

wherein X is one of:

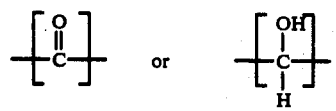

Z is one of sulfur or oxygen; when $R_1$ and $R_2$ are taken separately, $R_1$ is hydrogen or methyl, and $R_2$ is methyl; and when $R_1$ and $R_2$ are taken together, $R_1$ and $R_2$ form phenyl moieties; and Y is one of $C_1$–$C_4$ alkyl, $C_3$ or $C_4$ alkenyl, acetyl, methoxycarbonylmethyl, or 1,3-diethylacetonyl the specific embodiments of which are described hereinafter by way of example and in accordance with which it is now preferred to practice the invention.

Such α-oxy(oxo) sulfides and ethers are obtained by reacting an alkanone with $SO_2Cl_2$ to form an α-chloroketone; reacting the α-chloroketone with either an alkali metal mercaptide or an alkali metal alkoxide (depending on whether Z is sulfur or oxygen) to form either an α-oxo sulfide or an α-oxo ether which can be used for its food flavor properties; or, if desired, reacting the resulting α-oxo sulfide or α-oxo ether with a reducing agent such as an alkali metal borohydride in order to obtain an α-oxy sulfide or an α-oxy ether. Thus, the aforementioned reaction sequence is illustrated as follows:

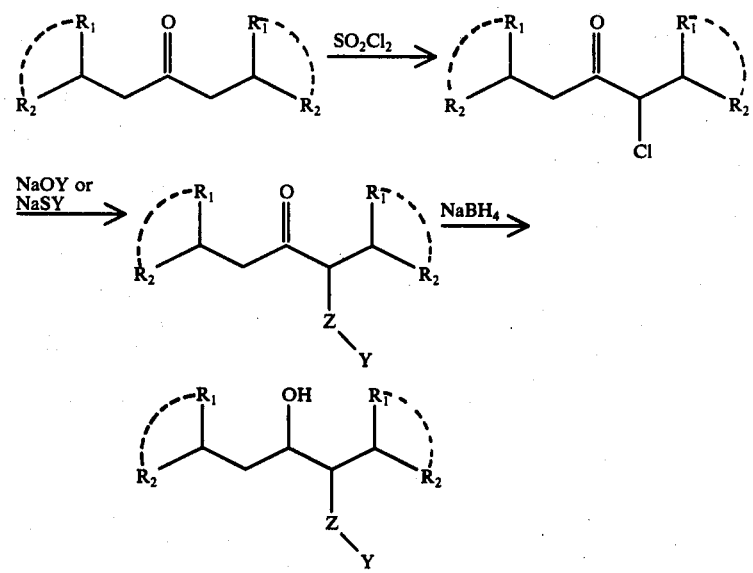

wherein X is one of:

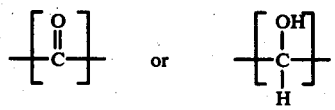

Z is one of sulfur or oxygen; when $R_1$ and $R_2$ are taken separately, $R_1$ is hydrogen or methyl, and $R_2$ is methyl; and when $R_1$ and $R_2$ are taken together, $R_1$ and $R_2$ form phenyl moieties; and Y is one of $C_1$–$C_4$ alkyl, $C_3$ or $C_4$ alkenyl, acetyl, methoxycarbonylmethyl, or 1,3-diethylacetonyl.

The reaction between the $SO_2Cl_2$ and the ketone preferably takes place in the absence of a solvent at a temperature of between 15° C and 40° C. The $SO_2Cl_2$ is preferably added to the ketone. At the end of the reaction, the reaction mass is worked up, the chlorinated ketone being distilled in vacuo.

The resulting chlorinated ketone is then reacted with either an alkali metal mercaptide or an alkali metal alkoxide. Preferably the alkali metal mercaptide is sodium mercaptide, preferably which is prepared by reaction of sodium methylate with an appropriate mercaptan in methanol. Preferably the alkali metal alkoxide is sodium methoxide. The chlorinated ketone is preferably

TABLE II

| COMPOUND | STRUCTURE | AROMA |
| --- | --- | --- |
| 3-methylthio-4-heptanol | 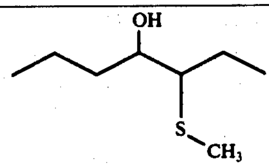 | At 1% in food grade ethanol, a sweet, green, floral, herbal, vetetative note. |
| 3-methylthio-4-heptanone | 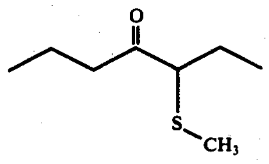 | At 1% in food grade ethanol a green, minty, herbaceous note with vegetative basil notes. |
| 3-propylthio-4-heptanol | 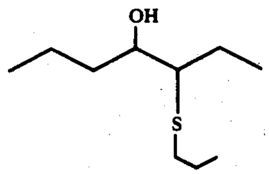 | Fatty, cucumber, onion (scallion, shallot) aroma with some green melon and floral nuances. |
| 3-thioacetyl-2,6-dimethyl-4-heptanone | 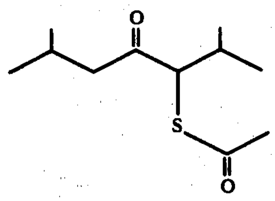 | At 1% in food grade ethanol, a sweet, meaty, vegetable aroma with somewhat of a grapefruit topnote. |
| 3-isobutylthio-4-heptanone | 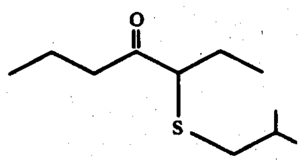 | Evaluated at 1% in food grade ethanol, a meaty onion aroma with a green, spicey and peppery nuance and an underlying bergamot note. |
| 3-isobutylthio-2,6-dimethyl-4-heptanol | 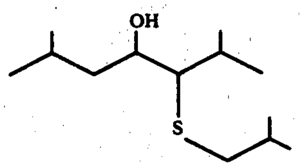 | Evaluated at 1% in food grade ethanol, a vetetable, green, horseradish, somewhat rubbery, onion-like aroma contaig notes of hyacinth and narcisse. |
| 3-methylthio-2,6-dimethyl-4-heptanone | 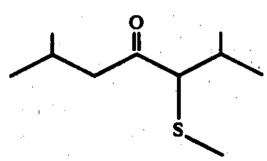 | Evaluated at 1% in food grade ethanol, a sweet, sulfurous, slightly floral and woody aroma with a fruity and berry nuance. |
| 3-(methallylthio)-2,6-dimethyl-4-heptanone | 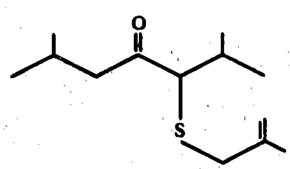 | At 1% in ethanol, a fruity, grapefruit, somewhat floral aroma with underlying yara neroli notes and bready, vegetative nuances. |

One or more of the aforementioned α-oxy(oxo) sulfides having the structure:

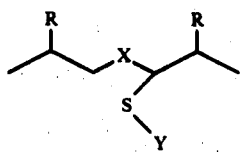

wherein X is one of:

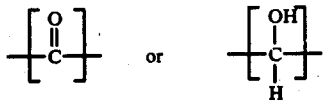

R is one of methyl or hydrogen, and Y is one of methyl, methallyl, acetyl, 1-propyl or 2-methyl-1-propyl is an olfactory agent and can be incorporated into a wide variety of compositions each of which will be enhanced or augmented by its sweet, green, floral, herbal, vegetative, basil-like, minty, melony, grapefruit, fruity and/or aliaceous notes and/or yara, neroli and/or verdima nuances.

The α-oxy(oxo) sulfides or mixture of α-oxy(oxo) sulfides can be added to perfume compositions as pure compounds or can be added to mixtures of materials in fragrance-imparting compositions to provide a desired fragrance character to a finished perfume material. The perfume and fragrance compositions obtained according to this invention are suitable in a wide variety of perfumed articles and can also be used to enhance, modify or reinforce natural fragrance materials. It will thus be appreciated that the α-oxy(oxo) sulfides of our invention is (are) useful as olfactory agent(s) and fragrance(s).

The term "perfume composition" is used herein to mean a mixture of compounds, including, for example, natural oils, synthetic oils, alcohols, aldehydes, ketones, esters, lactones, nitriles and frequently hydrocarbons which are admixed so that the combined odors of the individual components produce a pleasant or desired fragrance. Such perfume compositions usually contain (a) the main note or the bouquet or foundation-stone of the composition; (b) modifiers which round-off and accompany the main note; (c) fixatives which include odorous substances which lend a particular note to the perfume throughout all stages of evaporation, and substances which retard evaporation and (d) top-notes which are usually low-boiling, fresh-smelling materials. Such perfume compositions of our invention can be used in conjunction with carriers, vehicles, solvents, dispersants, emulsifiers, surface-active agents, aerosol propellants, and the like.

In perfume compositions the individual components contribute their particular olfactory characteristics, but the overall effect of the perfume composition will be the sum of the effect of each ingredient. Thus, one or more of the α-oxy(oxo) sulfides or our invention can be used to alter, augment, modify or enhance the aroma characteristics of a perfume composition or a perfumed article, for example, by highlighting or moderating the olfactory reaction contributed by another ingredient of the composition.

The amount of one or more of the α-oxy(oxo) sulfides of our invention which will be effective in perfume compositions depends upon many factors, including the other ingredients, their amounts and the effects which are desired. It has been found that perfume compositions containing as much as 2% or as litle as 0.005% by weight of the mixtures or compounds of this invention, or even less can be used to impart a buchu leaf oil-like aroma or a grapefruit oil-like aroma to soaps, cosmetics and other products. The amount employed will depend upon considerations of cost, nature of the end products, the effect desired in the finished product, and the particular fragrance sought.

One or more of the α-oxy(oxo) sulfides of our invention as disclosed herein can be used alone, in a fragrance modifying composition, or in a perfume composition as an olfactory component in detergents (anionic detergents, cationic detergents, and nonionic detergents) and soaps; space deodorants; perfumes; colognes; bath preparations such as bath oil, bath salts; hair preparations such as lacquers, brilliantines, pomades and shampoos; cosmetic preparations such as creams, deodorants, hand lotions, sun screens; powders such as talcs, dusting powders, face powders and the like. When one or more of the α-oxy(oxo) sulfides of our invention is used in perfumed articles such as the foregoing, it can be used in amounts of 0.01% or lower. Generally, it is preferred not to use more than about 2% in the finished perfumed article, since the use of too much will tend to unbalance the total aroma and will needlessly raise the cost of the article.

When the α-oxy(oxo) sulfide and ether compound or compounds of our invention are used as food flavor adjuvants, or are used to augment or enhance the flavor or aroma characteristics of foodstuffs, the nature of the co-ingredients included with the said α-oxy(oxo) sulfides and ethers in formulating the product composition will also serve to augment the organoleptic characteristics of the ultimate foodstuff treated therewith.

As used herein in regard to flavors, the term "augment" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste."

As used herein in regard to food flavors, the term "enhance" is used herein to mean the intensification of a flavor or aroma characteristic or note without the modification of the quality thereof. Thus, enhancement of a flavor or aroma means that the enhancement agent does not add any additional flavor note.

As used herein the term "foodstuff" includes both solids and liquids, and ingestible materials or chewable but non-ingestible materials such as chewing gum. Such materials usually do, but need not, have nutritional value. Thus, foodstuffs include soups, convenience foods, beverages, gelatin desserts, dairy products, candies, vegetables, cereals, soft drinks, snacks and the like.

Substances suitable for use herein as co-ingredients or flavoring adjuvants are well known in the art for such use, being extensively described in the relevant literature. Apart from the requirements that any such materials be organoleptically compatible with the α-oxy(oxo) sulfides and ethers, non-reactive with the α-oxy(oxo) sulfides and ethers of our invention and ingestibly acceptable and thus non-toxic or otherwise non-deleterious, nothing particularly critical resides in the selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar, carrageenan; cellulose and cellulose derivatives such as carboxymethyl cellulowe and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disacchardies, e.g., sucrose corn syrup and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing

TABLE II

| COMPOUND | STRUCTURE | AROMA |
|---|---|---|
| 3-methylthio-4-heptanol | 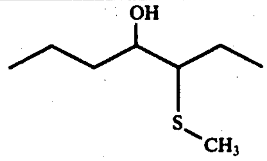 | At 1% in food grade ethanol, a sweet, green, floral, herbal, vetetative note. |
| 3-methylthio-4-heptanone | 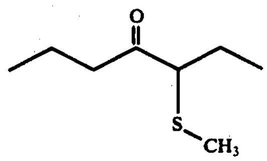 | At 1% in food grade ethanol a green, minty, herbaceous note with vegetative basil notes. |
| 3-propylthio-4-heptanol | 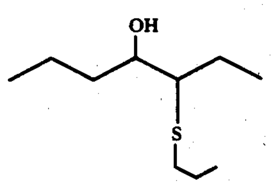 | Fatty, cucumber, onion (scallion, shallot) aroma with some green melon and floral nuances. |
| 3-thioacetyl-2,6-dimethyl-4-heptanone | 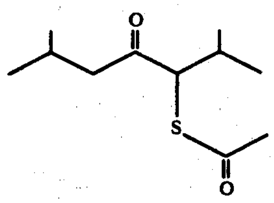 | At 1% in food grade ethanol, a sweet, meaty, vegetable aroma with somewhat of a grapefruit topnote. |
| 3-isobutylthio-4-heptanone | 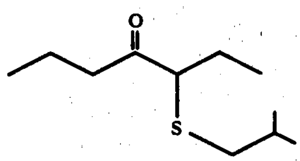 | Evaluated at 1% in food grade ethanol, a meaty onion aroma with a green, spicey and peppery nuance and an underlying bergamot note. |
| 3-isobutylthio-2,6-dimethyl-4-heptanol | 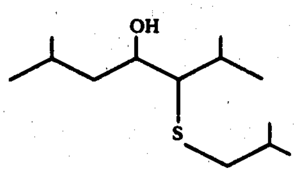 | Evaluated at 1% in food grade ethanol, a vetetable, green, horseradish, somewhat rubbery, onion-like aroma containg notes of hyacinth and narcisse. |
| 3-methylthio-2,6-dimethyl-4-heptanone | 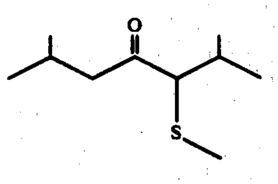 | Evaluated at 1% in food grade ethanol, a sweet, sulfurous, slightly floral and woody aroma with a fruity and berry nuance. |
| 3-(methallylthio)-2,6-dimethyl-4-heptanone | 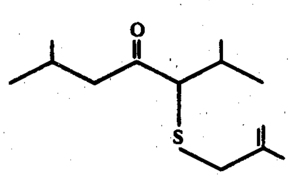 | At 1% in ethanol, a fruity, grapefruit, somewhat floral aroma with underlying yara neroli notes and bready, vegetative nuances. |

One or more of the aforementioned α-oxy(oxo) sulfides having the structure:

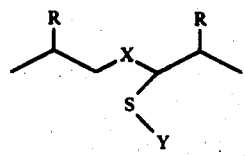

wherein X is one of:

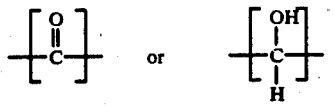

R is one of methyl or hydrogen, and Y is one of methyl, methallyl, acetyl, 1-propyl or 2-methyl-1-propyl is an olfactory agent and can be incorporated into a wide variety of compositions each of which will be enhanced or augmented by its sweet, green, floral, herbal, vegetative, basil-like, minty, melony, grapefruit, fruity and/or aliaceous notes and/or yara, neroli and/or verdima nuances.

The α-oxy(oxo) sulfides or mixture of α-oxy(oxo) sulfides can be added to perfume compositions as pure compounds or can be added to mixtures of materials in fragrance-imparting compositions to provide a desired fragrance character to a finished perfume material. The perfume and fragrance compositions obtained according to this invention are suitable in a wide variety of perfumed articles and can also be used to enhance, modify or reinforce natural fragrance materials. It will thus be appreciated that the α-oxy(oxo) sulfides of our invention is (are) useful as olfactory agent(s) and fragrance(s).

The term "perfume composition" is used herein to mean a mixture of compounds, including, for example, natural oils, synthetic oils, alcohols, aldehydes, ketones, esters, lactones, nitriles and frequently hydrocarbons which are admixed so that the combined odors of the individual components produce a pleasant or desired fragrance. Such perfume compositions usually contain (a) the main note or the bouquet or foundation-stone of the composition; (b) modifiers which round-off and accompany the main note; (c) fixatives which include odorous substances which lend a particular note to the perfume throughout all stages of evaporation, and substances which retard evaporation and (d) top-notes which are usually low-boiling, fresh-smelling materials. Such perfume compositions of our invention can be used in conjunction with carriers, vehicles, solvents, dispersants, emulsifiers, surface-active agents, aerosol propellants, and the like.

In perfume compositions the individual components contribute their particular olfactory characteristics, but the overall effect of the perfume composition will be the sum of the effect of each ingredient. Thus, one or more of the α-oxy(oxo) sulfides or our invention can be used to alter, augment, modify or enhance the aroma characteristics of a perfume composition or a perfumed article, for example, by highlighting or moderating the olfactory reaction contributed by another ingredient of the composition.

The amount of one or more of the α-oxy(oxo) sulfides of our invention which will be effective in perfume compositions depends upon many factors, including the other ingredients, their amounts and the effects which are desired. It has been found that perfume compositions containing as much as 2% or as litle as 0.005% by weight of the mixtures or compounds of this invention, or even less can be used to impart a buchu leaf oil-like aroma or a grapefruit oil-like aroma to soaps, cosmetics and other products. The amount employed will depend upon considerations of cost, nature of the end products, the effect desired in the finished product, and the particular fragrance sought.

One or more of the α-oxy(oxo) sulfides of our invention as disclosed herein can be used alone, in a fragrance modifying composition, or in a perfume composition as an olfactory component in detergents (anionic detergents, cationic detergents, and nonionic detergents) and soaps; space deodorants; perfumes; colognes; bath preparations such as bath oil, bath salts; hair preparations such as lacquers, brilliantines, pomades and shampoos; cosmetic preparations such as creams, deodorants, hand lotions, sun screens; powders such as talcs, dusting powders, face powders and the like. When one or more of the α-oxy(oxo) sulfides of our invention is used in perfumed articles such as the foregoing, it can be used in amounts of 0.01% or lower. Generally, it is preferred not to use more than about 2% in the finished perfumed article, since the use of too much will tend to unbalance the total aroma and will needlessly raise the cost of the article.

When the α-oxy(oxo) sulfide and ether compound or compounds of our invention are used as food flavor adjuvants, or are used to augment or enhance the flavor or aroma characteristics of foodstuffs, the nature of the co-ingredients included with the said α-oxy(oxo) sulfides and ethers in formulating the product composition will also serve to augment the organoleptic characteristics of the ultimate foodstuff treated therewith.

As used herein in regard to flavors, the term "augment" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste."

As used herein in regard to food flavors, the term "enhance" is used herein to mean the intensification of a flavor or aroma characteristic or note without the modification of the quality thereof. Thus, enhancement of a flavor or aroma means that the enhancement agent does not add any additional flavor note.

As used herein the term "foodstuff" includes both solids and liquids, and ingestible materials or chewable but non-ingestible materials such as chewing gum. Such materials usually do, but need not, have nutritional value. Thus, foodstuffs include soups, convenience foods, beverages, gelatin desserts, dairy products, candies, vegetables, cereals, soft drinks, snacks and the like.

Substances suitable for use herein as co-ingredients or flavoring adjuvants are well known in the art for such use, being extensively described in the relevant literature. Apart from the requirements that any such materials be organoleptically compatible with the α-oxy(oxo) sulfides and ethers, non-reactive with the α-oxy(oxo) sulfides and ethers of our invention and ingestibly acceptable and thus non-toxic or otherwise non-deleterious, nothing particularly critical resides in the selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar, carrageenan; cellulose and cellulose derivatives such as carboxymethyl cellulowe and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disacchardies, e.g., sucrose corn syrup and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptanal, 4-(p-hydroxyphenyl)-2-butanone, alpha-ionone, beta-ionone, methyl-3-butanone, 2-pentanone, 2-pentenal and propanal; alcohols such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, etyl butyrate, ethyl cuproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, Bulgarian rose, yara yara, natural raspberry oil and vanilla; lactones; sulfides, e.g., methyl sulfide and other materials such as maltol, pulegone mercaptan, α-phellandrene, ethyl maltol, 2,2,4,4,6,6-hexamethyl-S-trithiane, acetoin and acetals, (e.g., 1,1-diethoxyethane, 1,1-dimethoxyethane and dimethoxymethane.)

The specific flavoring adjuvant selected for use may be either solid or liquid depending upon the desired physical form of the ultimate product, i.e., foodstuff, whether simulated or natural, and should, in any event, be capable of providing an environment in which the α-oxy(oxo) sulfides and ethers can be dispersed or admixed to provide a homogeneous medium. In addition, selection of one or more flavoring adjuvants, as well as the quantities thereof, will depend upon the precise organoleptic character desired in the finished product. Thus, in the case of favoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of α-oxy(oxo) sulfides and ethers employed in a particular instance can vary over a relatively wide range whereby to its desired organoleptic effects having reference to the nature of the product are achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter the organoleptic characteristics of the parent composition, whether foodstuff per se or flavoring composition.

The use of insufficient quantities of α-oxy(oxo) sulfides and ethers will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of α-oxy(oxo) sulfides and ethers ranging from a small but effective amount, e.g., about 0.1 parts per million up to about 50 parts per million by weight based on total composition (more preferably, from about 0.2 ppm up to about 10 ppm) are suitable. Concentrations in excess of the maximum quantity stated are not normally recommended, since they fail to prove commensurate enhancement of organoleptic properties. In those instances, wherein the α-oxy(oxo) sulfides and ethers are added to the foodstuff as an integral component of a flavoring composition, it is, of course, essential that the total quantity of flavoring composition employed be sufficient to yield an effective α-oxy(oxo) sulfide and ether concentration in the foodstuff product.

Food flavoring compositions prepared in accordance with the present invention preferably contain the α-oxy(oxo) sulfides and ethers in concentrations ranging from about 0.1% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the α-oxy(oxo) sulfides and ethers with, for example, gum arabic, gum tragacanth, carageenan and the like, and thereafter spray-drying the resultant mixture wereby to obtain the particular solid product. Pre-prepared flavor mixed in powder form, e.g., a fruit-flavored powder mix, are obtained by mixing the dried solid components, e.g., starch, sugar and the like, and α-oxy(oxo) sulfides and ethers in a dry blender until the requisite degree of uniformity is achieved.

It is presently preferred to combine with the α-oxy(oxo) sulfides and ethers, the following adjuvants:

p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
Ethyl butyrate;
Acetic acid;
Gamma-undecalactone;
Naphthyl ethyl ether;
Diacetyl;
Ethyl acetate;
Anethole;
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene);
2-(4-hydroxy-4-methylpentyl) norbornadiene prepared according to U.S. application for Letters Patent Ser. No. 461,703 fuled on Apr. 17, 1974;
Natural blackcurrant juice;
Buchu leaf oil;
α-phellandrene;
Cis-3-hexen-1-ol;
Terpinenol-4;
Ethyl maltol;
Methyl benzoate;
Benzaldehyde;
Coriander oil;
α-ionone;
Ethyl heptanoate;
Methyl anthranilate;
Ethyl anthranilate;
Cinnamic alcohol;
Amyl valerinate;
Cinnamyl propionate;
Rodinyl acetate;
Methyl β-hydroxy butyrate;
Ethyl β-hydroxy butyrate;
2-phenyl-3-carboethoxyfuran;
Cyclohexyl disulfide;
Grapefruit oil;
Nootkatone;
Bergamot oil;
Citral;
Amyl alcohol;
5-phenyl-4-pentenal;
5-phenyl-2-pentenal;
Allyl caproate;
2-(n-pentyl) thiazole;
2-(i-butyl) thiazole;
2-(i-propyl) thiazole;
2-(n-propyl) thiazole;
2-phenyl-4-pentenal;
2-phenyl-4-pentenaldimethylacetal;
Methional;
4-methylthiobutanal;
2-ethyl-3-acetylpyrazine;
Tetramethyl pyrazine;
2-methyl pyrazine;
trans-2-hexenal;
Hydrolyzed vegetable protein;
Monosodium glutamate;
Dimethyl disulfide;
Methyl propyl disulfide;
Methyl propenyl disulfide;
Methyl allyl disulfide;
Allyl propyl disulfide;
Propyl propenyl disulfide;
Dipropyl disulfide;
Diallyl disulfide;
Propyl propenyl trisulfide;
Thiopropanal-S-oxide;
Thiobutanal-S-oxide;
Thioethanal-S-oxide;
Thiohexanal-S-oxide; and
Propyl propene thiosulfonate.

The following examples are given to illustrate embodiments of the invention as it is presently preferred to practice it. It will be understood that these examples are illustrative and that the invention is not to be considered as restricted thereto except as indicated in the appended claims.

BRIEF DESCRIPTION OF THE DRAWINGS

FIG. 14(A) is the NMR spectrum for the product of Example II(G) wherein 3-[(methoxycarbonyl)methylthio]-2,6-dimethyl-4-heptanone is produced.

FIG. 14(B) is the IR spectrum for the product of Example II(G) wherein 3-[(methoxycarbonyl)methylthio]-2,6-dimethyl-4-heptanone is produced.

EXAMPLE I

(A) PREPARATION OF 3-CHLORO-4-HEPTANONE

Figure 1:
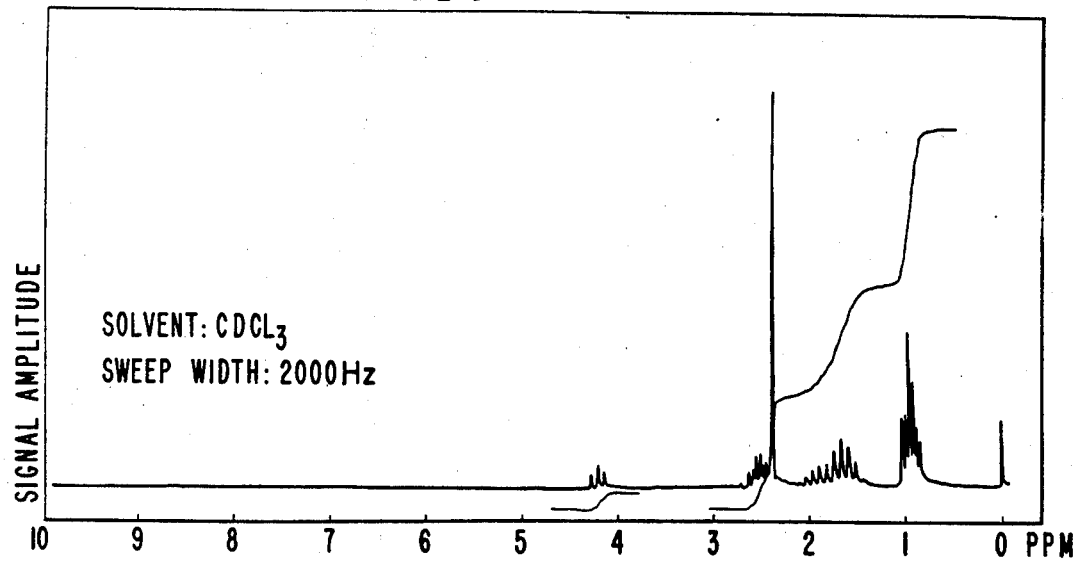
FIG. 1 is the NMR spectrum for the product of Example I(B) wherein 3-thioacetyl-4-heptanone is produced.

Reaction:

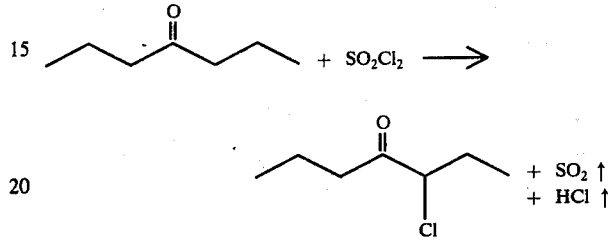

Into a 3000 ml, three-necked, round-bottom flask, equipped with mechanical stirrer, 500 ml addition funnel, Y-tube, pot thermometer and gas outlet tube with rubber tubing leading over a stirring solution of 10% sodium hydroxide is added 1000g 4-heptanone. Addition of 434 g of $SO_2Cl_2$ drop-wise into the 4-heptanone is commenced while maintaining the pot temperature in the range of 22°-34° C and is continued over a period of two hours. A water aspirator vacuum is applied to the reaction mass in order to pull the acidic gases; sulfur dioxide and hydrogen chloride, over the sodium hydroxide solution.

The reaction mass is periodically sampled using GLC analysis until such time as about 25% chlorinated ketone product is found to be present.

While maintaining the reaction mass at 15° C, 1000 ml saturated sodium chloride is added to the mixture, and the mixture is then stirred for a period of 10 minutes. The reaction mass is thens transferred to a 5-liter separatory funnel and shaken well, whereupon the organic and aqueous phases separate. The lower aqueous phase (approximately 1000 ml) has a pH of about 1. The upper organic phase is washed with 700 ml saturated sodium bicarbonate solution to a pH of 6-7. The organic phase is then dried over 50 grams anhydrous sodium sulfate and filtered yielding a yellow oil weighing 1063 grams. The organic layer is determined to contain 24.9% chlorinated ketone and 68.1% original ketone starting material. This material is then vacuum distilled by first adding it to a 2000 ml, three-necked, round-bottom flask equipped with a 2.5 × 60 cm vacuum jacketed column packed with 6 mm Raschig Rings, and then equipped with an automatic reflux head, a pot thermometer, a heating mantle, a vacuum pump and a dry-ice trap. Fractionation data is as follows:

| Vacuum (mmHg) | Pot Temp. | Vapor Temp. | Weight of Fraction | Cut No. | Reflux Ratio |
|---|---|---|---|---|---|
| 62 | 80 | 71 | 51.0 g | 1 | 60:40 |
| 62 | 81.5 | 71 | 149.0 g | 2 | 40:60 |
| 58 | 82.5 | 70 | 157.5 g | 3 | 30:70 |
| 59 | 89.5 | 70 | 175.0 g | 4 | 30:70 |
| 59 | 96 | 75 | 110. g | 5 | 30:70 |
| 59 | 100 | 80 | 24.5 g | 6 | 50:50 |
| 58 | 101 | 90 | 16.0 g | 7 | 50:50 |
| 58 | 102 | 94 | 37.5 g | 8 | 30:70 |
| 55 | 103 | 94 | 144.5 g | 9 | 30:70 |

-continued

| Vacuum (mmHg) | Pot Temp. | Vapor Temp. | Weight of Fraction | Cut No. | Reflux Ratio |
|---|---|---|---|---|---|
| 54 | 110 | 95 | 85.0 g | 10 | 30:70 |
| 54 | 119 | 102 | 28.0 g | 11 | 30:70 |
| 15 | 140 | 80 | 45.0 g | 12 | 30:70 |

GLC analysis on each of cuts 5-12 (conditions 8 feet × ¼inch SE-30 column) yields the following information:

| Cut No. | Percent low Boilers | Percent 4-Heptanone | Percent 3-Cl 4-Heptanone | Percent High Boiler (A) | Percent High Boiler (B) | Percent High Boiler (C) | Percent High Boiler (D) |
|---|---|---|---|---|---|---|---|
| 5 | 0.09 | 96.15 | 2.97 | — | — | — | — |
| 6 | | | | | | | |
| 7 | | 50 % | 50 % | | | | |
| 8 | — | 9.28 | 87.09 | 2.43 | 0.57 | — | — |
| 9 | — | trace | 95.78 | 3.22 | 1.00 | — | — |
| 10 | — | — | 91.38 | 4.89 | 3.34 | 0.21 | — |
| 11 | — | — | 69.14 | 7.27 | 19.88 | 3.71 | — |
| 12 | — | — | 8.32 | 2.07 | 49.28 | 39.69 | 0.47 |

Cuts 8, 9 and 10 are blended (weight 266.5 gms) and are analyzed as follows:
0.95%: 4-heptanone
93.89%: 3-chloro-4-heptanone
3.60%: high boiler A
1.57%: high boiler B

EXAMPLE I

(B) PREPARATION OF 3-THIOACETYL-4-HEPTANONE

Reaction:

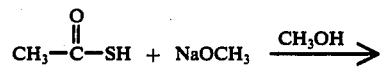

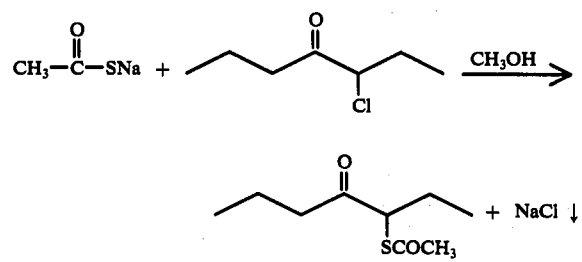

Into a 25 ml, three-necked, round-bottom flask equipped with a magnetic stirrer, nitrogen inlet tube, 6 inches Vigreux column with cotton plug and pot thermometer is added a solution of 0.27 grams sodium methoxide in 3 ml anhydrous methanol (0.005 moles sodium methoxide). Under dry nitrogen, 0.38 grams of thioacetic acid dissolved in 3 ml anhydrous methanol (0.005 moles thioacetic acid) is then added to the sodium methoxide solution over a 2-minute period. A solution of 3-chloro-4-heptanone in methanol (0.75 grams 3-chloro-4-heptanone dissolved in one ml anhydrous methanol) prepared according to Pat A, supra (cuts 8, 9 and 10 blended) is then added to the reaction mass which becomes turbid. Stirring is continued for a period of one hour, whereupon GLC analysis (condition: 8 feet × ¼ inch SE-30 column) yields the following data:
15.6%: 3-chloro-4-heptanone
3.0%: chloro heptanone, high boiler
77.67%: major peak
2.37%: late peak With stirring, 15 ml water is added to the reaction mass which then splits up into two phases, an aqueous phase and an organic phase. The pH of the aqueous phase is 5-6. The organic phase is extracted with two 10 ml portions of methylene chloride. The methylene chloride extracts are combined and washed with 5 ml saturated sodium chloride solution. The organic phase is then dried over anhydrous sodium sulfate and concentrated in a rotary evaporator using water aspirator vacuum yielding 0.65 grams of a dark amber oil. GLC trapping of the major peak (Conditions: 8 feet × ¼ inch SE-30 column operated at 120° C, programmed at 5° C/minute) yields a compound having a molecular weight of 188 and having a mass spectral analysis, NMR analysis and IR analysis which causes confirmation of the structure:

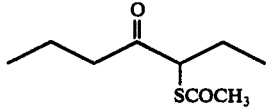

Figure 2:
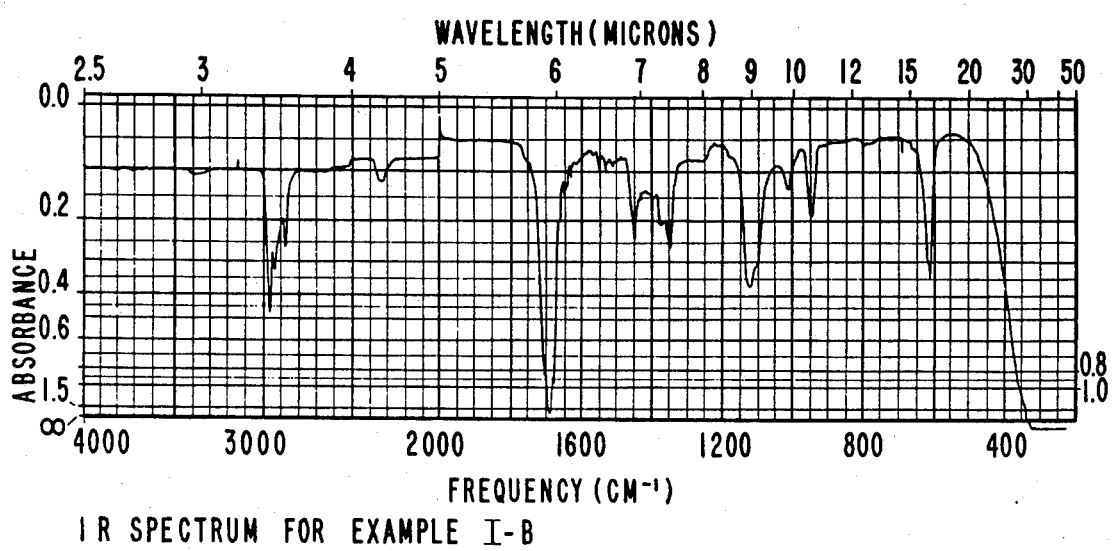
FIG. 2 is the IR spectrum for the product of Example I(B) wherein 3-thioacetyl-4-heptanone is produced.

The NMR spectrum is set forth in FIG. 1. The IR spectrum is set forth in FIG. 2.

The NMR analysis is as follows:

| 3-thioacetyl-4-heptanone | | | |
|---|---|---|---|
| 0.92 ppm | (t) | $CH_3—CH_2$ | |
| 0.96 | (t) | $CH_3—C—C—S$ | } 6H |
| 2.01-1.44 | (m) | $—CH_2—$ | 4H |
| 2.39 | (s) | $CH_3—\overset{O}{\underset{\|}{C}}—S—$ | } 5H |
| 2.53 | (m) | $—CH_2—\overset{O}{\underset{\|}{C}}—$ | |
| 4.20 | (t) | $O=C—HC—S—C=O$ | 1H |

The IR analysis is as follows: 620 cm$^{-1}$, 950, 1125, 1350, 1450, 1690, 2320, 2870, 2930, 2960.

Material prepared similarly to above example was vacuum distilled yielding 99.3% pure product (boiling point 93.5°-94.5° C at 2.8 mm Hg). The thus-distilled material has the same physical properties as set forth above for 3-thioacetyl-4-heptanone.

EXAMPLE I

(C) PREPARATION OF 3-THIOMETHYL-4-HEPTANONE

Reaction:

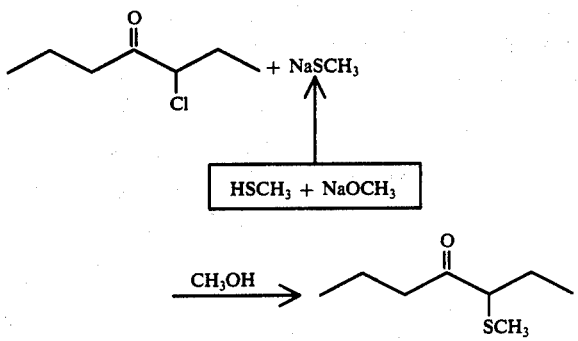

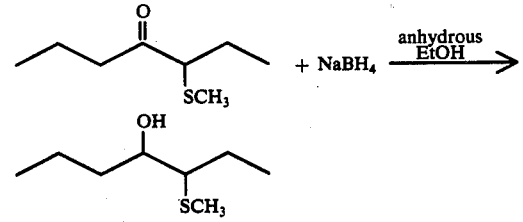

Into a 50-ml, three-necked, round-bottom flask equipped with magnetic stirrer, dry ice condenser, pot thermometer, cold water bath, reflux condenser with nitrogen inlet tube and nitrogen bubbler, is placed a solution of 0.54 grams of sodium methoxide in 6 ml anhydrous methanol (0.01 moles sodium methoxide). The sodium methoxide solution is then cooled using the cold-water bath to a temperature of 25° C. The nitrogen flow is ceased and methyl mercaptan in methanol (0.48 grams methyl mercaptan in 6 ml anhydrous methanol, 0.01 moles methyl mercaptan) is added to the reaction mass while maintaining same at 24° C. At 24° C, a solution of 1.49 grams of 3-chloro-4-heptanone in 2 ml anhydrous methanol (0.01 moles 3-chloro-4-heptanone) is added to the reaction mass. The 3-chloro-4-heptanone is produced according to the process set forth in part (A), supra. The reaction mass is maintained, with stirring, at 25° C for a period of one hour and 15 minutes. At the end of this period, the reaction mass is flushed with nitrogen. The reaction mass is then concentrated on a rotary evaporator using a water aspirator vacuum to approximately 5 ml.

Distilled water (15 ml) is then added to the concentrated reaction mixture whereupon the reaction mixture forms into two phases; an oil phase and an aqueous phase. The pH of the aqueous phase is in the range of 5-6. The oil phase is then extracted with two 12-ml portions of n-hexane and the phases are separated. The hexane extracts are combined, washed with water (5 ml), dried over anhydrous sodium sulfate, gravity filtered and concentrated on a rotary evaporator to a weight of 1.29 grams. The resulting product contains 90.1% 3-thiomethyl-4-heptanone by GLC analysis having the structure:

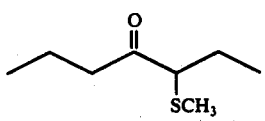

as confirmed by NMR, IR and mass spectral analyses of trapped compound.

Figure 3:
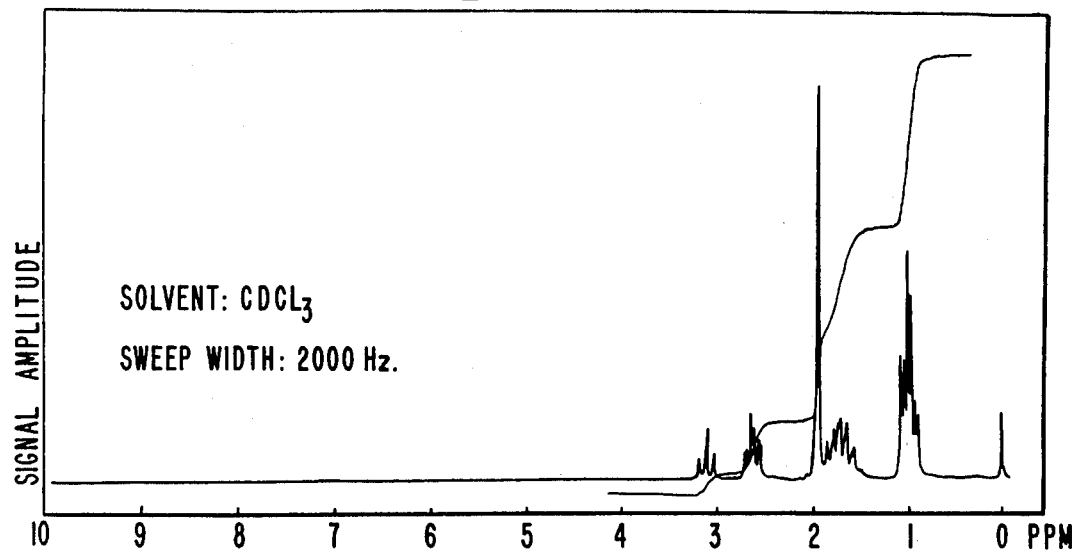
FIG. 3 is the NMR spectrum for the product of Example I(C) wherein 3-thiomethyl-4-heptanone is produced.
Figure 4:
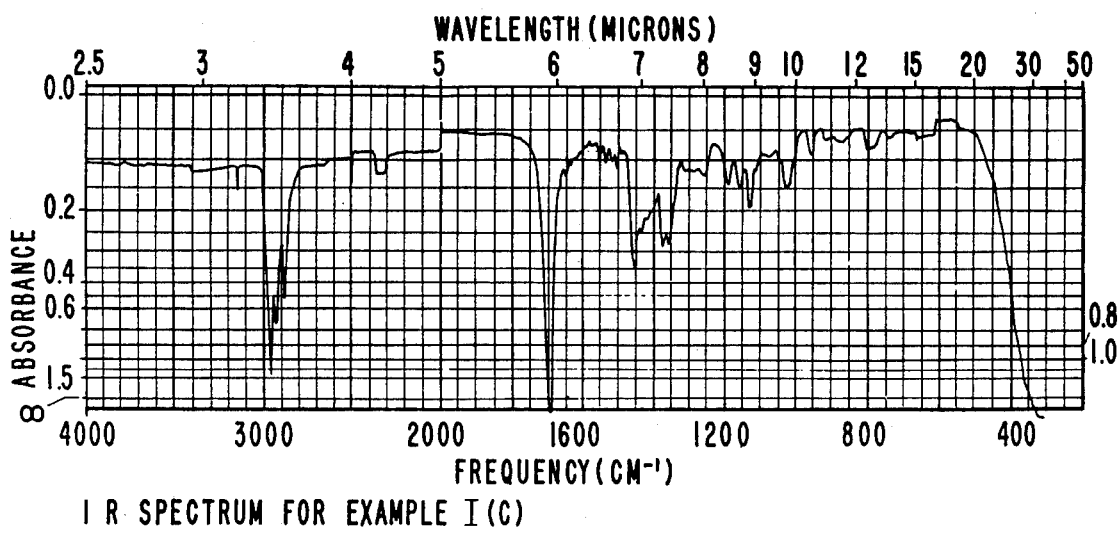
FIG. 4 is the IR spectrum for the product of Example I(C) wherein 3-thiomethyl-4-heptanone is produced.

The NMR spectrum is set forth in FIG. 3. The IR spectrum is set forth in FIG. 4.

The NMR analysis is as follows:

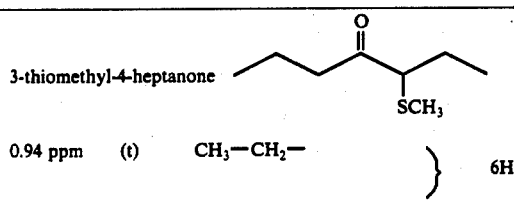

| 0.94 ppm | (t) | CH$_3$—CH$_2$— | 6H |
|---|---|---|---|
| 0.97 | (t) | CH$_3$—C—C—S— | |
| 1.68 | (m) | —CH$_2$— | 4H |
| 1.92 | (s) | CH$_3$—S— | 3H |
| 2.60 | (m) | —CH$_2$—C(=O)— | 2H |
| 3.08 | (t) | C(=O)—HC—S— | 1H |

The IR analysis is as follows: 1360 cm$^{-1}$, 1375, 1455, 1690, 2330, 2880, 2930, 2960.

Material prepared similarly to above example was vacuum distilled yielding 99.2% pure product (boiling point 78–78.5° C at 8.5 mm Hg). The thus-distilled material has the same physical properties as set forth above for 3-thiomethyl-4-heptanone.

EXAMPLE I (D) PREPARATION OF 3-THIOMETHYL-4-HEPTANOL

Reaction:

Into a 25 ml, three-necked, round-bottom flask equipped with magnetic stirrer, nitrogen inlet tube, reflux condenser, pot thermometer, and cold water bath, is added a solution of 0.10 grams sodium borohydride (NaBH$_4$) dissolved in 4 ml anhydrous ethyl alcohol (0.00265 moles sodium borohydride). While maintaining the pot temperature at 25° C, a solution of 0.8 grams of 3-thiomethyl-4-heptanone in 3.5 ml anhydrous ethyl alcohol is added to the sodium borohydride-ethanol solution over a one-minute period. The reaction mass then warms up to about 30° C and is maintained at a temperature of between 25° to 30° C for a period of about 1.5 hours. At the end of this period another 0.05 grams (0.00133 moles) of sodium borohydride and 2 ml ethanol is added.

After 10 minutes of stirring while maintaining the reaction mass at 25° C, the reaction mass is then worked up as follows. The reaction mixture is concentrated to about 4 ml of a thick slurry using water aspirator vacuum. The resulting thick slurry is then combined with 12 ml water thereby causing the solid to dissolve, and the reaction mass to exist in two phases; an aqueous phase and an organic phase. The aqueous phase is acidified to a pH of 2-3 using 10% HCl solution. The organic phase is extracted with two 12-ml portions of methylene chloride. The extracts are then combined, washed with 8 ml water, dried over anhydrous sodium sulfate, gravity filtered and then concentrated on a rotary evaporator (using water aspirator vacuum) to a weight of 5.8 grams. The desired product trapped out on an 8 foot × ¼ inch SE-30 GLC column, and MS, NMR and IR analyses confirm that the resulting compound has the structure:

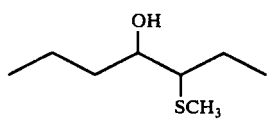

Figure 5:
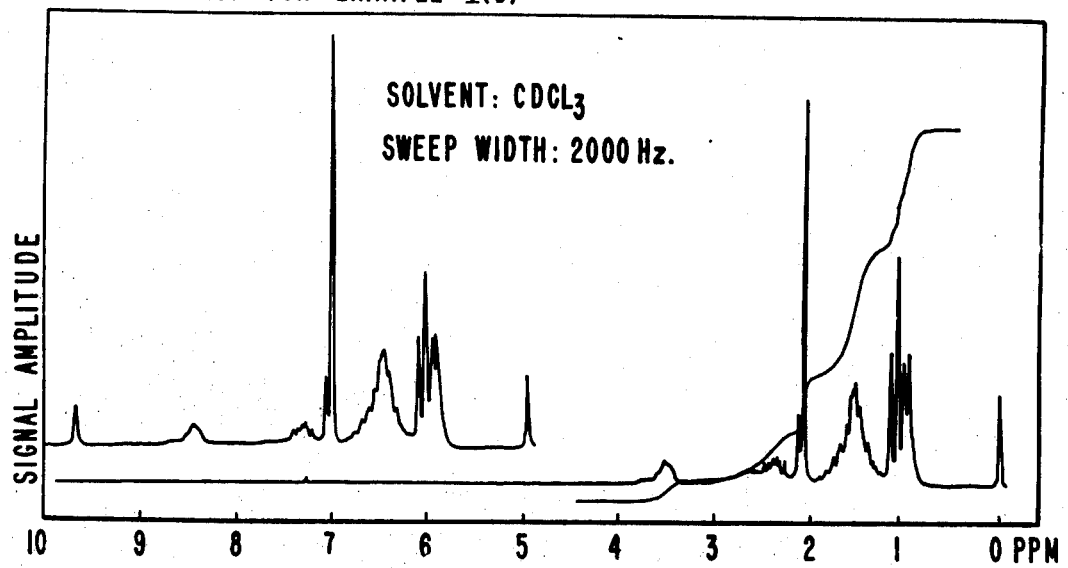
FIG. 5 is the NMR spectrum for the product of Example I(D) wherein 3-thiomethyl-4-heptanol is produced.
Figure 6:
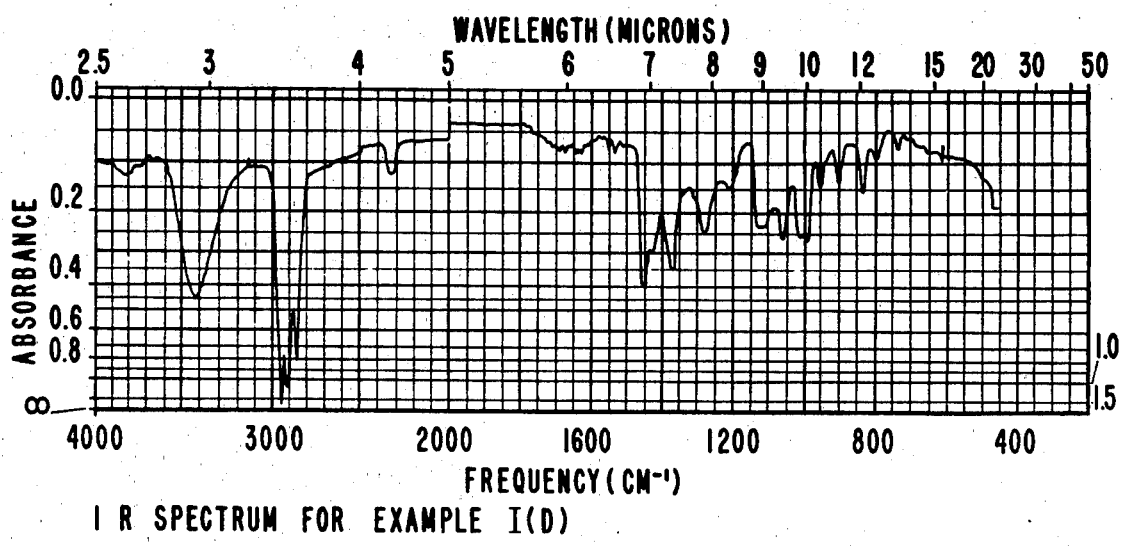
FIG. 6 is the IR spectrum for the product of Example I(D) wherein 3-thiomethyl-4-heptanol is produced.

The NMR spectrum is set forth in FIG. 5. The infrared spectrum is set forth in FIG. 6.

The NMR analysis is as follows:

| | | | |
|---|---|---|---|
| 0.94 ppm | (t) | CH₃—CH₂— | 6H |
| 1.06 | (t) | CH₃—C—C—S— | |
| 1.51 | (m) | —CH₂— | 6H |
| 2.06 | (s) | CH₃—S— | 3H |
| 2.36 | (m) | HC—S— | 2H |
| 2.62 | (broad) | —OH | |
| 3.52 | (m) | HC—O— | 1H |

The IR analysis is as follows: 980 cm⁻¹, 1010, 1065, 1370, 1430, 1450, 2320, 2860, 2920, 2960, 3440.

Material prepared similarly to above example was vacuum distilled yielding 99.5% pure product (boiling point 64°-64.5° C at 1.5 mm Hg). The thus-distilled material has the physical properties as set forth above for 3-thiomethyl-4-heptanol.

EXAMPLE II

PREPARATION OF 3-METHALLYLTHIO-2,6-DIMETHYL-4-HEPTANONE

A. Preparation of 3-chloro-2,6-dimethyl-4-heptanone

Reaction:

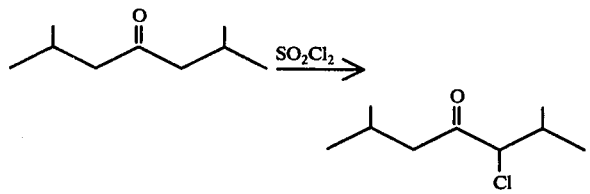

Into a one-liter, three-necked, round-bottom flask equipped with Y tube, pot thermometer, mechanical stirrer, 125 ml addition funnel, gas outlet tube, cold water bath and water aspirator vacuum is added 356 grams of 2,6-dimethyl-4-heptanone (2.4 moles). Over a period of one hour, 67.5 grams (40 ml; 0.5 moles) of SO₂Cl₂ is slowly added to the ketone with stirring while maintaining the reaction mass temperature in the range of 23°-35° C.

The reaction mass is then evacuated slowly using water aspirator vacuum thereby removing most of the acidic gases resulting from the foregoing reaction.

The reaction mass is then transferred to a one-necked, one-liter, round-bottom flask and the last traces of acidic gases are removed thus yielding 371 grams of product. The reaction mass is then equipped to a 500 ml, three-necked, round bottom flask equipped with a 2.0 × 30 cm distillation column packed with ⅛ inch helices, reflux head, magnetic stirrer, heating mantle and vacuum pump and the resulting 3-chloro-2,6-dimethyl-4-heptanone is fractionally distilled at a vapor temperature of 106°-107° C and a pressure of 45-46 mm Hg yielding a product of 97% purity as confirmed by GLC, mass spectral, NMR and IR analyses.

EXAMPLE II

B. Preparation of 3-mercapto-2,6-dimethyl-4-heptanone

Reaction:

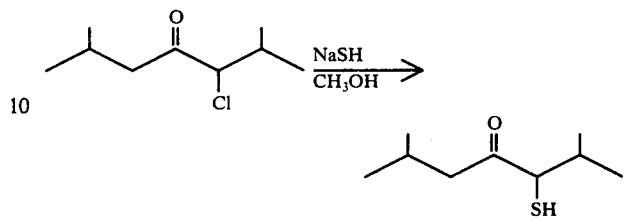

Into a 250 ml, round bottom, three-necked flask equipped with magnetic stirrer, pot thermometer, 6 inches Vigreux distillation column with gas outlet at top leading over 200 ml 10% sodium hydroxide solution, H₂S gas inlet tube (sub-surface), Y tube, 50 ml addition funnel, gas bubbler, and dry ice-isopropyl alcohol bath, and cold water bath is added a solution of 11.6 grams of sodium methoxide dissolved in 90 ml anhydrous methanol. The sodium methoxide solution is cooled to a temperature of −15° C using the dry ice-isopropanol bath. While maintaining the temperature of the sodium methoxide solution at −10° to −5° C, hydrogen sulfide is bubbled into the reaction mass over a period of 2 hours. While continuing to bubble in hydrogen sulfide and maintaining the reaction mass at a temperature in the range of −5° to −9° C, the 3-chloro-2,6-dimethyl-4-heptanone prepared in Part A of this example (18.2 grams; 0.100 moles) is added slowly to the reaction mass from the additional funnel over a period of 13 minutes. The reaction mass is then maintained at a temperature of 0°-26° C for a period of 4 hours (25°-26° C for the last 1.5 hours).

The reaction mass is then concentrated to approximately 25 ml (thick slurry) using a rotary evaporator and water aspirator vacuum. 85 ml distilled water is then added to the reaction mass, with stirring, while maintaining the temperature at 25° C, thereby yielding a turbid yellow solution. 85 grams of 10% aqueous sodium hydroxide is then added to the resulting mixture whereupon the temperature rises from 25° C to 28° C (pH = 10-11). The basic aqueous solution is then extracted with two 70 ml portions of methylene chloride and the extracts are combined, dried and concentrated yielding 1.7 grams of an oil. The basic aqueous solution is then acidified with 115 ml 10% hydrochloric acid to a pH of 1-2. This is then extracted with four 50 ml portions of methylene chloride. The methylene chloride extracts are combined and washed with two 35 ml portions of saturated sodium chloride (to a pH of 5) and dried over anhdyrous sodium sulfate. The resulting mixture is gravity filtered and concentrated on a rotary evaporator to yield 15.5 grams of product containing 96.1% 3-mercapto-2,6-dimethyl-4-heptanone as confirmed by mass spectral, MNR and IR analyses. This material is vacuum distilled at a vapor temperature of 77.5°-78° C and a pressure of 6 mm Hg.

EXAMPLE II

C. Preparation of 3-methallylthio-2,6-dimethyl-4-heptanone

Reaction:

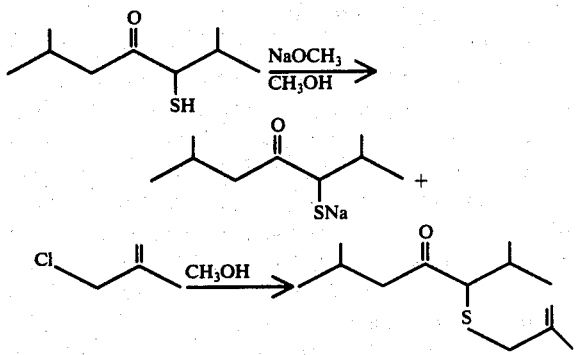

Into a 25 ml, three-necked, round bottom flask equipped with magnetic stirrer, Y tube, nitrogen inlet, reflux condenser with cotton plug, cold water bath and warm water bath is added a solution of 0.162 grams of sodium methoxide dissolved in 2 ml anhydrous methanol. Over a period of 1 minute is added a solution of 0.522 grams of 3-mercapto-2,6-dimethyl-4-heptanone dissolved in 3 ml anhydrous methanol, with stirring. After stirring 12 minutes at 24°–25° C, a solution of 0.3 grams of 3-chloro-2-methylpropene in 1 ml anhydrous methanol is added. With a water bath, the resulting reaction mass is warmed to 31° C and the reaction mass is then stirred while maintaining the temperature in the range of 23°–30° C for a period of 2 hours.

The reaction mass is then concentrated on a rotary evaporator using water aspirator vacuum to approximately 4 ml yielding a slurry. To the slurry is added 8 ml water and the solid dissolves. The reaction mass is then acidified to a pH of 1–2 with 3 drops of 10% hydrochloric acid. The reaction mass is then extracted with three 8 ml portions of methylene chloride and the extracts are combined, washed with 10 ml water, dried over anhydrous sodium sulfate and gravity filtered. The extracts are concentrated on a rotary evaporator to yield 0.54 grams of a white oil containing 93.6% by GLC of 3-methallylthio-2,6-dimethyl-4-heptanone as confirmed by MS, IR and NMR analyses of trapped product.

Figure 7:
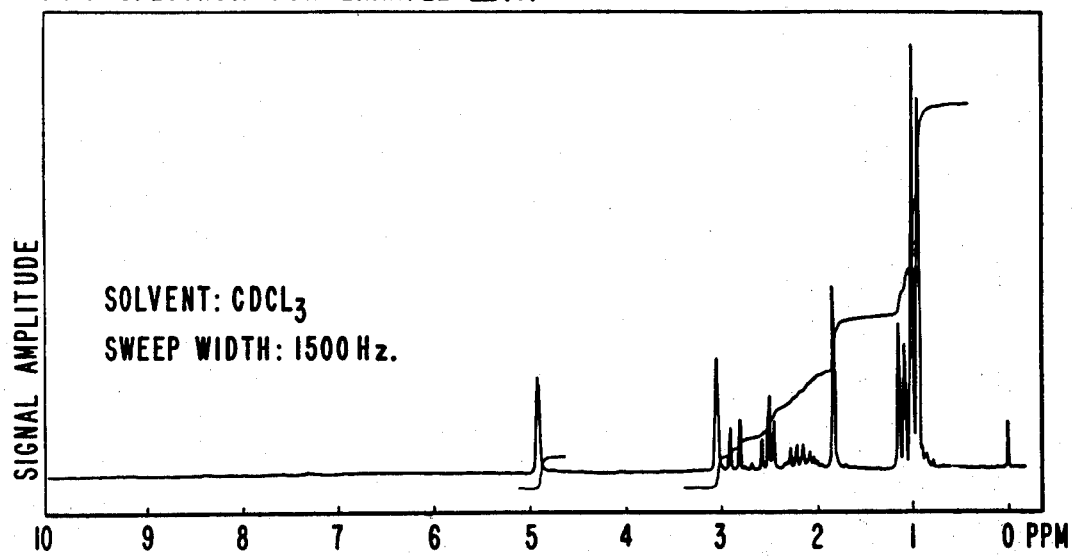
FIG. 7 is the NMR spectrum for the product of Example II(C) wherein 3-methallylthio-2,6-dimethyl-4-heptanone is produced.
Figure 8:
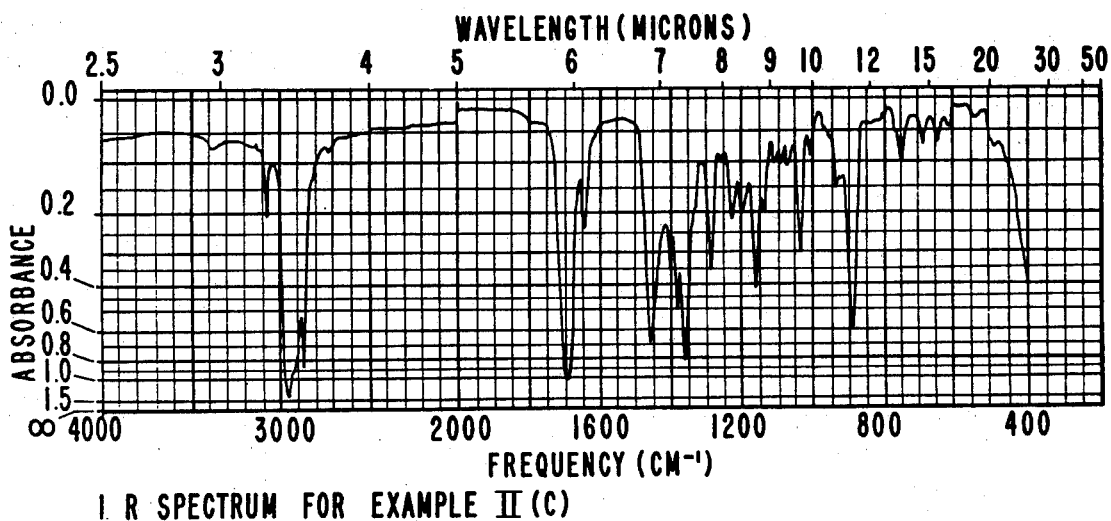
FIG. 8 is the IR spectrum for the product of Example II(C) wherein 3-methallylthio-2,6-dimethyl-4-heptanone is produced.

The NMR spectrum is set forth in FIG. 7. The infrared spectrum is set forth in FIG. 8.

The mass spectrum analysis is as follows:

| m/e | Relative Intensity |
|---|---|
| 41 | 29 |
| 55 | 44[3] |
| 57 | 37[6] |
| 69 | 10 |
| 85 | 43[5] |
| 87 | 93[2] |
| 109 | 33 |
| 142 | 44[4] |
| 143 | 100[1] |
| M 228 | 28 |

The NMR analysis is as follows:

| | | | |
|---|---|---|---|
| 1.92 ppm, 2.06 | (2 doublets) | H<br>CH$_3$—C— | 12H |
| 1.78 | (s) | =C—CH$_3$ | 3H |
| 2.12 | (m) | methine protons | 2H |
| 2.47 | (t) | —CH$_2$— | 2H |
| 2.82 | (d) | O=C—C—S—<br>H | 1H |
| 3.01 | (s) | =C—CH$_2$—S— | 2H |
| 4.86 | (s) | $C=C\begin{smallmatrix}H\\H\end{smallmatrix}$ | 2H |

The IR analysis is as follows: 890 cm$^{-1}$, 1035, 1160, 1200, 1225, 1285, 1360, 1380, 1400, 1460, 1640, 1695, 2870, 2960, 3080.

Material prepared similarly to above example was vacuum distilled yielding 99.8% pure product (boiling point 100°–100.5° C at 1.3 mm Hg). The thus-distilled material has the same physical properties as set forth for 3-methyallylthio-2,6-dimethyl-4-heptanone.

EXAMPLE II

D. PREPARATION OF 3-CROTYLTHIO-2,6-DIMETHYL-4-HEPTANONE

Reaction:

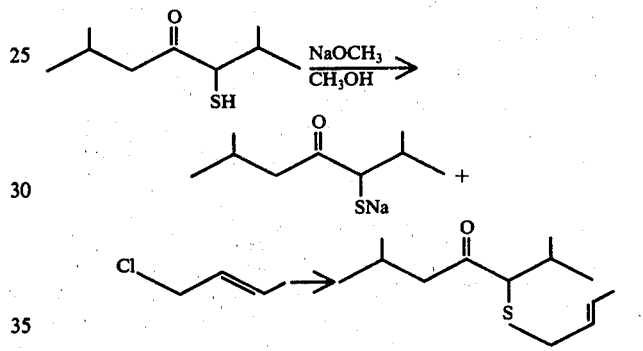

Into a 25 ml, three-necked, round bottom flask equipped with magnetic stirrer, reflux condenser, nitrogen inlet tube and cold water bath is placed a solution of 0.162 grams (0.003 moles) of sodium methoxide dissolved in 2 ml anhydrous methanol. Using the cooling bath the temperature of the sodium methoxide solution is cooled to 23° C at which point a solution of 0.52 grams (0.003 moles) of 3-mercapto-2,6-dimethyl-4-heptanone in 2 ml anhydrous methanol is added to the sodium methoxide solution. While maintaining the temperature of the reaction mass at 24°–29° C and over a period of 2 minutes, a solution of 0.300 grams of 80% crotyl chloride dissolved in 2 ml anhydrous methanol (0.0026 moles crotyl chloride) is added to the reaction mass with stirring. The reaction mass is continued to be stirred for a period of 2.5 hours and is then concentrated on a rotary evaporator using water aspirator vacuum to 2 ml product (solid/oil slurry). Nine ml water is added to the reaction mass thereby dissolving the solid. The oil is extracted with three 8 ml portions of methylene chloride and the extracts are combined and washed with 6 ml water. The methylene chloride extracts are then dried over anhyrous sodium sulfate, gravity filtered and concentrated on a rotary evaporator to 0.59 grams pale yellow oil. The major product is isolated using GLC apparatus (8 feet × ¼ inch Carbowax column). NMR, mass spectral and IR analyses yield the information that the resulting material is 3-crotylthio-2,6-dimethyl-4-heptanone having the structure:

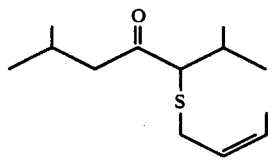

Figure 9:
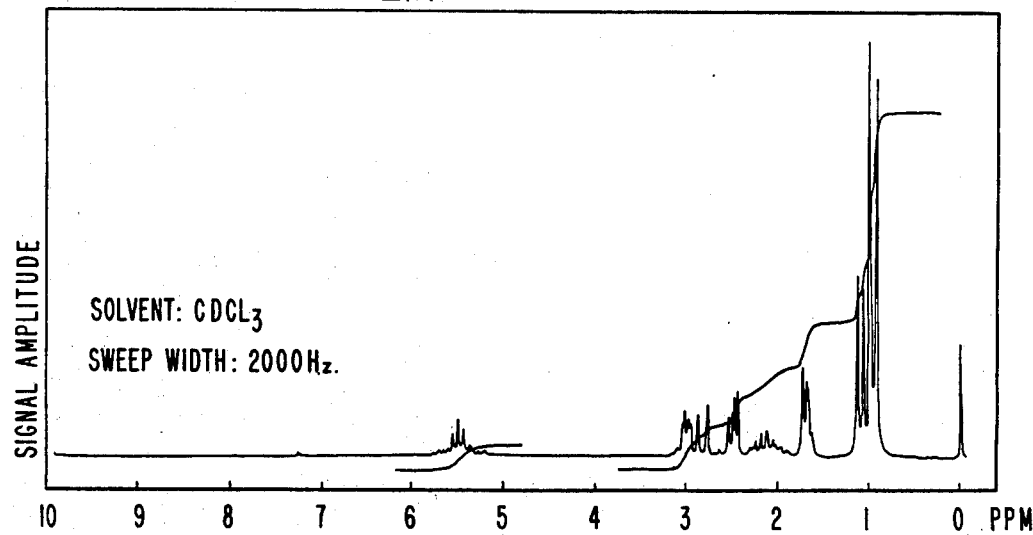
FIG. 9 is the NMR spectrum for the product of Example II(D) wherein 3-crotylthio-2,6-dimethyl-4-heptanone is produced.
Figure 10:
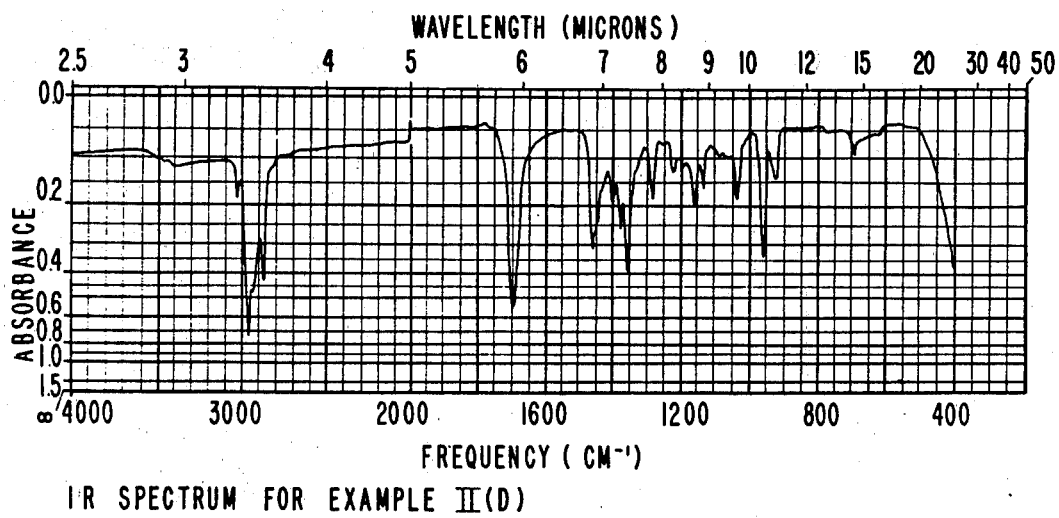
FIG. 10 is the IR spectrum for the product of Example II(D) wherein 3-crotylthio-2,6-dimethyl-4-heptanone is produced.

The NMR spectrum is set forth in FIG. 9. The infrared spectrum is set forth in FIG. 10.

The mass spectral analysis is as follows:

| m/e | Relative Intensity |
|---|---|
| 41 | 20 |
| 55 | 90[2] |
| 57 | 37[5] |
| 85 | 36[6] |
| 87 | 100[1] |
| 89 | 33 |
| 141 | 22 |
| 142 | 45[4] |
| 143 | 63[3] |
| M 228 | 13 |

The NMR analysis is as follows:

| | | | |
|---|---|---|---|
| 0.84 ppm, 1.08 | (doublets) | $CH_3-$ | 12H |
| 1.70 | (d) | $=C-CH_3$ | 3H |
| 2.14 | (m) | methine protons | 2H |
| 2.48 | (m) | $-CH_2-C=O$ | 2H |
| 2.82 | (d) | $O=C-HC-S-$ | 1H |
| 2.99 | (m) | $=C-CH_2-S-$ | 2H |
| 5.50 | (m) | olefinic protons | 2H |

The infrared analysis as is as follows: 960 cm$^{-1}$, 1035, 1135, 1160, 1285, 1360, 1380, 1400, 1465, 1695, 2870, 2930, 2960, 3020.

EXAMPLE II

E. PREPARATION OF 3-ALLYLTHIO-2,6-DIMETHYL-4-HEPTANONE

Reaction:

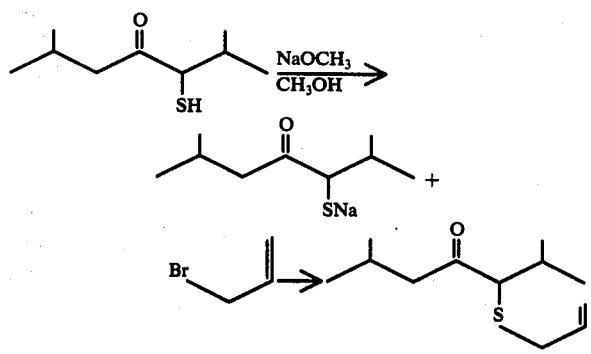

Into a 25 ml, round-bottom, three-necked flask equipped with magnetic stirrer, reflux condenser, nitrogen inlet tube and cold water bath is placed a solution of 0.162 grams (0.03 moles) of sodium methoxide dissolved in 2 ml anhydrous methanol. Using the water bath the temperature of the sodium methoxide solution is reduced to 23° C. At 23° C a solution of 0.522 grams (0.003 moles) of 3-mercapto-2,6-dimethyl-4-heptanone dissolved in 3 ml anhydrous methanol is added to the sodium methoxide solution. Subsequent to the addition of the mercapto ketone, after stirring for 15 minutes at 23° C, a solution of 0.40 grams (0.0033 moles) of allyl bromide dissolved in 2 ml anhydrous methanol is added to the reaction mass with stirring. The reaction mass warms to 33° C and is continued to be stirred at 25°-33° C for a period of 2 hours. It is concentrated on a rotary evaporator using water aspirator vacuum to a volume of 3 ml, thus yielding a white slurry. Eight ml water is then added to the slurry thereby dissolving the solid therein. One drop of 10% HCl is added to the resulting material thereby reducing the pH from about 9 to about 5. The reaction mass now existing in two phases is extracted with three 8 ml volumes of methylene chloride. The extracts are combined and washed with 6 ml water and then dried over anhydrous sodium sulfate, gravity filtered and concentrated on a rotary evaporator to a weight of 0.55 grams (pale yellow oil). GLC analysis (8 feet × ¼ inch SE-30 column), NMR, IR and mass spectral analyses of GLC isolated material confirm that the resulting product is 97% product, 3-allylthio-2,6-dimethyl-4-heptanone, having the structure:

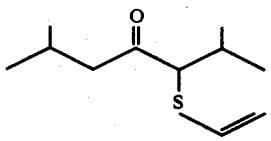

Figure 11:
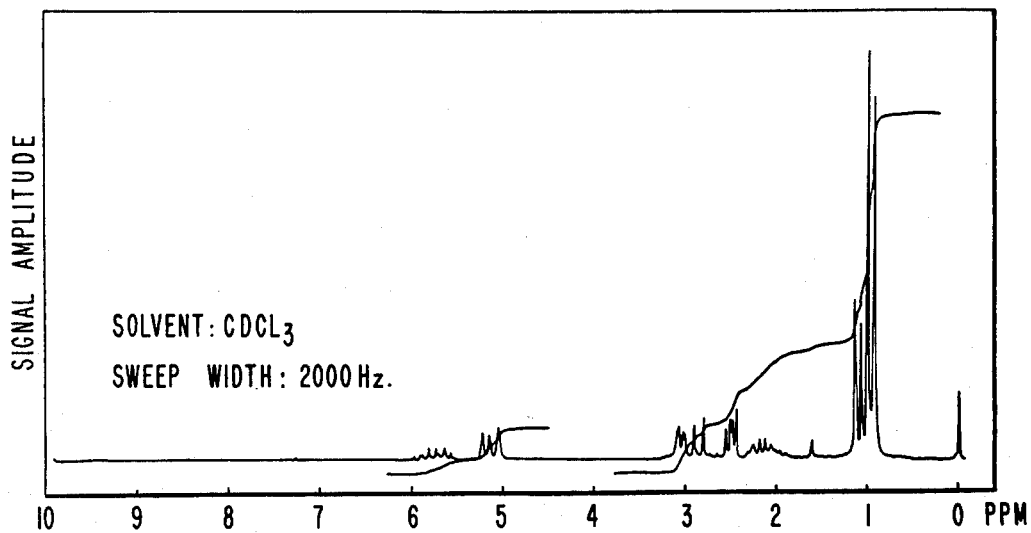
FIG. 11 is the NMR spectrum for the product of Example II(E) wherein 3-allylthio-2,6-dimethyl-4-heptanone is produced.
Figure 12:
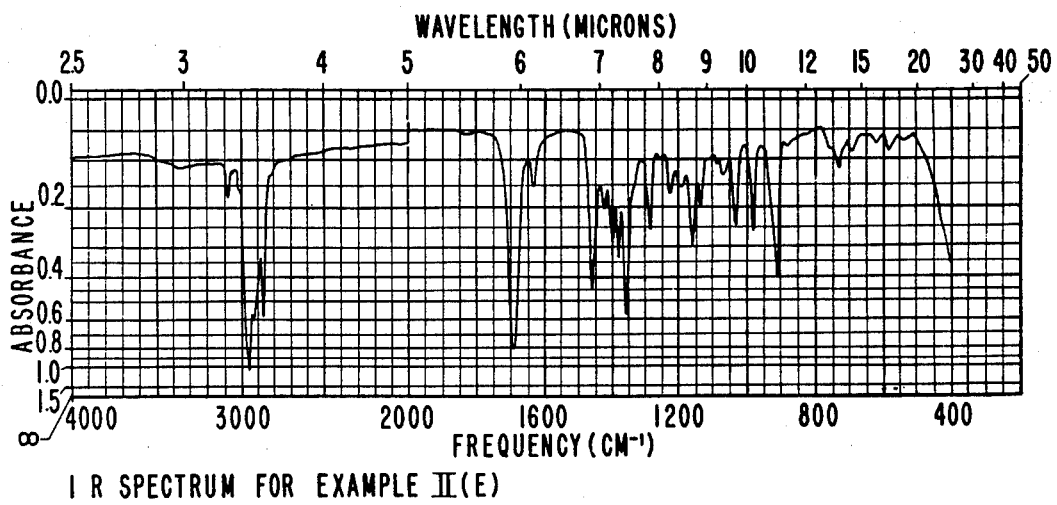
FIG. 12 is the IR spectrum for the product of Example II(E) wherein 3-allylthio-2,6-dimethyl-4-heptanone is produced.

The NMR spectrum is illustrated in FIG. 11. The infrared spectrum is illustrated in FIG. 12.

The mass spectral analysis is as follows:

| m/e | Relative Intensity |
|---|---|
| 41 | 33[5] |
| 55 | 24 |
| 57 | 32[6] |
| 69 | 18 |
| 73 | 40[3] |
| 85 | 30 |
| 87 | 43[2] |
| 95 | 30 |
| 129 | 100[1] |
| 142 | 38[4] |
| M 214 | 17 |

The NMR analysis is as follows:

| | | | |
|---|---|---|---|
| 0.84 ppm, 1.08 | (doublets) | $CH_3-$ | 12H |
| 2.14 | (m) | methine protons | 2H |
| 2.48 | (m) | $CH_2-C=O$ | 2H |
| 2.84 | (d) | $=C-HC-S-$ | 1H |
| 3.04 | (m) | $=C-CH_2-S-$ | 2H |
| 5.22–5.04 | (m) | $C=C\begin{smallmatrix}H\\H\end{smallmatrix}$ | 2H |
| 5.96–5.56 | (m) | $HC=C-$ | 1H |

The IR analysis is as follows: 914 cm$^{-1}$, 980, 1035, 1160, 1360, 1380, 1465, 1695, 2870, 2930, 2960.

EXAMPLE II

F. PREPARATION OF (1,3-DIETHYL ACETONYL)(1,3-DIISOPROPYLACETONYL) SULFIDE

Reaction:

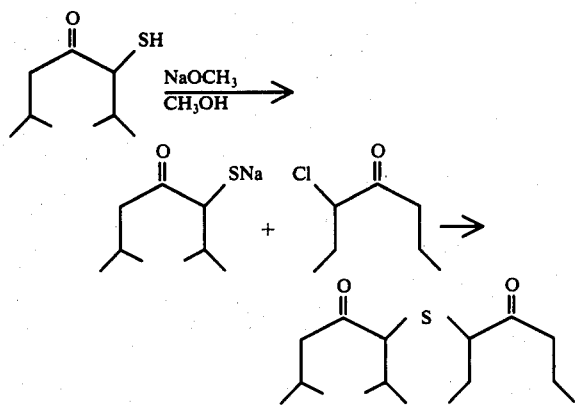

Into a 50 ml, round bottom, three-necked flask equipped with magnetic stirrer, pot thermometer, Y tube, nitrogen inlet tube, reflux condenser with cotton plug, and water bath is placed a solution of 0.65 grams (0.012 moles) of sodium methoxide dissolved in 10 ml anhydrous methanol. While maintaining the temperature of the reaction mass at 24°–27° C, a solution of 2.1 grams of 3-mercapto-2,6-dimethyl-4-heptanone dissolved in 12 ml anhydrous methanol is added to the sodium methoxide solution. 1.78 grams of 3-chloro-4-heptanone is then added to the reaction mass with stirring over a period of 2 minutes, the reaction mass temperature rising to 38° C. Two ml anhydrous methanol used as rinse is then added to the reaction mass, and with stirring the reaction mass temperature cools to 25° C. The reaction mass is continued to be stirred at 25° C for a period of 5 hours. At this point 25 ml distilled water is added, and the resulting solid dissolves. The oil phase is extracted with three 15 ml portions of methylene chloride, and the extracts are combined and washed with one 10 ml portion of water. The extracts are then dried over anhyrous sodium sulfate and gravity filtered and concentrated on a rotary evaporator using water aspirator vacuum to a weight of 3.20 grams (yellow oil). GLC analysis (8 feet × ¼ inch SE-30 column), NMR, IR and mass spectral analyses of GLC isolated material yield the information that the resulting product is 85% pure and has the structure:

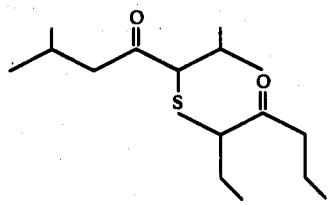

Figure 13:
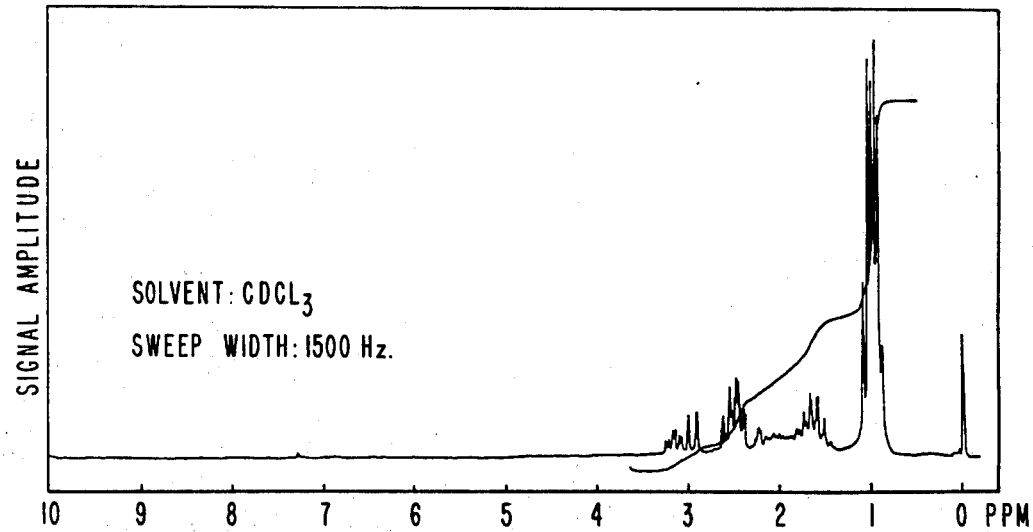
FIG. 13 is the NMR spectrum for the product of Example II(F) wherein (1,3-diethylacetonyl) (1,3-diisopropylacetonyl) sulfide is produced.
Figure 14:
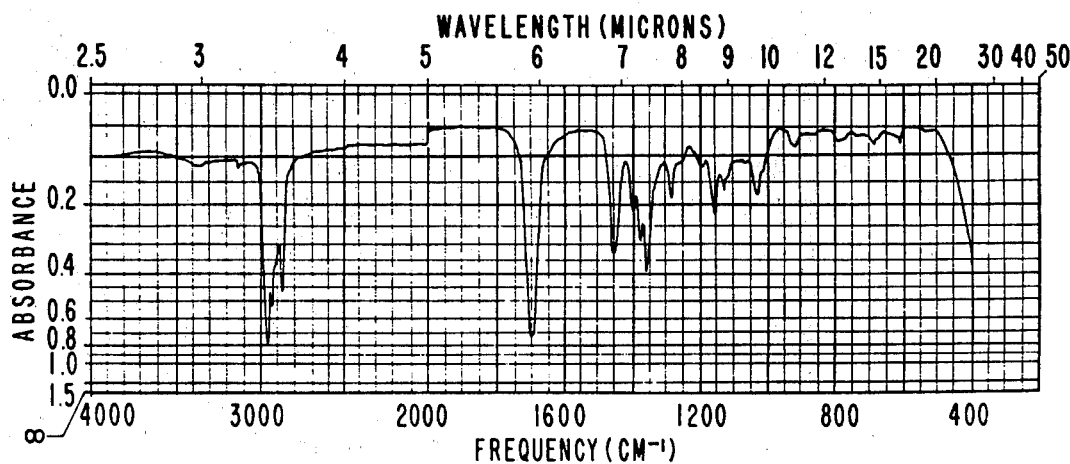
FIG. 14 is the IR spectrum for the product of Example II(F) wherein (1,3-diethylacetonyl) (1,3-diisoproylacetonyl)sulfide is produced.
Figure 14:
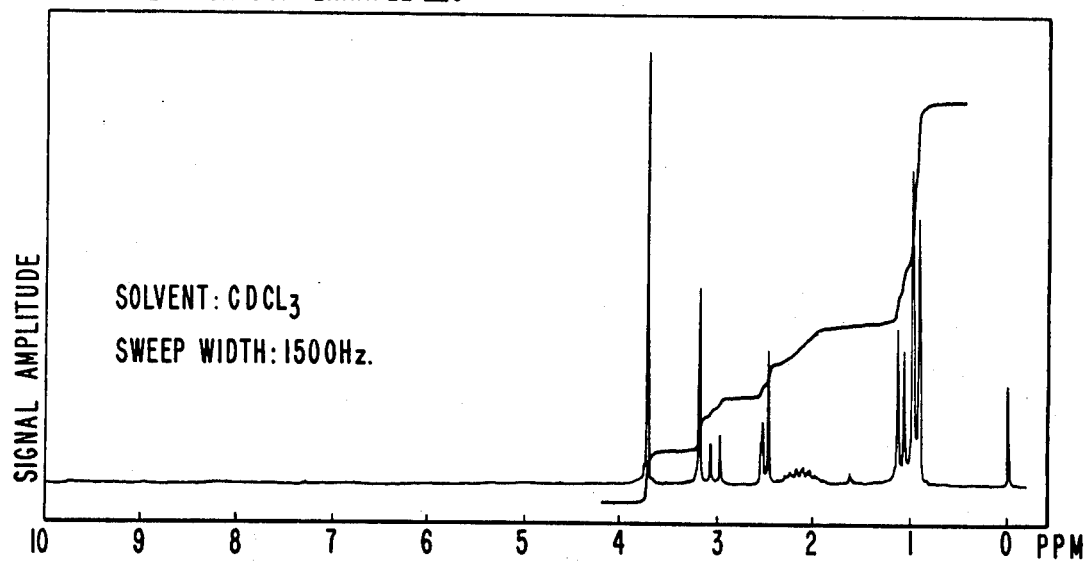
Figure 14:
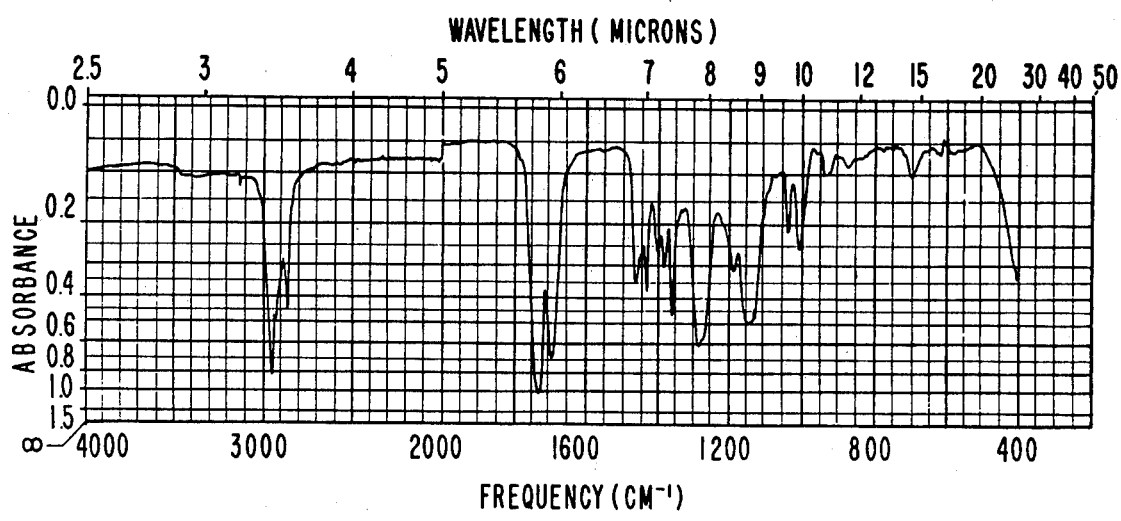

The NMR spectrum is set forth in FIG. 13. The IR spectrum is set forth in FIG. 14.

The mass spectral analysis is as follows:

| m/e | Relative Intensity |
|---|---|
| 41 | 50[6] |
| 43 | 82[3] |
| 55 | 33 |
| 57 | 89[2] |
| 71 | 56[5] |
| 85 | 100[1] |
| 114 | 67[4] |
| 145 | 39 |
| 201 | 36 |

-continued

| m/e | Relative Intensity |
|---|---|
| M 286 | 29 |

The NMR analysis is as follows:

| | | |
|---|---|---|
| 1.07 ppm, 0.86 | $CH_3-$ | 18H |
| 1.62 | $-CH_2-$ + methine protons | 6H |
| 2.46 | $-CH_2-C=O$ | 4H |
| 3.15 and 2.96 | $\overset{O}{\underset{\|}{C}}-HC-S-$ | 2H |

The IR-analysis is as follows: 1155 cm$^{-1}$, 1360, 1380, 1460, 1700, 2870, 2930, 2960.

EXAMPLE II

G. PREPARATION OF 3-[(METHOXYCARBONYL)METHYLTHIO]-2,6-DIMETHYL-4-HEPTANONE

Reaction:

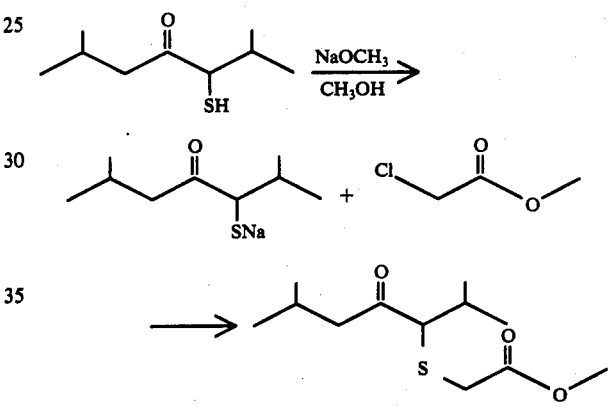

Into a 50 ml, round-bottom, three-necked flask equipped with magnetic stirrer, pot thermometer, Y tube, nitrogen inlet tube, reflux condenser with cotton plug, H$_2$SO$_4$ bubbler for nitrogen, and cold water bath is added a solution of 0.65 grams of sodium methoxide dissolved in 10 ml anhydrous methanol. At a reaction mass temperature of 25°–28° C and over a period of one minute, while stirring, is added a solution of 2.1 grams of 3-mercapto-2,6-dimethyl-4-heptanone dissolved in 2 ml anhydrous methanol. After stirring 8 minutes, 1.30 grams of methylchloroacetate (0.012 moles) is added over a period of 2 minutes to the reaction mass; the temperature of the reaction mass rising to 38° C. The reaction mass is allowed to cool to 24° C and is stirred for a period of 2 hours.

Distilled water (25 ml) is then added to the reaction mass whereupon the solid present dissolves. The organic phase is then extracted with three 15 ml methylene chloride portions. The combined extracts are washed with one 10 ml portion of water and dried over anhydrous sodium sulfate and gravity filtered. The filtered extracts are then concentrated on a rotary evaporator using water aspirator vacuum to a weight of 2.67 grams (pale yellow oil). GLC trapping of the major component (Conditions: 8 feet × ¼ inch SE-30 column), with mass spectral, IR and NMR analyses confirm that the resulting product has the structure:

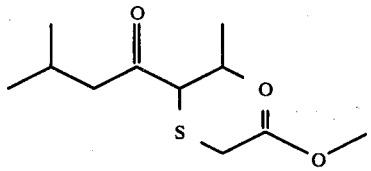

The NMR spectrum is set forth in FIG. 14(A). The IR spectrum is set forth in FIG. 14(B). The mass spectral analysis is as follows:

| m/e | Relative Intensity |
|---|---|
| 29 | 11 |
| 41 | 24[6] |
| 43 | 12 |
| 55 | 24 |
| 57 | 53[3] |
| 85 | 46[4] |
| 101 | 100[1] |
| 129 | 32[5] |
| 161 | 75[2] |
| M 246 | 21 |

The NMR analysis is as follows:

| 0.94, 1.10 ppm | $CH_3-\overset{H}{\underset{\phantom{C}}{C}}-$ | 12 H |
|---|---|---|
| 2.12 | $\overset{Me}{\underset{Me}{\diagdown}}\overset{H}{\underset{\phantom{C}}{C}}-$ | 2 H |
| 2.50 | $-CH_2-\overset{O}{\overset{\|}{C}}-$ | 2 H |
| 3.03 | $-S-\overset{H}{\underset{\phantom{C}}{C}}-\overset{O}{\overset{\|}{C}}-$ | 1 H |
| 3.19 | $-S-CH_2-\overset{O}{\overset{\|}{C}}-O-$ | 2 H |
| 3.70 | $CH_3-O-\overset{O}{\overset{\|}{C}}-$ | 3 H |

The IR analysis is as follows: 1145 cm$^{-1}$, 1185, 1285, 1360, 1375, 1430, 1460, 1695, 1735, 2860, 2920, 2960.

EXAMPLE II (H) PREPARATION OF 3-[(METHOXYCARBONYL)METHYLTHIO]-4-HEPTANONE

Reaction:

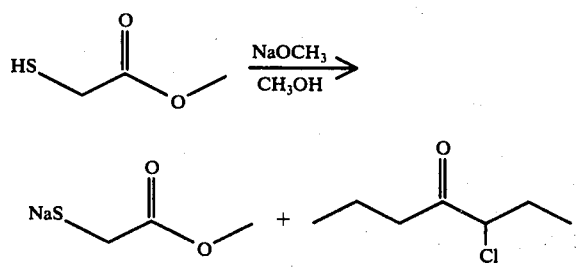

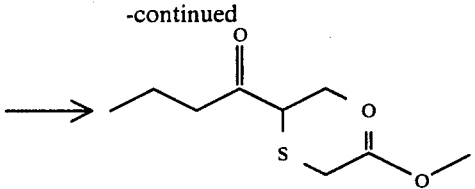

Into a 50 ml, three-necked, round-bottom flask equipped with magnetic stirrer, pot thermometer, Y tube, nitrogen inlet tube, reflux condenser with cotton plug and cold water bath is placed a solution of 1.08 grams of sodium methoxide dissolved in 11 ml anhydrous methanol (0.02 moles sodium methoxide). Over a period of 2 minutes, and at a temperature of 25°-30° C, 2.12 grams (0.02 moles) of methyl thioglycolate dissolved in 2 ml anhydrous methanol is added to the reaction mass with stirring. After 5 minutes, 2.97 grams of 3-chloro-4-heptanone is then added to the reaction mass with stirring while the temperature of the reaction mass warms to 40° C. The reaction mass then cools to 35° C and is stirred in the temperature range of 25°-35° C for a period of 2½ hours.

25 ml water is then added to the reaction mass with stirring, and the solid present therein dissolves (pH = 6–7). The reaction mass is extracted with three 20 ml volumes of methylene chloride, and the methylene chloride extracts are combined and washed with one 10 ml portion of water. The methylene chloride extracts are then dried over anhydrous sodium sulfate, gravity filtered and concentrated on a rotary evaporator using water aspirator vacuum to a weight of 3.77 grams (light yellwo oil). GLC analysis (Conditions: 8 feet × ¼ inch SE-30 column) indicates 92.0% product. NMR, mass spectral and IR analyses of GLC isolated material confirm that the resulting product is:

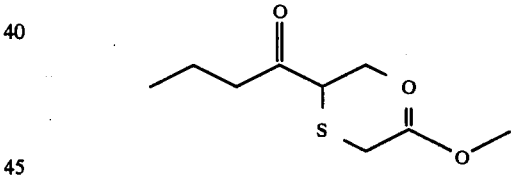

The mass spectral analysis is as follows:

| m/e | Relative Intensity |
|---|---|
| 27 | 11 |
| 41 | 21 |
| 43 | 54[4] |
| 45 | 12 |
| 55 | 11 |
| 71 | 59[3] |
| 87 | 100[1] |
| 115 | 41[5] |
| 147 | 90[2] |
| M 218 | 35[6] |

The NMR analysis is as follows:

| 0.98 ppm | methyl protons | 6H |
|---|---|---|
| 2.06–1.46 | $-CH_2-$ | 4H |
| 2.60 | $-CH_2-C=O$ | 2H |
| 3.22 | $-S-CH_2-C=O$ | 3H |
| 3.30 | $O=C-HC-S$ | |

| | | |
|---|---|---|
| 3.72 | ![CH3-O-C(=O)-] CH₃—O—C(=O)— | 3H |

The IR analysis is as follows: 1000 cm⁻¹, 1150, 1185, 1275, 1430, 1450, 1695, 1730, 2860, 2920, 2960.

Figure 15:
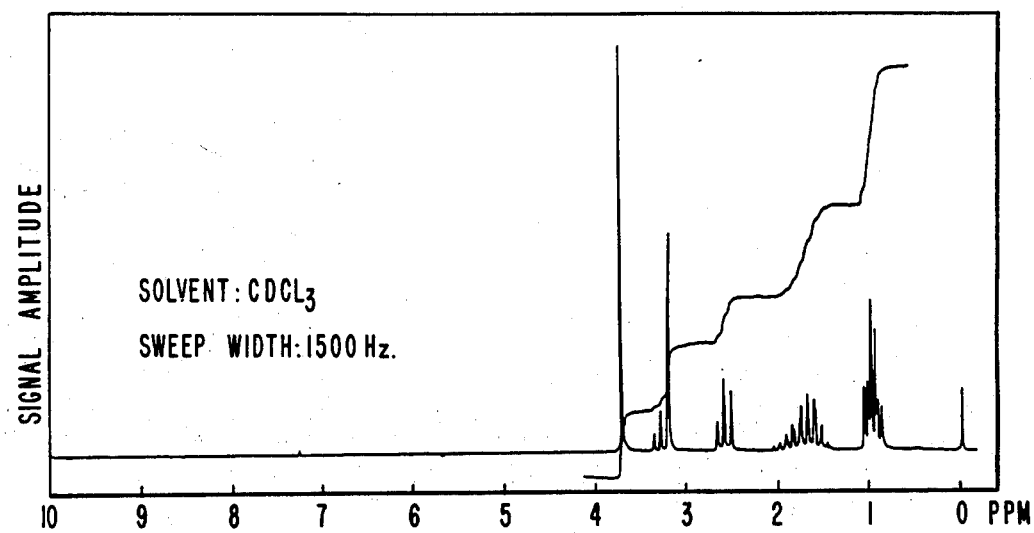
FIG. 15 is the NMR spectrum for the product of Example II(H) wherein 3-[(methoxycarbonyl)methylthiol]-4-heptanone is produced.
Figure 16:
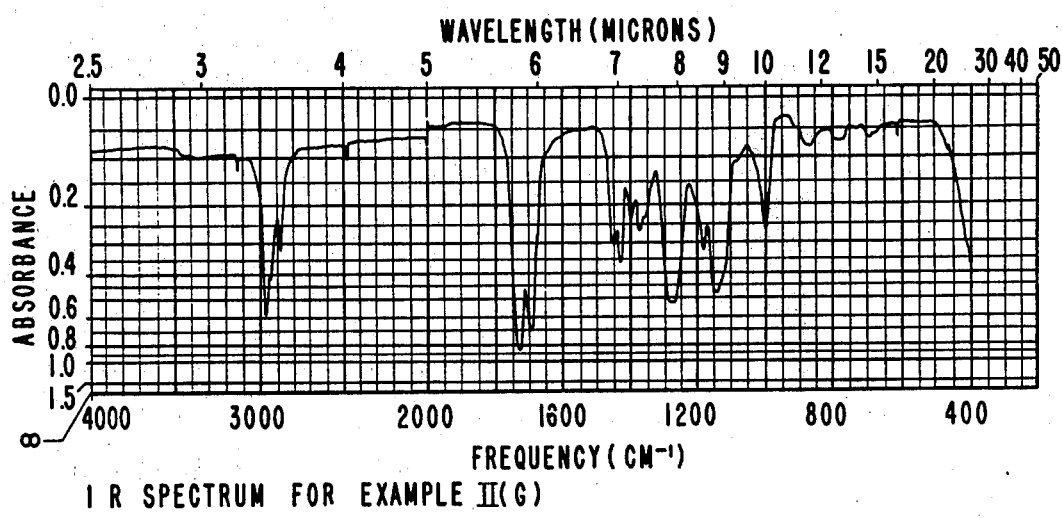
FIG. 16 is the IR spectrum for the product of Example II(H) wherein 3-[(methoxycarbonyl)methylthio]-4-1-heptanone is produced.

The NMR spectrum is set forth in FIG. 15. The infrared spectrum is set forth in FIG. 16.

EXAMPLE II

(I) PREPARATION OF 3-THIOACETYL-2,6-DIMETHYL-4-HEPTANONE

Reaction:

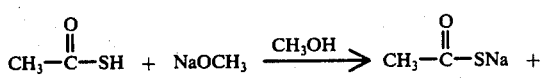

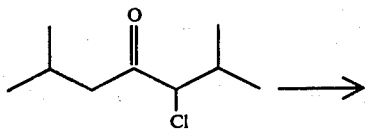

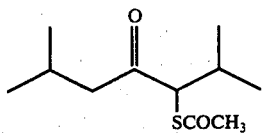

Into a 25 ml, three-necked, round-bottom flask equipped with magnetic stirrer, nitrogen inlet tube at top of 6 inches Vigreux column, reflux condenser with cotton plug, pot thermometer, water both and heating mantle is placed a solution containing 0.27 grams of sodium methoxide (0.005 moles) in 3 ml anhydrous methanol. To the sodium methoxide solution is added a solution of 0.38 grams (0.005 moles) of thioacetic acid in 3 ml anhydrous methanol, with stirring, while maintaining the reaction mass temperature in the range of 23°–25° C. The addition takes place over a period of 10 minutes. While maintaining the reaction mass temperature at 23° C, a solution of 0.883 grams (0.005 moles) of 3-chloro-2,6-dimethyl-4-heptanone (prepared according to Part A) in 2 ml anhydrous methanol is added to the reaction mass. While maintaining the reaction mass temperature between 35° and 45° C and over a period of 3 hours, the reaction mass is stirred. At the end of the 3-hour period only 6% of product is formed. The reaction mass is then refluxed at 66°–76° C for a period of 12 hours, at which point it is indicated by GLC, NMR, IR and mass spectral analyses that 3-thioacetyl-2,6-dimethyl-4-heptanone is formed in an amount of 65%.

The reaction mass is then concentrated on a rotary evaporator using water aspirator vacuum to 4 ml of an oily product. Ten ml water is then added, and the solid dissolves. The oil layer is extracted with three 8 ml portions of methylene chloride, and the extracts are combined and washed with one 8 ml water portion. The extracts are then dried over anhydrous sodium sulfate, gravity filtered and concentrated yielding 0.54 grams of a yellow oil. The desired product is trapped on a GLC SE-30 column (Conditions: 8 feet × ¼ inch).

The NMR analysis is as follows:

| | | |
|---|---|---|
| 1.01–0.88 ppm | Methyl protons | 12H |
| 2.42–2.03 | Methine protons | |
| 2.44 | CH₂—C(=O)— | |
| 2.40 | CH₃—C(=O)—S— | 7H |
| 4.14 | —C(=O)—C(H)—S—C(=O)— | |

The infrared analysis is as follows: 6.20 cm⁻¹, 950, 1100, 1130, 1360, 1380, 1465, 1695, 2870, 2930, 2960.

The mass spectral analysis is as follows:

| m/e | Relative Intensity |
|---|---|
| 41 | 14[5] |
| 43 | 40[3] |
| 55 | 12 |
| 57 | 60[2] |
| 85 | 100[1] |
| 89 | 27[4] |
| 131 | 12[6] |
| 141 | 9 |
| 173 | 11 |
| M 216 | 7 |

Figure 16A:
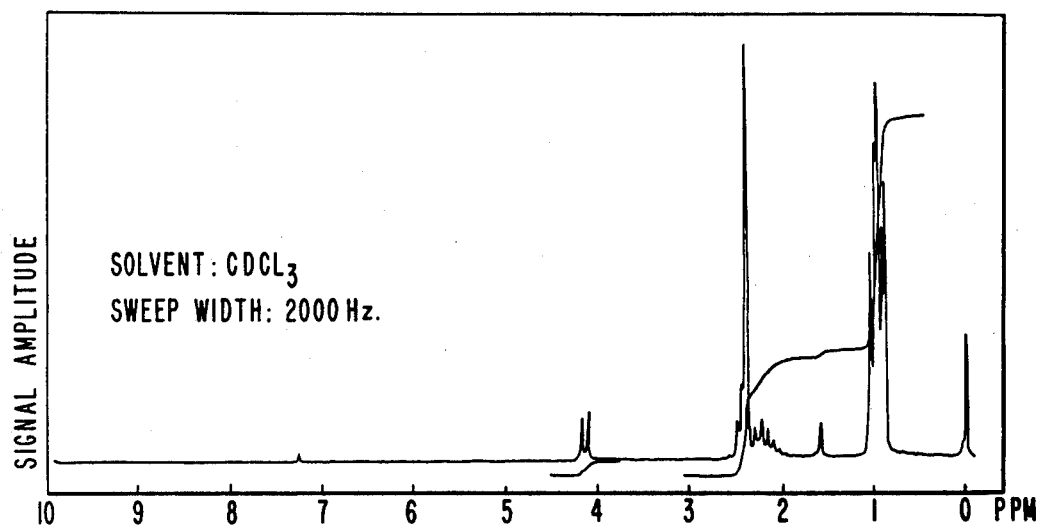
FIG. 16(A) is the NMR spectrum for the product of Example II(I) wherein 3-thioacetyl-2,6-dimethyl-4-heptanone is produced.
Figure 16B:
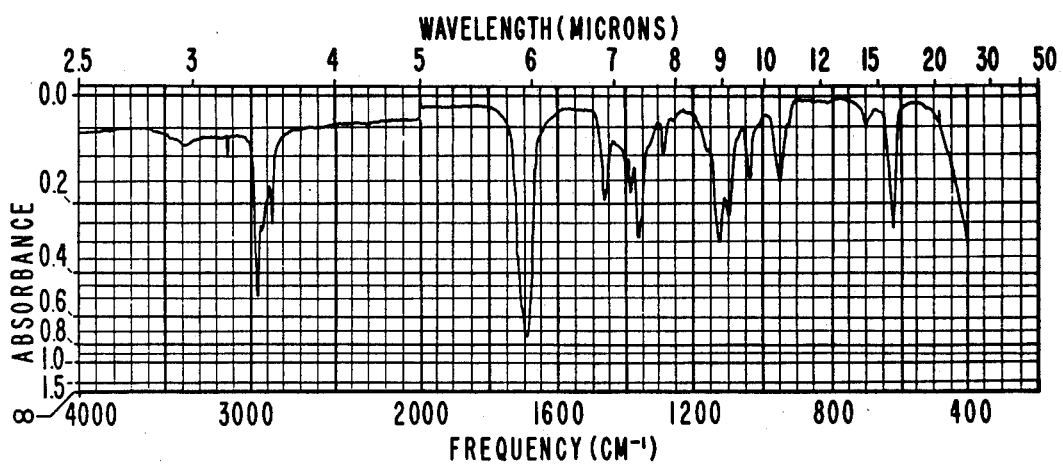
FIG. 16(B) is the IR spectrum for the product of Example II(I) wherein 3-thioacetyl-2,6-dimethyl-4-heptanone is produced.

The NMR spectrum is set forth in FIG. 16(A). The infrared spectrum is set forth in FIG. 16(B).

EXAMPLE III

A. Preparation of 3-propylthio-4-heptanone

Reaction:

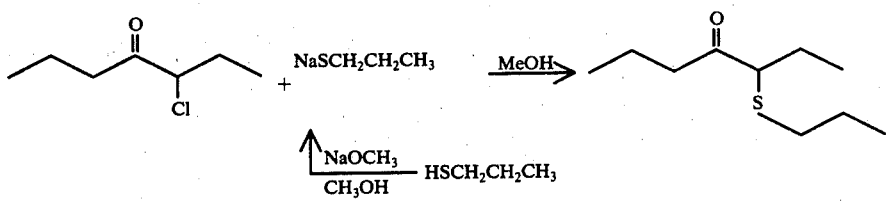

Into a 50 ml, three-necked, round bottom flask equipped with magnetic stirrer, reflux condenser, nitrogen inlet tube, pot thermometer and cold water bath, is placed a solution of 0.54 grams of sodium methoxide dissolved in 6 ml anhydrous methanol (0.01 moles of sodium methoxide). The sodium methoxide solution is cooled using the water bath to 25° C. A solution of 0.76 grams of n-propyl mercaptan dissolved in 6 ml anhydrous methanol (0.01 moles n-propyl mercaptan) is then added to the sodium methoxide/methanol solution, and the temperature rises to 28° C. 1.5 g (0.01 moles) 3-chloro-4-heptanone dissolved in 2 ml anhydrous methanol is then added, and the temperature of the reaction mass rises to 38° C, whereupon it is cooled using the water bath to a temperature in the range of 25°–30° C. The reaction mass is then stirred under nitrogen for a period of 6 hours.

The reaction mass is then concentrated to a volume of 4 ml using a rotary evaporator to which water aspirator vacuum is applied. 9 ml distilled water is then added to the reaction mass concentrate whereupon the solid dissolves. The oil phase is extracted with three 8 ml portions of methylene chloride, and the extracts are combined and washed with 8 ml of water and dried over anhydrous sodium sulfate and filtered and then concentrated. GLC MS, NMR and IR analyses of trapped product yield the information that the subject material is 3-propylthio-4-heptanone.

Figure 17:
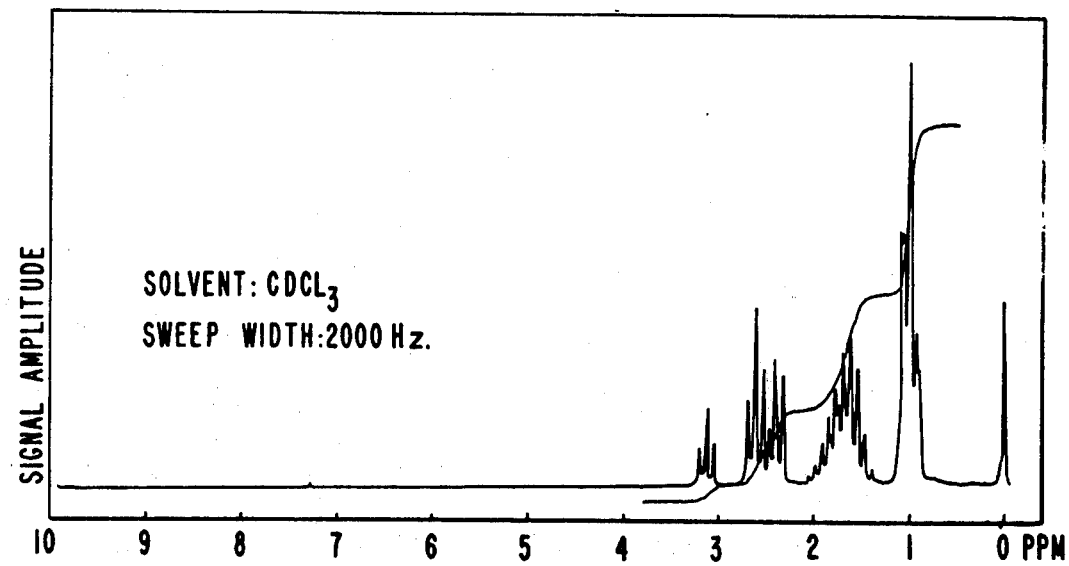
FIG. 17 is the NMR spectrum for the product of Example III(A) wherein 3-propylthio-4-heptanone is produced.
Figure 18:
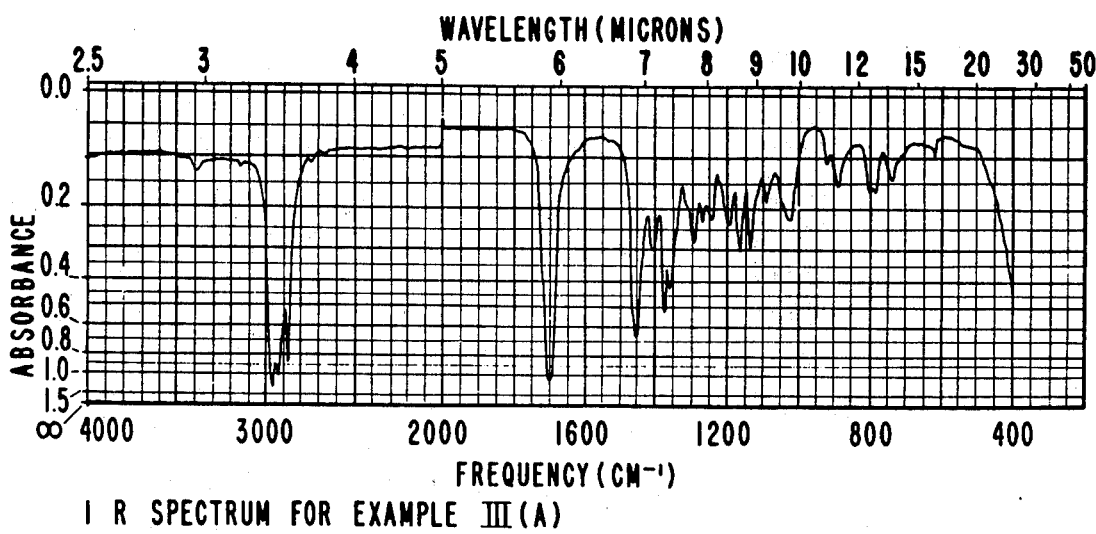
FIG. 18 is the IR spectrum for the product of Example III(A) wherein 3-propylthio-4-heptanone is produced.

The NMR spectrum is set forth in FIG. 17. The IR spectrum is set forth in FIG. 18.

The NMR analysis is as follows:

| 0.87 – 1.04 ppm | superimposed signals | $CH_3-$ | 9H |
|---|---|---|---|
| 1.63 | (m) | $-CH_2-$ | 6H |
| 2.38 | (t) | $-CH_2-S-$ | 2H |
| 2.60 | (t) | $CH_2-\overset{\overset{O}{\|}}{C}-$ | 2H |
| 3.11 | (t) | $O=C-HC-S-$ | 1H |

The IR analysis is as follows: 1130 cm$^{-1}$, 1165, 1290, 1360, 1380, 1405, 1460, 1700, 2880, 2940, 2960

The mass spectral analyses is as follows:

| m/e | Relative Intensity |
|---|---|
| 41 | 20[4] |
| 43 | 26[3] |
| 55 | 5 |
| 71 | 10 |
| 75 | 35[2] |
| 114 | 10 |
| 117 | 100[1] |
| 118 | 10[6] |
| 119 | 9 |
| M 188 | 16[5] |

Material prepared similarly to above example was vacuum distilled yielding 98.4% pure product (boiling point 72°–73° C at 1.5 mm Hg). The thus-distilled material has the same physical properties as set forth above for 3-propylthio-4-heptanone.

B. Preparation of 3-propylthio-4-heptanol

Reaction:

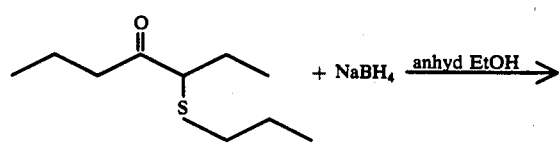

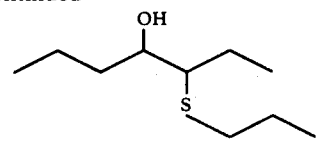

Into a 25 ml, three-necked, round bottom flask equipped with magnetic stirrer, reflux condenser, pot thermometer, and nitrogen inlet (for flushing with dry nitrogen) is added a solution of 0.15 grams of sodium borohydride dissolved in 6 ml anhydrous methanol (0.004 moles sodium borohydride). With stirring, a solution of 1.0 grams of 3-propylthio-4-heptanone dissolved in 4 ml anhydrous ethyl alcohol is added to the sodium borohydride solution which then warms to 28° C. The reaction mass is stirred for a period of 2 hours at 25° C and then concentrated on a rotary evaporator (using water aspirator vacuum) to a volume of 4 ml yielding an oily solid. 8 ml water is then added to the solid, with stirring, and the solid dissolves yielding two phases: an oil phase and a water phase. The resulting reaction mass is acidified with 10% hydrochloric acid to a pH of between 2 and 3. The oil phase is extracted with three 8 ml volumes of methylene chloride, and the extracts are combined and washed with 8 ml water. The extracts are then dried over anhydrous sodium sulfate, filtered and concentrated to a weight of 0.79 grams (water-white oil). GLC, IR, mass spectral and NMR analyses after GLC trapping (Conditions: 8 feet × ¼ inch SE-30 column) yield the information that the crude material is 96% product having the structure 3-propylthio-4-heptanol.

Figure 19:
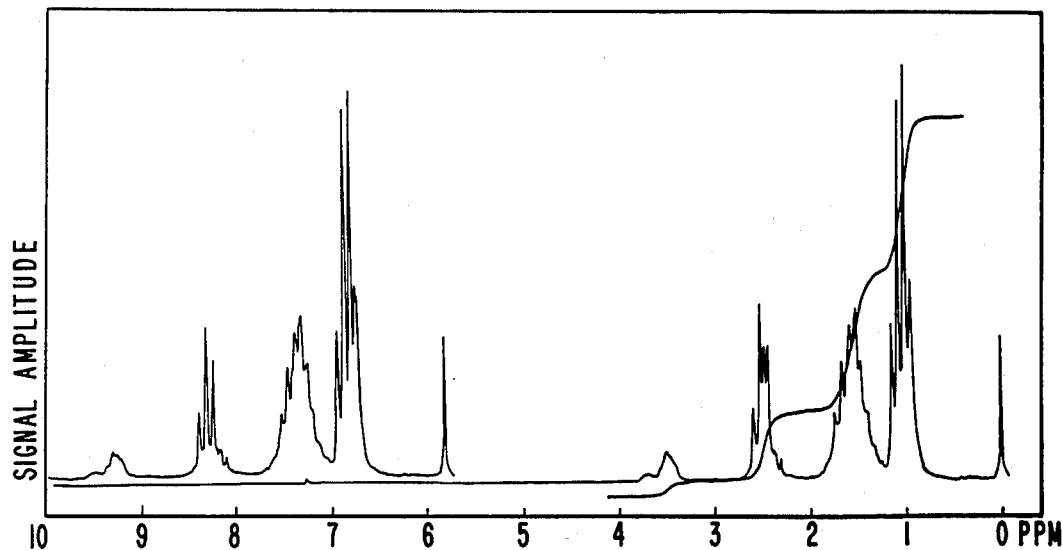
FIG. 19 is the NMR spectrum for the product of Example III(A) wherein 3-propylthio-4-heptanol is produced.
Figure 20:
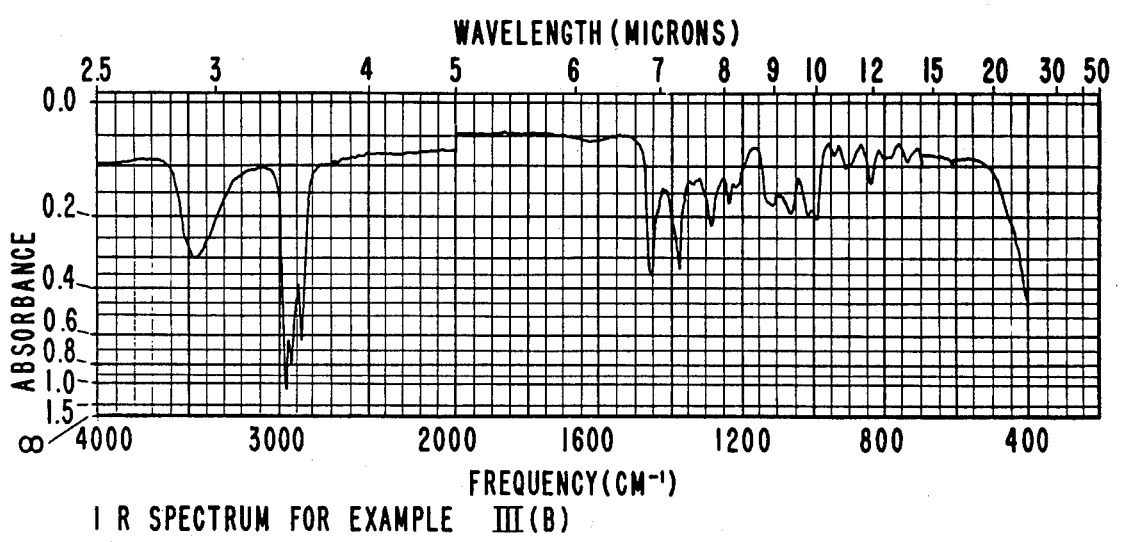
FIG. 20 is the IR spectrum for the product of Example III(A) wherein 3-propylthio-4-heptanol is produced.

The NMR spectrum is set forth in FIG. 19. The IR spectrum is set forth in FIG. 20.

The NMR analysis is as follows:

| 1.13–0.96 ppm | superimposed signals | methyl protons | 9H |
|---|---|---|---|
| 1.44 | (m) | $-CH_2-$ | 8H |
| 2.47 | (s) | $-OH$ | |
| | | | 4H |
| 2.49 | (m) | $HC-S-CH_2-$ | |
| 3.50 | (m) | $HC-O-$ | 1H |

The IR analysis is as follows: 1290 cm$^{-1}$, 1380, 1460, 2880, 2940, 2970, 3460.

Material prepared similarly to above example was vacuum distilled yielding 99.8% pure product (boiling point 65° C at 0.4 mm Hg). The thus-distilled material has the same physical properties as set forth above for 3-propylthio-4-heptanol.

EXAMPLE IV

PREPARATION OF 3-ISOBUTYLTHIO-4-HEPTANONE

Reaction:

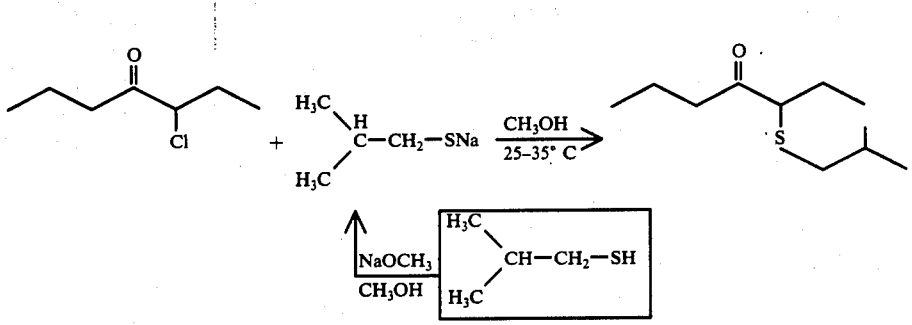

15

Into a 50 ml. three-necked, round bottom flask equipped with magnetic stirrer, reflux condenser, pot thermometer, water bath, 15 cm Vigreux column with nitrogen inlet at top is added a solution of 0.54 grams of sodium methoxide (0.01 moles) in 6 ml anhydrous methanol. The reaction mass is cooled to 25° C and a solution of 0.90 grams of isobutyl mercaptan (2-methyl-1-propanethiol) dissolved in 6 ml anhydrous methanol is added over a period of one minute. After keeping the reaction mass at 24° C with stirring for a period of 10 minutes, 1.50 grams of 3-chloro-4-heptanone dissolved in 2 ml anhydrous methyl alcohol (0.01 moles of 3-chloro-4-heptanone) is added to the reaction mass which then warms to 37° C. The reaction mass is allowed to cool to a temperature of 24° C and stirred at that temperature for a period of 6 hours.

The reaction mass is then concentrated on a rotary evaporator using water aspirator vacuum to a volume of 4 ml yielding an oily solid. Ten ml water is then added, and the solid dissolves yielding two phases: an oil phase and an aqueous phase. Then oil phase is extracted with three 9 ml portions of methylene chloride, and the extracts are combined and washed with 9 ml water. The extracts are then dried over anhydrous sodium sulfate, filtered and concentrated to a weight of 1.78 grams.

Mass spectral, infrared, NMR and IR analyses yield the information that the reaction mass contains 90.9% product which is 3-isobutylthio-4-heptanone.

Figure 21:
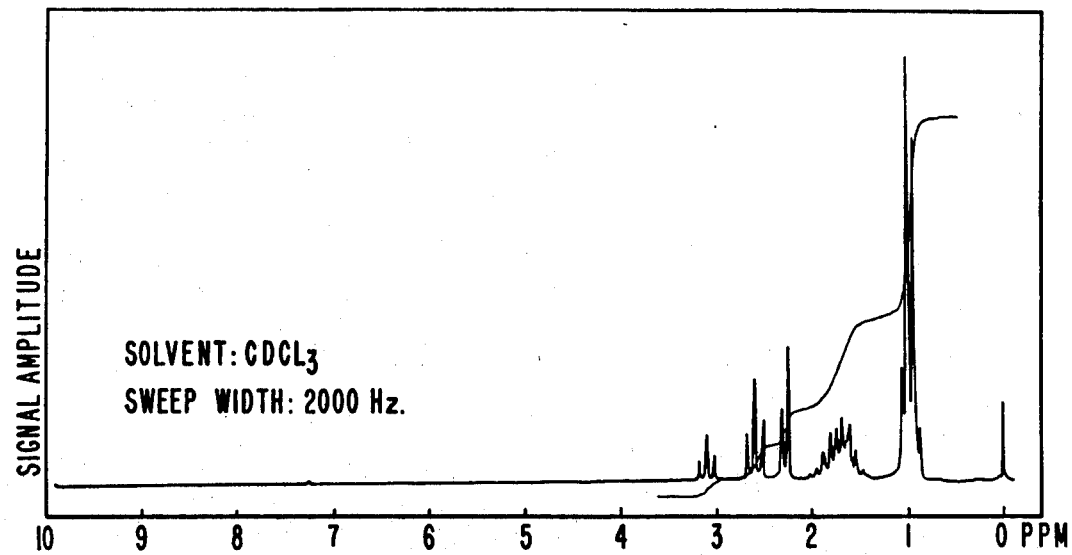
FIG. 21 is the NMR spectrum for the product of Example IV wherein 3-isobutylthio-4-heptanone is produced.
Figure 22:
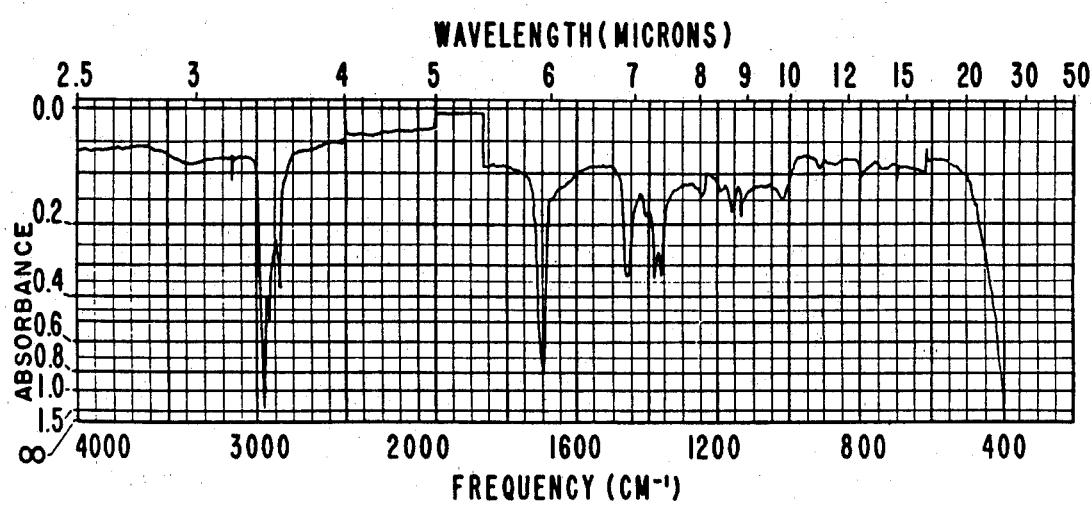
FIG. 22 is the IR spectrum for the product of Example IV wherein 3-isobutylthio-4-heptanone is produced.

The NMR spectrum is set forth in FIG. 21. The IR spectrum is set forth in FIG. 22.

The NMR analysis is as follows:

| 0.96 ppm | (d) | CH₃\H<br>C—<br>CH₃ | 12H |
|---|---|---|---|
| 0.98 | (t) | CH₃—CH₂— | |
| 0.91 | (t) | CH₃—C—C—S—<br>\|<br>C=O | |
| 1.70 | (m) | —CH₂—+ HC—<br>\| | 5H |
| 2.26 | (d) | S—CH₂— | 2H |
| 2.60 | (t) | —CH₂—C—<br>\|\|<br>O | 2H |
| 3.10 | (t) | O=C—HC—S— | 1H |

The IR analysis is as follows: 1365 cm⁻¹, 1380, 1460, 1700, 2880, 2940, 2960.

EXAMPLE V

A. PREPARATION OF 1-CHLORO-1,3-DIPHENYL-2-PROPANONE

Reaction:

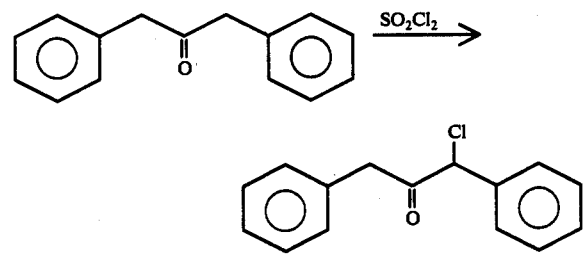

Into a 250 ml, three-necked flask equipped with 15 cm Vigreux column with vacuum outlet at top, pot thermometer, magnetic stirrer, 125 ml addition funnel and cold water bath is placed 99 grams (0.470 moles) of 1,3-diphenylacetone. Over a period of 1½ hours, 21.2 grams (0.157 moles) of SO₂Cl₂ is added while maintaining the reaction temperature in the range of 23°-30° C, and with stirring. At the end of the addition of the SO₂Cl₂, water aspirator vacuum is applied to remove the acidic gases, HCl and SO₂. An additional 21.2 grams of SO₂Cl₂ is then added over a 45 minute period, but allowing the reaction temperature to rise to a maximum of 38° C (without cooling). The reaction mass is then stirred for an additional hour while maintaining the temperature thereof at 24°-38° C and acidic gases are again removed using water aspirator vacuum, over a period of 2 hours. The reaction mass is then transferred to a 250 ml, three-necked, round bottom flask equipped with pot thermometer, nitrogen inlet capillary tube, 1.8 × 30 cm distillation column packed with ¼ inch helices, reflux distillation head, vacuum pump and heating mantle. After 15 minutes of distillation, the packed column was replaced with a 2.8 × 30 cm Vigreux column. Four cuts were removed at a vacuum of 0.2-0.5 mm Hg, and a vapor temperature of 153°-163° C.

Thin layer chromatography was carried out on the fractions since the GLC analysis cannot distinguish between the chlorinated derivative and the starting material. TLC and mass spectral analyses yield the information that the distillate is a mixture of starting material and the desired product, having the structure:

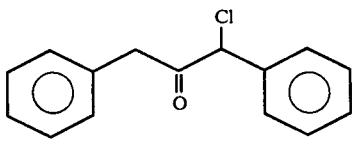

B. PREPARATION OF 1-PROPYLTHIO-1,3-DIPHENYL-2-PROPANONE

Reaction:

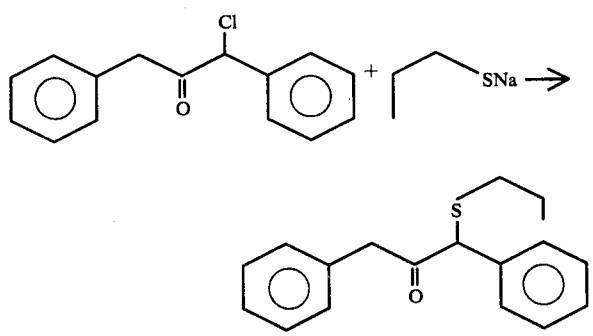

Into a 50 ml, three-necked, round-bottom flask equipped with magnetic stirrer, Y tube, reflux condenser, pot thermometer and nitrogen inlet tube is placed a solution of 0.54 grams sodium methoxide dissolved in 6 ml anhydrous methanol. The reaction mass is cooled and remains at 25° C while a solution of 0.76 grams of n-propylmercaptan (0.01 moles) dissolved in 6 ml anhydrous methanol is added to the sodium methalate solution. A solution of 2.5 grams of the mixture of 1-chloro-1,3-diphenyl-2-propanone and 1,3-diphenyl-2-propanone dissolved in 3 ml anhydrous methanol (prepared according to the procedure of Part A) is added to the reaction mass while allowing the reaction mass to warm to a temperature of 29° C.

The reaction mass is maintained at a temperature of between 25° to 39° C over a period of 4 hours. At the end of the four-hour period the reaction mixture is concentrated on a rotary evaporator using water aspirator vacuum to a slurry which is an amber liquid and a white solid. Ten ml water are added to the mixture in order to dissolve the solid. The organic phase is then extracted with three 8 ml portions of methylene chloride, and the extracts are combined and washed with two 8 ml portions of water. The combined extracts are dried over anhydrous sodium sulfate, gravity filtered and concentrated on a rotary evaporator using water aspirator vacuum to yield an orange amber oil weighing 2.2 grams. GLC analysis (8 feet × ¼ inch SE-30 column) as well as mass spectral, IR, NMR and thin layer chromatography (30% diethyl ether in hexane) analyses confirm that the desired product (isolated by GLC trapping) is 1-propylthio-1,3-diphenyl-2-propanone, having the structure:

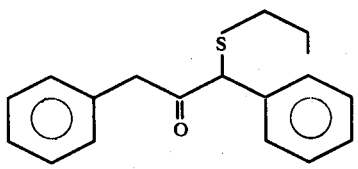

Figure 23:
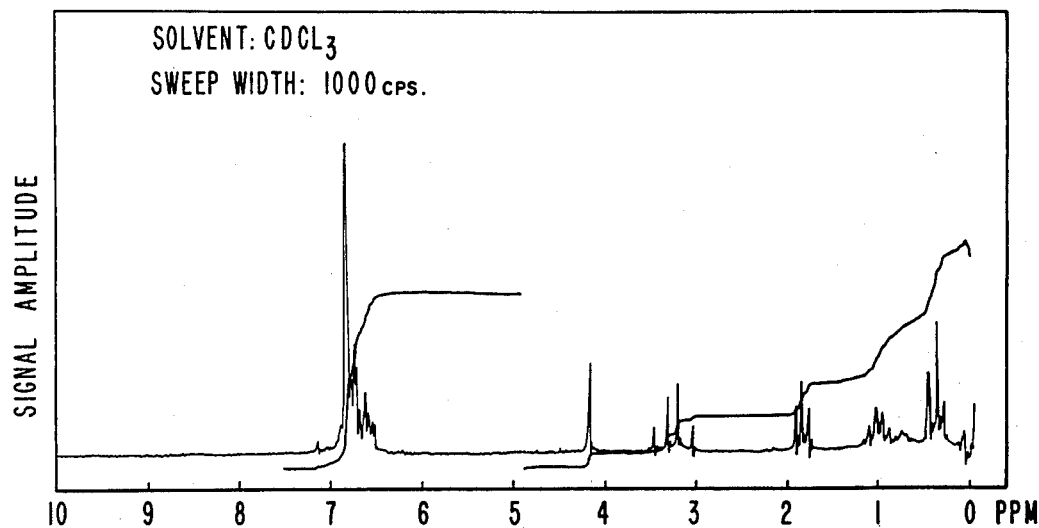
FIG. 23 is the NMR spectrum for the product of Example V(B) wherein 1-propylthio-1,3-diphenyl-2-propanone is produced.
Figure 24:
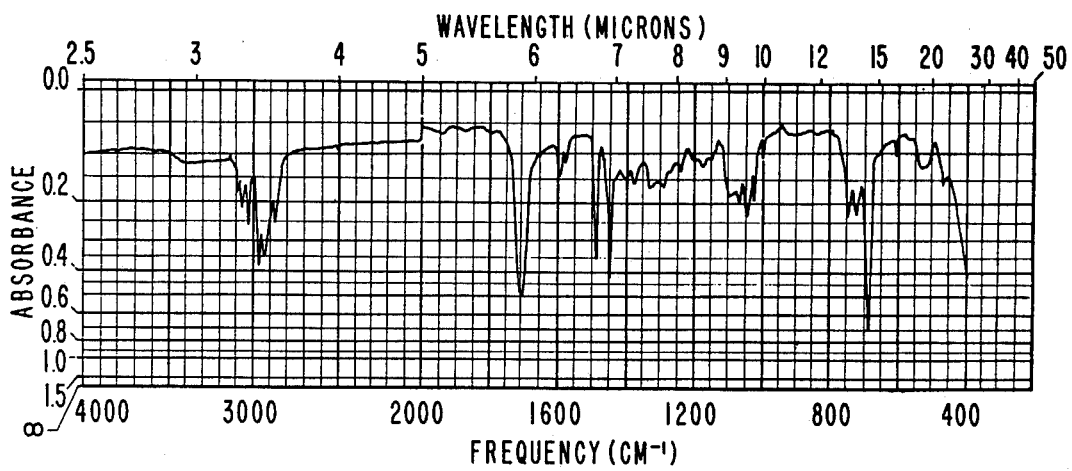
FIG. 24 is the IR spectrum for the product of Example V(B) wherein 1-propylthio-1,3-dipenyl-2-propanone is produced.

The NMR spectrum is set forth in FIG. 23. The IR spectrum is set forth in FIG. 24.

The mass spectral analysis is as follows:

| m/e | Relative Intensity |
|---|---|
| 43 | 8[5] |
| 65 | 7[6] |
| 91 | 47[2] |
| 118 | 6 |
| 123 | 20[3] |
| 165 | 100[1] |
| 166 | 14[4] |
| 167 | 5 |
| 210 | 5 |
| M 284 | 9 |

The NMR analysis is as follows:

| | | | |
|---|---|---|---|
| 0.88 ppm | (t) | $CH_3$— | 3H |
| 1.49 | (m) | —$CH_2$— | 2H |
| 2.34 | (t) | —$CH_2$—S— | 2H |
| 3.76 | (AB) | $\phi$—$CH_2$—$\overset{\overset{O}{\|}}{C}$— | 2H |
| 4.68 | (s) | O=C—HC—$\phi$<br>\|<br>S— | 1H |
| 7.32–7.01 | (m) | aromatic protons | 10H |

The IR analysis is as follows: 690 cm$^{-1}$, 1450, 1490, 1710, 2920, 2960, 3020.

Material prepared similarly to above example was vacuum distilled yielding 98.5% pure product (boiling boint 160°–163° C at 0.4 mm Hg). The thus-distilled material has the same physical properties as set forth above for 1-propylthio-1,3-diphenyl-2-propanone.

EXAMPLE VI

(A) PREPARATION OF 3-METHYLTHIO-2,6-DIMETHYL-4-HEPTANONE

Reaction:

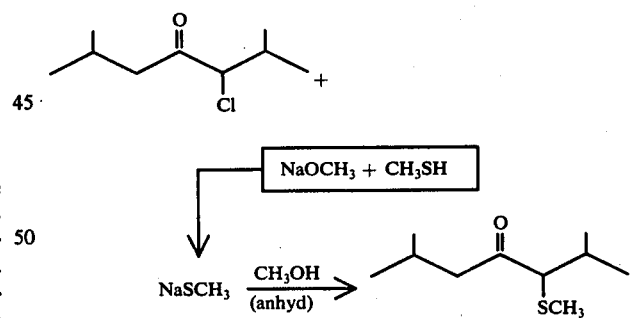

Into a 50 ml, three-necked, round bottom flask equipped with pot thermometer, magnetic stirrer, gas inlet tube (subsurface), gas bubbler, methyl mercaptan gas cylinder, 15 cm Vigreux column, gas outlet tube leading to 10% sodium hydroxide solution, and cold water bath is added a solution of 0.54 grams of sodium methoxide in 12 ml anhydrous methanol (0.01 moles sodium methoxide). The reaction mass warms to 30° C, and it is cooled to 23° C using the cold water bath. Over a period of 20 minutes the methyl mercaptan is bubbled in below the surface of the liquid while maintaining the temperature of the reaction mass at 22°–23° C. The reaction flask is then flushed with dry nitrogen, and a solution of 1.77 grams of 3-chloro-2,6-dimethyl-4-heptanone dissolved in 2 ml anhydrous methanol is then added to the reaction mass. The reaction mass remains at 23°-25° C and is stirred at that temperature for a period of 2.5 hours. GLC analysis indicates 79% product. The reaction mass is then warmed to 35° C and maintained at 28°-35° C for another 1.5 hours.

The reaction mass is then concentrated to a volume of 5 ml using a rotary evaporator to which water aspirator vacuum is applied. 15 ml distilled water is then added to dissolve the solid yielding a two phase mixture (an aqueous phase and an organic phase). The reaction mass is then extracted with three 10 ml portions of methylene chloride, and the extracts are combined and washed with 10 ml of water. The combined extracts are then dried over anhydrous sodium sulfate, gravity filtered and concentrated on a rotary evaporator to a weight of 1.56 grams. GLC, MS, NMR and IR analyses yield the information that the resulting material is 89.6% product, 3-methylthio-2,6-dimethyl-4-heptanone. The pure material is trapped out using preparative GLC (conditions: 8 feet × ¼ inch SE-30 column).

Figure 25:
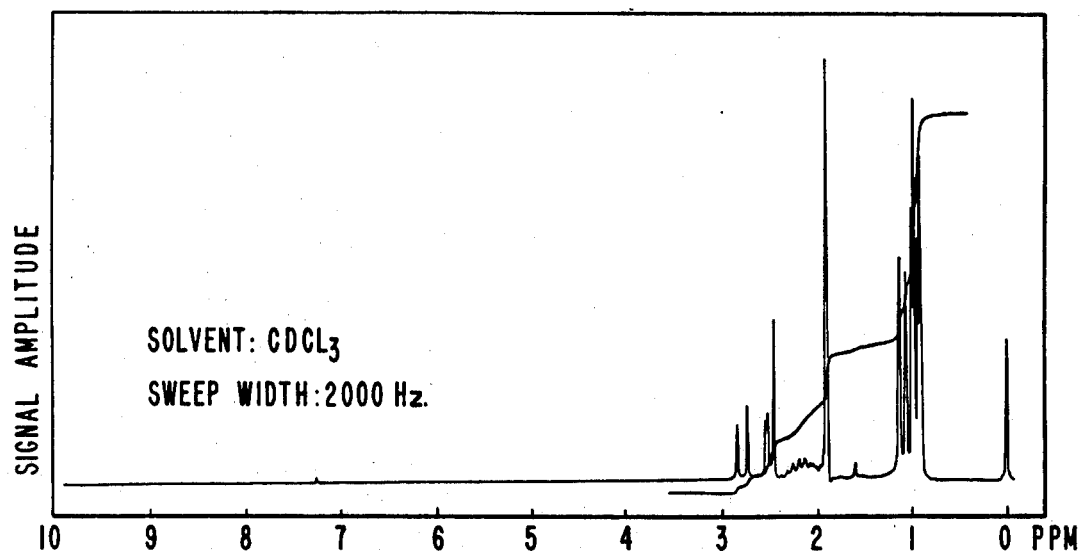
FIG. 25 is the NMR spectrum for the product of Example VI(A) wherein 3-methylthio-2,6-dimethyl-4-heptanone is produced.
Figure 26:
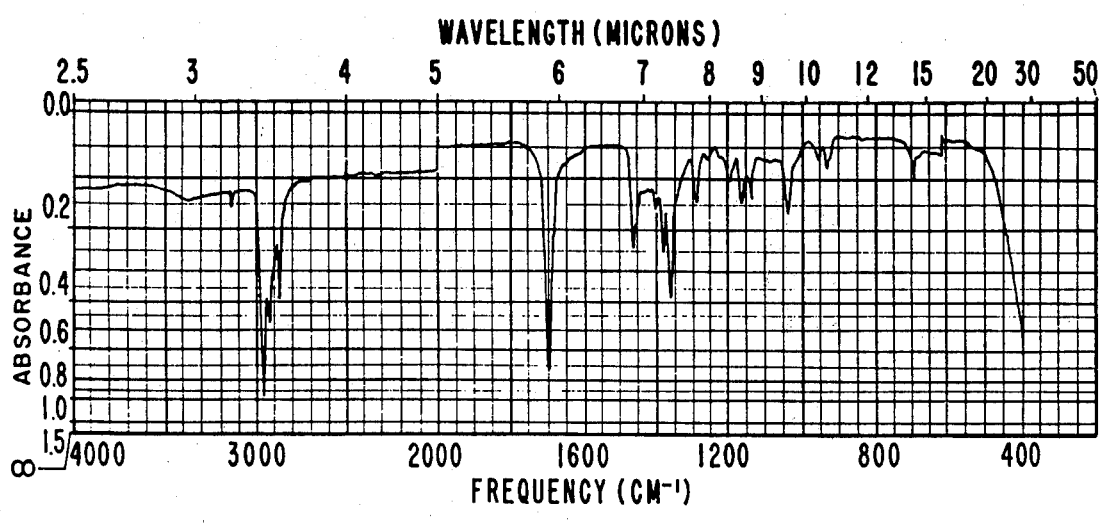
FIG. 26 is the IR spectrum for the product of Example VI(A) wherein 3-methylthio-2,6-dimethyl-4-heptanone is produced.

The NMR spectrum is set forth in FIG. 25. The IR spectrum is set forth in FIG. 26.

The mass spectral analysis is as follows:

| m/e | Relative Intensity |
|---|---|
| 41 | 8[5] |
| 55 | 32[2] |
| 57 | 12[3] |
| 61 | 5 |
| 69 | 5 |
| 85 | 7[6] |
| 102 | 6 |
| 103 | 100[1] |
| 104 | 6 |
| M 188 | 10[4] |

The NMR analysis is as follows:

| 0.94, 1.08 ppm | Methyl protons | 12 H |
|---|---|---|
| 1.90 | $CH_3-S-$ | 3 H |
| 2.37 - 1.96 | Methine protons | 2 H |
| 2.49 | $CH_2-\overset{O}{\underset{\|}{C}}-$ | 2 H |
| 2.78 | $\underset{\|}{HC}-S$ $-C=O$ | 1 H |

The IR analysis is as follows: 1035 cm⁻¹, 1160, 1360, 1380, 1400, 1465, 1695, 2870, 2920, 2960

B. PREPARATION OF 3-METHYLTHIO-2,6-DIMETHYL-4-HEPTANOL

Reaction:

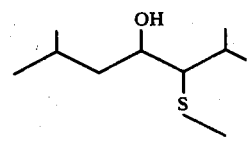

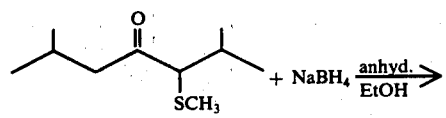

Into a 25 ml, three-necked, round bottom flask equipped with magnetic stirrer, reflux condenser, pot thermometer, warm water bath, nitrogen inlet (to flush with dry nitrogen) is placed a solution of 0.10 grams (0.00265 moles) of sodium borohydride dissolved in 4 ml anhydrous ethanol. Over a period of 1 minute with stirring, at 23° C, a solution of 0.9 grams of 3-thiomethyl-2,6-dimethyl-4-heptanone in 4 ml anhydrous ethanol (prepared according to Part A) is added to the reaction mass. The reaction mass remains at 23° C for a period of one hour, and then is warmed to a temperature of 31° C and maintained at 24°-31° C for a period of 25 hours, after which time 0.2 grams additional sodium borohydride dissolved in 6 ml anhydrous ethanol is added. The reaction mass is continued to be stirred for a period of 3 hours at which time it is determined by GLC analysis (8 feet × ¼ inch SE-30 column) that the reaction mass contains 56.9% desired product. After adding another 0.15 grams of sodium borohydride dissolved in 5 ml anhydrous ethanol with stirring, and stirring the reaction mass for a period of 4 hours at room temperature, it is determined that 73.4% desired product exists.

Figure 27:
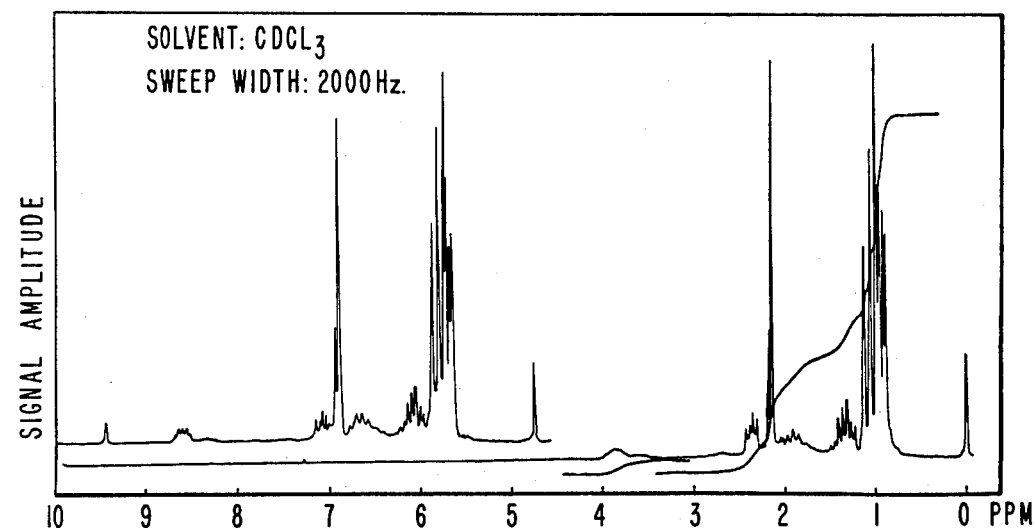
FIG. 27 is the NMR spectrum for the product of Example VI(B) wherein 3-methylthio-2,6-dimethyl-4-heptanol is produced.
Figure 28:
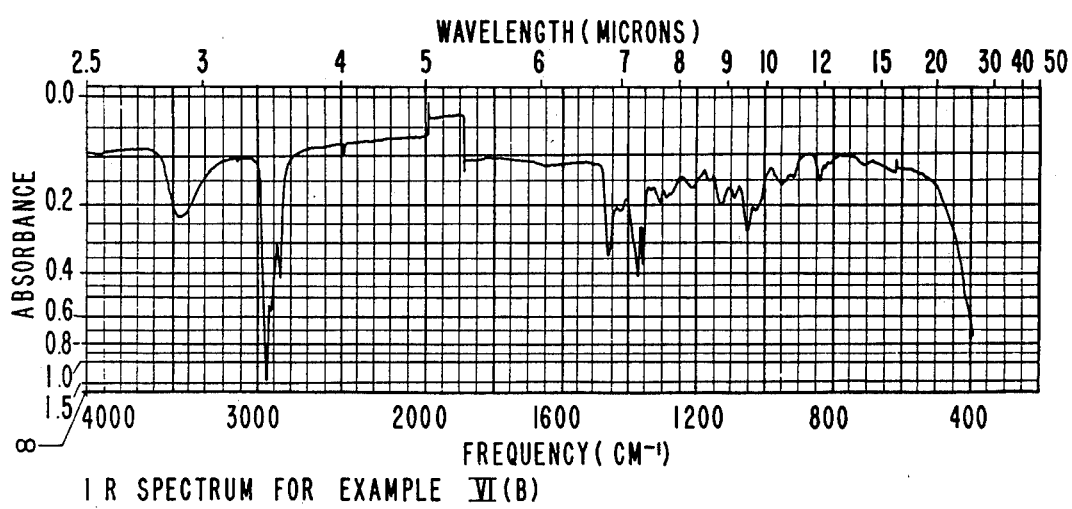
FIG. 28 is the IR spectrum for the product of Example VI(B) wherein 3-methylthio-2,6-dimethyl-4-heptanol is produced.

The reaction mass is then concentrated on a rotary evaporator (using water aspirator vacuum) to a 4 ml volume slurry. Six ml water is added to the resulting slurry and the solid dissolves. The reaction mass now exists in two phases; an aqueous phase and an organic phase. The reaction mass is neutralized with 10% HCl solution to a pH of 5-6. The oil is extracted with two 20 ml portions of methylene chloride. The extracts are washed with water, dried over anhydrous sodium sulfate, gravity filtered and concentrated on a rotary evaporator to a weight of 0.58 grams (pale yellow liquid). GLC, MS, NMR and IR analyses yield the information that the resultant product contains 79.1% 3-methylthio-2,6-dimethyl-4-heptanol. The pure material is trapped out using preparative GLC (Conditions: 8 feet ×¼ inch SE-30 column) and has the structure:

The NMR spectrum is set forth in FIG. 27. The infrared spectrum is set forth in FIG. 28.

The mass spectral analysis is as follows:

| m/e | Relative Intensity |
|---|---|
| 43 | 21 |
| 55 | 55[4] |
| 56 | 25[6] |
| 57 | 35[5] |
| 61 | 19 |
| 69 | 21 |
| 89 | 68[3] |
| 103 | 100[1] |
| 104 | 77[2] |
| M 190 | 19 |

The NMR analysis is as follows:

| 1.12 ppm – 0.90 | methyl protons | 12H |
|---|---|---|
| 1.34 | methine protons | 2H |
| 1.92 | $-CH_2-$ | 2H |
| 2.16 | $CH_3-S-$ | 3H |
| 2.36 | $S-HC-C-O-$ | 1H |
| 3.84 | $HC-O-$ | 1H |

The IR analysis is as follows: 1050 cm⁻¹, 1360, 1385, 1460, 2860, 2920, 2950, 3460.

EXAMPLE VII

PREPARATION OF 3-METHOXY-4-HEPTANONE

Reaction:

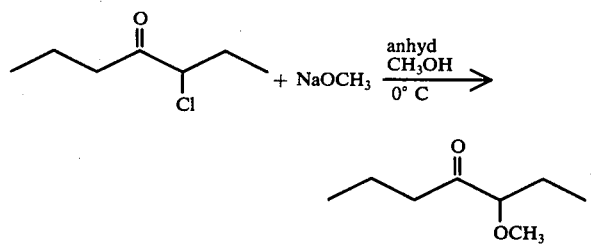

A solution of 1.5 grams of 3-chloro- 4-heptanone in 3 ml anhydrous methanol (0.01 moles 3-chloro-4-heptanone) is placed into a 25 ml, three-necked, round bottom flask equipped with magnetic stirrer, pot thermometer, reflux condenser (with drying tube), 10 ml addition funnel with nitrogen inlet at top an ice water-salt bath, and nitrogen bubbler. The 3-chloro-4-heptanone solution is cooled to a temperature of between 0° and 1° C. Into the 10 ml addition funnel is placed a solution of 0.54 grams of sodium methoxide dissolved in 7 ml anhydrous methanol (0.01 moles sodium methoxide). Over a period of one hour, while maintaining the reaction mass at a temperature of between 0° and 1° C, the sodium methoxide solution to the 3-chloro-4-heptanone. The reaction mass is then permitted to warm up to room temperature. It is then vacuum filtered thereby separating the while precipitate from the filtrate. The white solid precipitate is washed with 25 ml methylene chloride, and the washings are combined with the filtrate prior to concentration. After concentration of the filtrate, the concentrate is dried over anhydrous sodium sulfate and further concentrated to a weight of 1.0 grams (white oil). The major peak is isolated by GLC trapping (8 feet × ¼ inch SE-30 column). NMR, IR and mass spectral analyses confirm that the resulting material has the structure:

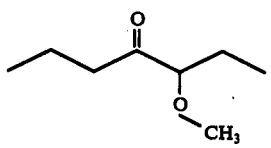

Figure 29:
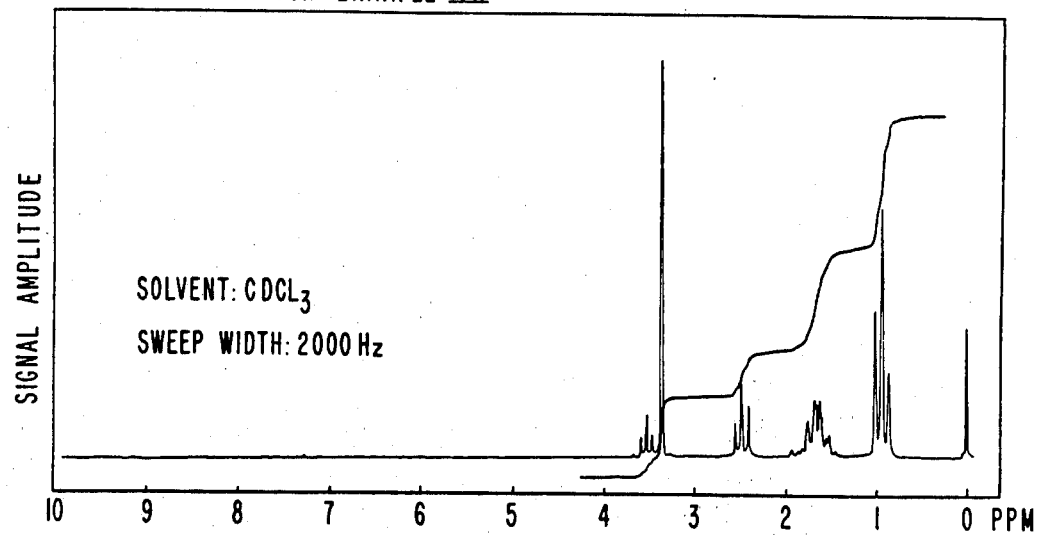
FIG. 29 is the NMR spectrum for the product of Example VII wherein 3-methoxy-4-heptanone is produced.
Figure 30:
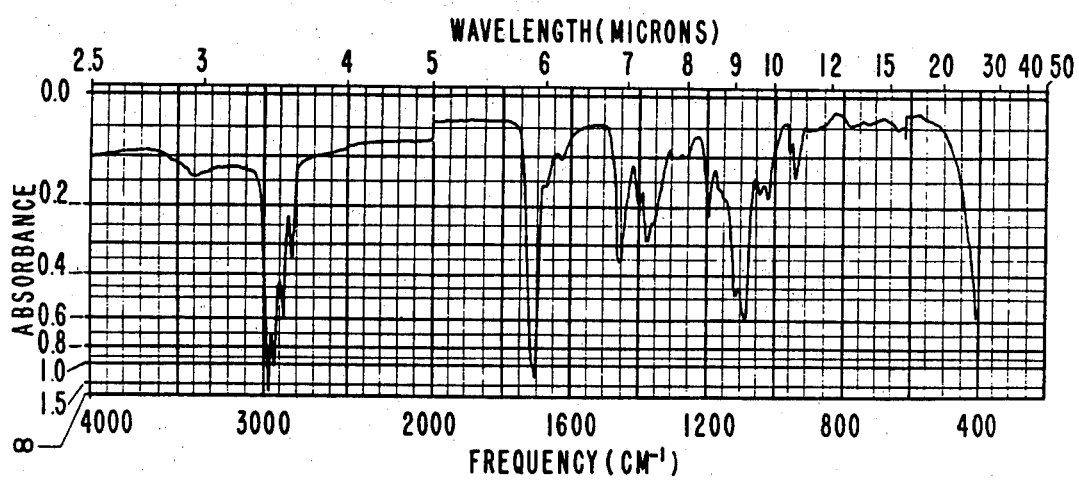
FIG. 30 is the IR spectrum for the product of Example VII wherein 3-methoxy-4-heptanone is produced.

The NMR spectrum is set forth in FIG. 29. The IR spectrum is set forth page in FIG. 30.

The NMR analysis is as follows:

| 0.95 ppm | (t) | $CH_3-$ | 6H |
|---|---|---|---|
| 1.64 | (m) | $-CH_2-$ | 4H |
| 2.49 | (t) | $-CH_2-\overset{\overset{O}{\|\|}}{C}-$ | 2H |
| 3.36 | (s) | $CH_3-O-$ | 3H |
| 3.54 | (t) | $\underset{\|}{\overset{\|}{HC}}-O-$ | 1H |

The infrared analysis is as follows: 1090 cm$^{-1}$, 1120, 1195, 1355, 1375, 1450, 1710, 2820, 2880, 2940, 2960.

EXAMPLE VIII

RASPBERRY FLAVOR FORMULATION

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl Butyrate | 6.0 |
| Ethyl Acetate | 16.0 |
| Dimethyl Sulfide | 1.0 |
| Isobutyl Acetate | 13.0 |
| Acetic Acid | 10.0 |
| Acetaldehyde | 10.0 |
| Propylene Glycol | 930.0 |

3-methoxy-4-heptanone produced according to Example VII is added to half of the above formulation at the rate of 0.2%. The formulation with the 3-methoxy-4-heptanone produced according to Example VII is compared with the formulation without the 3-methoxy-4-heptanone produced according to Example VII at the rate of 0.01 percent (100 ppm) in water and evaluated by a bench panel.

The flavor containing the 3-methoxy-4-heptanone produced according to Example VII is found to have a substantially more pleasant and better raspberry aroma. It is the unanimous opinion of the bench panel that the chemical, 3-methoxy-4-heptanone produced according to Example VII, rounds the flavor out and contributes to a very natural fresh aroma and taste as found in full ripe raspberries. Accordingly, the flavor with the addition of the 3-methoxy-4-heptanone produced according to Example VII is considered as substantially better than the flavor without the 3-methoxy-4-heptanone produced according to Example VII.

EXAMPLE IX

The following formulations are produced:

| Formulation A | | |
|---|---|---|
| 1.9 gm | Natural black currant juice, concentrate | |
| 0.1 gm | Natural black currant esters | |
| 10.0 ml | Sugar Syrup 32° Be | |
| q.s. 100 ml | Spring water | |
| Formulation B | | |
| 1.9 gm | Natural black currant juice, concentrate | |
| 0.1 gm | Buchu leaf oil 0.1% (ethanol 95%) | |
| 10.0 ml | Sugar Syrup 32° Be | |
| q.s. 100 ml | Spring water | |
| Formulation C | | |
| 1.9 gm | Natural black current juice, concentrate | |
| 0.1 gm | Niribine* 10% (ethanol 95%) | |
| 10.0 ml | Sugar Syrup 32° Be | |
| q.s. 100 ml | Spring water | |
| Formulation D | | |
| 1.9 gm | Natural black currant juice, concentrate | |
| 0.1 gm | 3-methylthio-4-heptanone | |
| 10.0 ml | Sugar Syrup 32° Be | |
| q.s. 100 ml | Spring Water | |
| Formulation E | | |
| 1.9 gm | Natural black currant juice, concentrate | |
| 10.0 ml | Sugar Syrup 32° Be | |
| q.s. 100 ml | Spring Water | |

*Niribine is produced by distilling an alcoholic macerate of black currant buds.

Each of the above-mentioned formulations is compared with one another by a panel composed of 10 tasters. Formulation E is generally considered by the panel to be flat and not very characteristic for fresh black current. Formulations B, C and D are considered as having substantially fresh and more pleasant notes than formulation E. In summary, formulation D is preferred as the best black currant flavor, the material 3-methylthio-4-heptanone can be used at rates of one-tenth of that of Buchu leaf oil in black currant juice.

It is further to be concluded that 3-methylthio-4-heptanone can successfully replace Bucchu leaf oil, Niribine and/or natural black currant esters wherever the ingredient is used in reinforced black currant juices, substituted black currant juices and imitation black currant flavors.

EXAMPLE X

BASIC BLACK CURRANT FORMULATION 3-(methallythio)-2,6-dimethyl-4-heptanone produced according to Example II(C) has been added to a basic black currant flavor formulation at the rate of 1.5%. Both flavors have been compared in water at the rate of 200 ppm and evaluated by a bench panel. The flavor containing 3-methallythio-2,6-dimethyl-4-heptanone has had the characteristic aroma and taste of ripe black currants or fresh black currant juice. This typical note was not present in the basic black currant formulation. Therefore all members of the panel preferred the flavor containing 3-(methallylthio)-2,6-dimethyl-4-heptanone. Detailed below is the Basic Black Current Formulation to which is added 3-(methallylthio)-2,6-dimethyl-4-heptanone at the rate of 1.5%.

| Ingredient | Parts by Weight |
|---|---|
| Cis-3-hexen-1-ol | 5 |
| Alpha-phellandrene | 1.5 |
| Terpineol-4 10% (in ethyl alcohol) | 3 |
| Para-hydroxy benzyl acetone | 5 |
| Vanillin | 2 |
| Ethyl maltol | 6 |
| Methyl benzoate | 2 |
| Benzaldehyde | 2 |
| Benzylpropionate | 4 |
| Isobutylacetate | 5 |
| Coriander oil | 0.5 |
| Ethylbutyrate | 8 |
| Dimethylsulfide | 3 |
| Fusel oil | 8 |
| Acetic acid | 10 |
| Alpha-ionone 10% (in ethyl alcohol) | 0.5 |
| Ethyl heptanoate | 0.5 |
| Propylene glycol | 934 |
| | 1000 |

EXAMPLE XI

A. 120 grams of the flavor composition of Example X is emulsified in a solution containing 300 gm gum acacia and 700 gm water. The emulsion is spray-dried with a Bowen Lab Model Drier utilizing 250 c.f.m. of air with an inlet temperature of 500° F, an outlet temperature of 200° F, and a wheel speed of 50,000 r.p.m.

B. The following mixture is prepared:

| Ingredient | Parts by Weight |
|---|---|
| Liquid flavor composition of Example X | 25 |
| Propylene glycol | 1 |
| Cab-O-Sil M-5 (Brand of Silica produced by the Cabot Corporation of 125 High Street, Boston, | 3 |

-continued

| Ingredient | Parts by Weight |
|---|---|
| Mass. 02110; Physical properties: Surface area: 200 m²/gm Nominal Particle size: 0.012 microns Density: 2.3 lbs./cu.ft.) | |
| Ethyl cellulose | 8 |

The Cab-O-Sil and ethyl cellulose is dispersed in the liquid flavor composition of Example X with vigorous stirring, thereby resulting in a viscous liquid. 65 Parts by weight of the powder flavor composition of Part A is then blended into said viscous liquid, with stirring, at 25° C for a period of 30 minutes resulting in a dry, free flowing, sustained release flavor powder.

EXAMPLE XII

CHEWING GUM 100 parts by weight of chicle are mixed with 4 parts by weight of the flavor prepared in accordance with Example XI. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting black current flavor.

EXAMPLE XIII

CHEWABLE VITAMIN TABLETS

The flavor material produced according to Example XI is added to Chewable Vitamin Tablet Formulation at a rate of 5 gm/Kg which Chewable Vitamin Tablet Formulation is prepared as follows:

In a Hobart Mixer, the following materials are blended to homogeneity:

| | Gms/1000 Tablets |
|---|---|
| Vitamin C (ascorbic acid) as ascorbic acid: sodium ascorbate mixture 1:1 | 70.0 |
| Vitamin B$_1$ (thiamine mononitrate) as Rocoat thiamine mononitrate 33 ⅓% (Hoffman La Roche) | 4.0 |
| Vitamin B$_2$ (riboflavin) as Rocoat riboflavin 33 ⅓% | 5.0 |
| Vitamin B$_6$ (pyridoxine hydrochloride) as Rocoat pyridoxine hydrochloride 33 ⅓% | 4.0 |
| Niacinamide as Rocoat niacinamide 33 ⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33 ⅓% Roche | 6.6 |
| d-Biotin | 0.044 |
| Certified lake color | 5.0 |
| Flavor of Example XI | 2.5 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong black currant flavor for a period of 12 minutes.

EXAMPLE XIV 0.5% 3-propylthio-4-heptanone is added to a commercial quality of grapefruit oil. The oils with and without this chemical are compared in water at the rate of 10 ppm. The aroma and taste characteristics of the modified oil is considered as much more characteristic of grapefruit peel than of the oil without this chemical. Therefore, a bench panel unanimously prefers the oil containing 3-propylthio-4-heptanone.

EXAMPLE XV

The following mixture is prepared:

| Ingredients | Parts by Weight |
| --- | --- |
| Methyl anthranilate | 11.0 |
| Ethyl acetate | 9.0 |
| Ethyl anthranilate | 2.5 |
| Ethyl butyrate | 2.0 |
| Ethyl methyl phenyl glycidate | 1.5 |
| Cinnamic alcohol | 0.3 |
| Cognac oil | 0.1 |
| Ethyl alcohol | 73.6 |

The above mixture is judged to be an acceptable grape flavor when evaluated in a sweetened and acidified aqueous tasting solution. 1.5 Parts of 3-methylthio-4-heptanone is added to the above flavor and a significant improvement in aroma and taste is noted. When this is evaluated in the afore-mentioned tasting solution, it is judged to have an improved grape character and grape fidelity. It contains more fresh concord grape character, true fruitness with a nuance of wine. In addition, it is judged to be a more rounded and natural flavor, superior to the product made without the addition of 3-methylthio-4-heptanone in both aroma and taste.

Similar results obtained when using 2.5 parts of 3-methoxy-4-heptanone prepared according to Example VII.

EXAMPLE XVI

BASIC BLACK CURRANT FORMULATION

3-Acetylthio-4-heptanone has been added to a basic black currant flavor formulation at the rate of 1.5%. Both flavors have been compared in water at the rate of 200 ppm and evaluated by a bench panel. The flavor containing 3-acetylthio-4-heptanone has had the characteristic aroma and taste of ripe black currants or fresh black currant juice. This typical note was not present in the basic black currant formulation. Therefore all members of the panel preferred the flavor containing 3-acetylthio-4-heptanone. Detailed below is the Basic Black Currant Formulation to which is added 3-acetylthio-4-heptanone at the rate of 1.5%:

| Ingredient | Parts by Weight |
| --- | --- |
| Cis-3-hexen-1-ol | 5 |
| Alpha-phellandrene | 1.5 |
| Terpineol-4 10% (in ethyl alcohol) | 3 |
| Para-hydroxy benzyl acetone | 5 |
| Vanillin | 2 |
| Ethyl maltol | 6 |
| Methyl benzoate | 2 |
| Benzaldehyde | 2 |
| Benzylpropionate | 4 |
| Isobutylacetate | 5 |
| Coriander oil | 0.5 |
| Ethylbutyrate | 8 |
| Dimethylsulfide | 3 |
| Fusel oil | 8 |
| Acetic acid | 10 |
| Alpha-ionone 10% (in ethyl alcohol) | 0.5 |
| Ethyl heptanoate | 0.5 |
| Propylene glycol | 934 |
| | 1000 |

EXAMPLE XVII

GRAPEFRUIT FLAVOR

The following formulation is prepared:

| Ingredients | Parts by Weight |
| --- | --- |
| Grapefruit oil | 92 |
| Bergamot oil | 2 |
| Citral | 3 |
| Amyl alcohol | 1 |
| Ethyl acetate | 1 |
| (1,3-diethylacetonyl)(1,3-diisopropylacetonyl) sulfide | 1 |

When the above grapefruit formulation is added to water at the rate of 1%, an excellent grapefruit drink is prepared. The (1,3-diethylacetonyl) (1,3-diisopropylacetonyl)sulfide gives a fruitier peeliness to the instant formulation thereby rendering it more desirable. The effect rendered by the (1,3-diethylacetonyl) (1,3-diisopropylacetonyl)sulfide can also be rendered by using 0.5 parts of 3-methylthio-4-heptanone or 3-propylthio-4-heptanone or 3-(methallylthio)-2,6-dimethyl-4-heptanone or 3-crotylthio-2,6-dimethyl-4-heptanone or 3-allylthio-2,6-dimethyl-4-heptanone.

EXAMPLE XVIII

3-Propylthio-4-heptanol is added to a commercial instant tomato soup mix (Tomatancreme Suppe, C. H. Knorr, Heilbrown, West Germany) at the rate of 2 ppm (based on the weight of the soup as ready to eat, produced by adding 80 g. of the dry soup mix to 1,000 ml water and then bringing the resulting mixture to a boil). A second control is prepared which is identical to the initial sample except for the absence of the 3-propylthio-4-heptanol. A four member panel of flavorists compared the control to the soup containing 3-propylthio-4-heptanol. All four members of the panel indicated a strong preference for the tomato soup containing the 3-propylthio-4-heptanol. All four members of the panel indicated that the soup containing the 3-propylthio-4-heptanol includes a fresh tomato note which is not present in the soup prepared without using the 3-propylthio-4-heptanol.

EXAMPLE XIX

1-Propylthio-1,3-diphenyl-2-propanone is dissolved in 95% ethanol to provide a 2% solution, and is held at room temperature for 24 hours. It is then diluted with water to 0.1% and this solution has an aroma of fresh green onions.

Various water solutions are prepared, as shown in the following Table II and evaluated for taste:

TABLE II

| Concentration (ppm) | Evaluation |
| --- | --- |
| 0.002 | Green onion character; near threshold level |
| 0.010 | Fresh green onion taste |

The material is added to a chicken broth to obtain a concentration of 0.010 ppm, and it is found that the chicken taste is deepened and that a light onion aftertaste is added. Increasing the concentration to 0.030 ppm adds an onion aroma, and the fresh onion taste is dominating.

Repetition of the foregoing with beef broth shows no significant difference at 0.010 ppm; a slightly lachrymatory aroma and an improved general taste at 0.030 ppm; and a dominating onion note with the beef broth changed to onion soup at 0.2 ppm.

It is judged that this flavor additive can replace all flavor areas where fresh onion is used, and it is interesting enough to be used alone to develop onion soup flavor characteristic.

EXAMPLE XX

Three meat-loaf type products are prepared according to the following formulation:

| Ingredient | Amount |
| --- | --- |
| TVP, minced | 1 cup |
| Ground beef | 1 cup |
| Water | 1 cup |
| Beef suet | ¼ cup |
| Bread crumbs, dry, unflavored | 1 cup |
| Whole milk | 1 cup |
| Egg albumen | 3 tbsp. |
| Salt | 1 ¼ tbsp. |
| Black pepper | ¼ tsp. |
| Catsup | ¼ cup |
| Water | 32 ml. |

The TVP is a texturized vegetable protein mixture made by Archer-Daniels-Midland Company.

Three separate portions prepared according to the foregoing formulation are made into three meat loaves. Loaf A contains no additional additive, Loaf B contains 32 ml of fresh pressed onion juice to replace the 32 ml of water, and Loaf C contains 0.6 ppm of 1-propylthio-1,3-diphenyl-2-propanone.

The three loaves are baked at 350° F for one hour and evaluated for flavor by a panel of twelve judges. The consensus of the judges is that Loaves B and C are superior to Loaf A because the onion character of B and C enhances the overall taste and covers the dry, cardboard-like cereal character of Loaf A. It is accordingly apparent that the product of this invention is a valuable ingredient for a wide variety of flavors and types of foodstuffs.

EXAMPLE XXI

A white bread dough mix is prepared by mixing 1350 g wheat flour and 800 ml water. To the mix is added:

| Ingredient | Amount (grams) |
| --- | --- |
| Yeast | 27.0 |
| Sodium chloride | 27.0 |
| Sucrose | 67.5 |
| Shortening | 54 |
| Non-fat dry milk powder | 40.5 |
| Yeast food (Arkady; Manufactured by Fleischmann, Div. of Standard Brands) | 0.50 |
| Softening agent (succinylated monoglycerides; Manufactured by Kraft Div. of National Diary Products Corporation) | 3.4 |

The dough is then mixed for 8 minutes, 3-[(methoxycarbonyl)methylthio]-4-heptanone (8 grams) is then mixed with the resulting product for a period of 8 minutes. The dough is then allowed to rise for 45 minutes at 40° C. The dough is then baked for 45 minutes at 210° C.

The breadstuff product obtained has a flavor note reminiscent of the crust of home made Italian bread and has acceptable and persistent flavor properties for a period of one week and has good flavor characteristics when spread with margarine.

By way of comparison, breadstuffs similarly prepared by omitting the sulfur-free amino acid-cyclic ketone reaction product and the 3-[(methoxycarbonyl)methylthio]-4-heptanone have a flat taste, show typical flavor deterioration on storage during a period of one week and require an expensive butter spread to provide an acceptable flavor.

EXAMPLE XXII

A. PREPARATION OF 3-ISOBUTYLTHIO-2,6-DIMETHYL-4-HEPTANONE

Reaction:

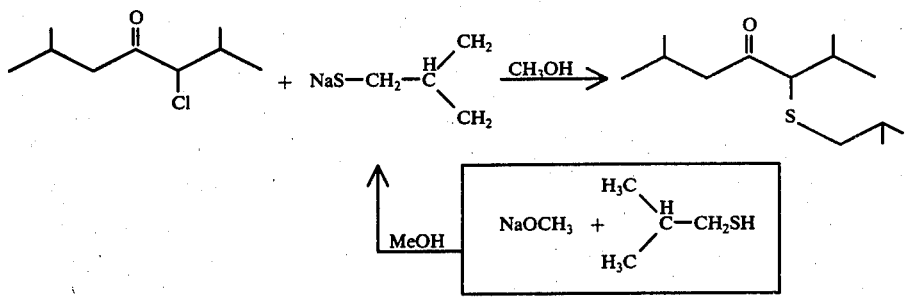

Into a 50 ml, three-necked, round bottom flask equipped with pot thermometer, magnetic stirrer, gas inlet tube (for nitrogen) at top of 15 cm Vigreux column, nitrogen bubbler and cold water bath is added a solution of 0.54 grams (0.01 moles) of sodium methoxide dissolved in 6 ml anhydrous methanol. The solution is cooled to 24° C and a solution of 0.90 grams (0.01 moles) of isobutyl mercaptan dissolved in 6 ml anhydrous methanol is then added to the reaction mass. After stirring at 24° C for a period of 10 minutes, a solution of 1.77 grams of 3-chloro-2,6-dimethyl-4-heptanone dissolved in 2 ml anhydrous methanol is added to the reaction mass with stirring at 24° C–25° C. The reaction mass is then stirred for a period of 8 hours.

The reaction mass is then concentrated on a rotary evaporator using water aspirator vacuum to 5 ml of a thick oil/solid slurry. 15 ml water is added and the solid dissolves. The resulting liquid mixture being in 2 phases;

an aqueous phase and an organic phase. The reaction mass is then extracted with three 10 ml of methylene dichloride and the extracts are combined and washed with 8 ml water. The extracts are then dried over anhydrous sodium sulfate, gravity filtered and concentrated on a rotary evaporator to a weight of 1.89 grams (pale yellow oil). GLC, NMR, IR and mass spectral analyses yield the information that the resulting product is 79.2% 3-isobutylthio-2,6-dimethyl-4-heptanone.

The NMR analysis is as follows:

| 0.94 ppm, 1.10 | methyl protons | 18 H |
|---|---|---|
| 2.26-1.60 | methine protons | 3 H |
| 2.26 | —CH$_2$—S— | 2 H |
| 2.50 | $\begin{array}{c}O\\\|\|\\-CH_2-C-\end{array}$ | 2 H |
| 2.80 | $\begin{array}{c}HC-S\\\|\\-C=O\end{array}$ | 1 H |

The IR analysis is as follows:
1035 cm$^{-1}$, 1160, 1285, 1360, 1380, 1460, 1700, 2870, 2930, 2960.

The mass spectral analysis is as follows:

| m/e | Relative Intensity |
|---|---|
| 29 | 7 |
| 41 | 11$^5$ |
| 55 | 17$^4$ |
| 57 | 42$^2$ |
| 69 | 6 |
| 85 | 8 |
| 89 | 33$^3$ |
| 145 | 100$^1$ |
| 146 | 9$^6$ |
| M 230 | 8 |

Figure 30A:
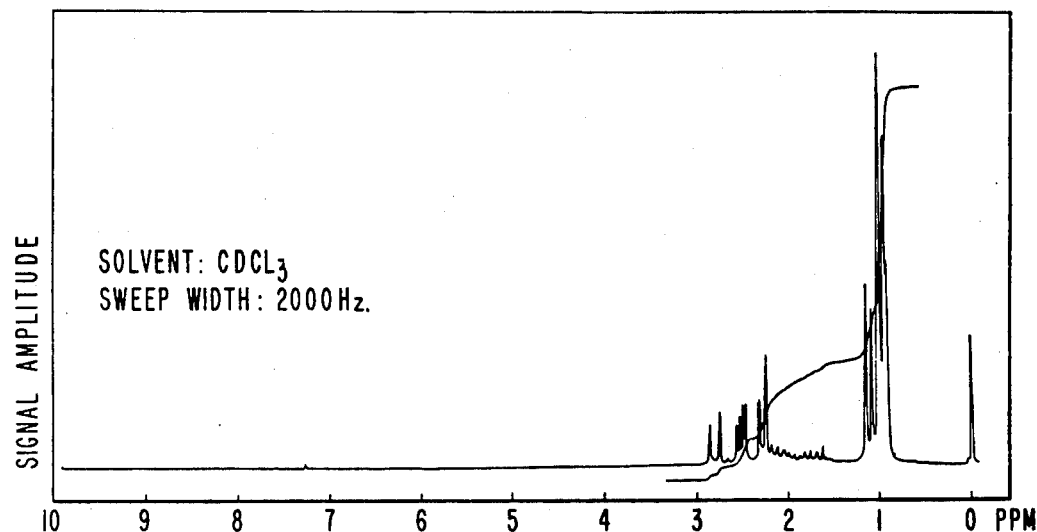
FIG. 30(A) is the NMR spectrum for the product of Example XXII(A) wherein 3-isobutylthio-2,6-dimethyl-4-heptanone is produced.
Figure 30B:
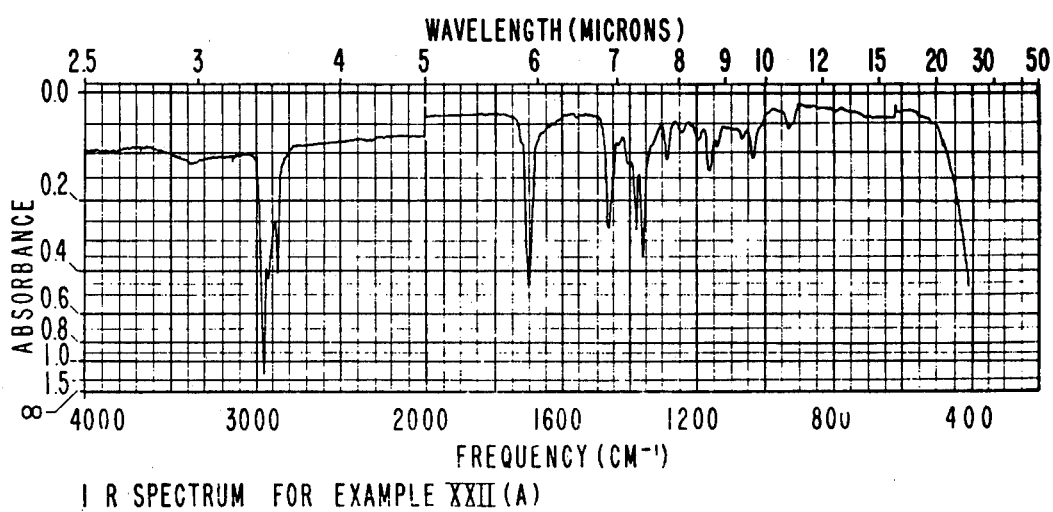
FIG. 30(B) is the IR spectrum for the product of Example XXII(A) wherein 3-isobutylthio-2,6-dimethyl-4-heptanone is produced.

The NMR spectrum is set forth in FIG. 30(A). The IR spectrum is set forth in FIG. 30(B).

B. PREPARATION OF 3-ISOBUTYLTHIO-2,6-DIMETHYL-4-HEPTANOL

Reaction:

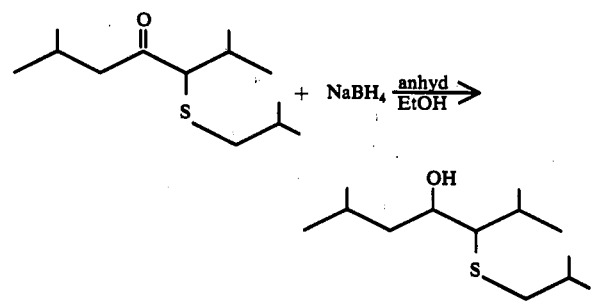

Into a 25 ml, three-necked, round bottom flask equipped with magnetic stirrer, reflux condenser, pot thermometer and nitrogen inlet tube to flush with dry nitrogen, is added a solution of 0.1 grams (0.00265 moles) of sodium borohydride dissolved in 4 ml anhydrous ethanol. While the temperature of the sodium borohydride solution is at 24° C, a solution of 1.1 grams of 3-isobutylthio-2,6-dimethyl-4-heptanone (prepared according to Part A) dissolved in 4 ml anhydrous ethanol is added to the reaction mass slowly. The reaction mass is then stirred for a period of 6.5 hours.

The reaction then shows 30% product (3-isobutylthio-2,6-dimethyl-4-heptanol) by GLC analysis. An additional 0.2 grams of sodium borohydride dissolved in 6 ml anhydrous ethanol is added, and the reaction mass is continued to be stirred for a period of 4 hours. GLC analysis shows 59% product. Another 0.15 grams of sodium borohydride in 5 ml anhydrous ethanol is added and stirred for an additional 4 hours. GLC analysis then shows 78% product.

The reaction mixture is then concentrated on a rotary evaporator using water aspirator vacuum to 5 ml of an oily solid. 6 ml water is then added and the solid dissolves yielding two liquid phases; an organic phase and an aqueous phase. The reaction mass is neutralized with 10% HCl to a pH of 5. The oil is then extracted with 20 ml methylene dichloride, and the extracts are washed with water. The extracts are then dried over anhydrous sodium sulfate, filtered and concentrated on a rotary evaporator to a weight of 0.82 grams (pale yellow oil). GLC analysis indicates that the material is 86.4% product. NMR and IR analyses of GLC trapped compound yield the information that the product is 3-isobutylthio-2,6-dimethyl-4-heptanol.

Figure 31:
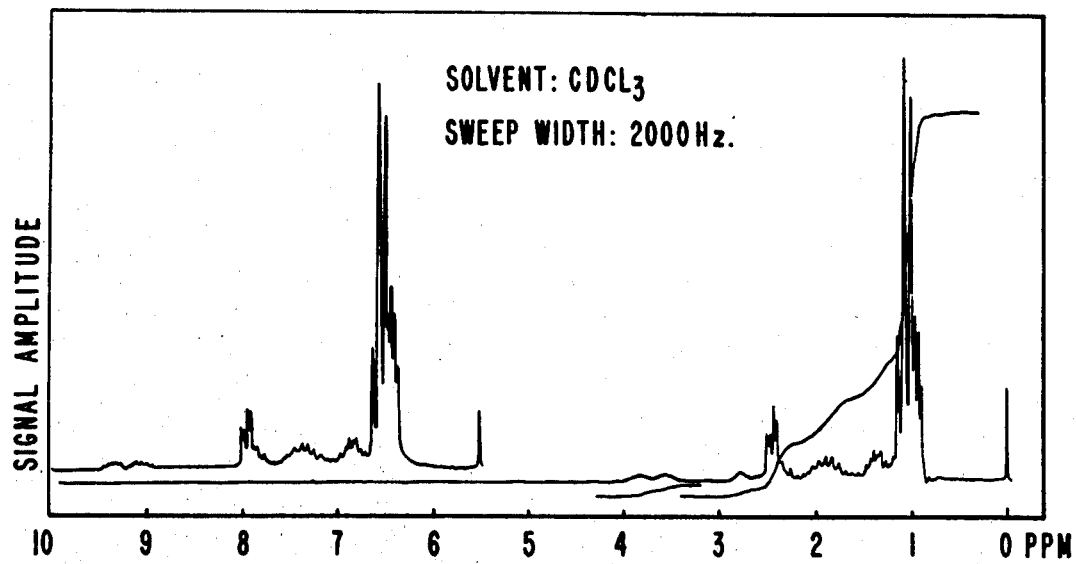
FIG. 31 is the NMR spectrum for the product of Example XXII(B) wherein 3-isobutylthio-2,6-dimethyl-4-heptanol is produced.
Figure 32:
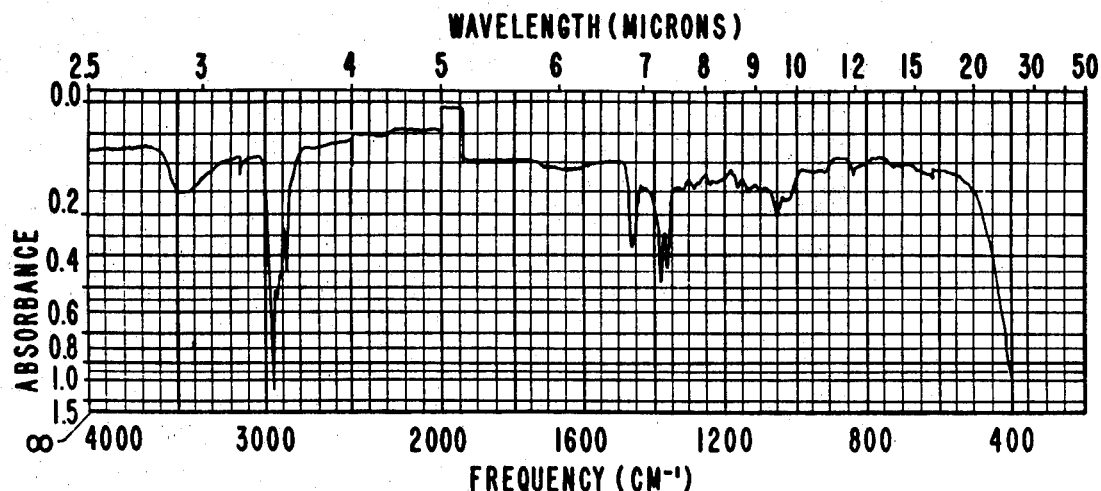
FIG. 32 is the IR spectrum for the product of Example XXII(B) wherein 3-isobutylthio-2,6-dimethyl-4-heptanol is produced.

The NMR spectrum is set forth in FIG. 31. The IR spectrum is set forth in FIG. 32.

The NMR analysis is as follows:

| 1.10-0.89 ppm | superimposed signals | CH$_3$— | 18H |
|---|---|---|---|
| 1.34 | (m) | methine protons | 3H |
| 1.84 | (m) | —CH$_2$—C—O— | 2H |
| 2.44 | (m) | —CH$_2$—S—, HC—S— | 3H |
| 2.79 | (broad) | —OH | 1H |
| 3.72 | (m) | $\begin{array}{c}\|\\HC-OH\\\|\\H\end{array}$ | |

The IR analysis is as follows:
1055 cm$^{-1}$, 1365, 1385, 1465, 2880, 2930, 2960, 3460.

EXAMPLE XXIII

OTTO OF ROSE PERFUME FORMULATION

The following mixture is prepared:

| Ingredients | Parts by Weight |
|---|---|
| Phenyl acetic acid | 5 |
| Hydroxycitronellal | 10 |
| Geraniol | 125 |
| Citronellol | 150 |
| Phenyl ethyl alcohol | 50 |
| Phenyl ethyl acetate | 4 |
| Ethyl phenyl acetate | 5 |
| Citronellyl formate | 20 |
| Geranyl acetate | 25 |
| Linalool | 15 |
| Terpineol | 10 |
| Eugenol | 3 |
| Phenyl acetaldehyde dimethyl acetal | 5 |
| Benzyl acetate | 3 |
| Guaiacwood Oil | 5 |
| 3-methylthio-4-heptanone produced according to the process of Part "C" of Example I | 10 |

The 3-methylthio-4-heptanone, produced according to the process of Part C of Example I imparts a green, fruity, spicy, topnote so characteristic of rose otto to this formulation.

EXAMPLE XXIV

ORIENTAL VETIVERT

The following mixture is prepared:

| Ingredients | Parts by Weight |
|---|---|
| Orange oil Florida | 150 |
| Lemon Oil | 75 |
| Oil of bitter orange | 100 |
| Grapefruit oil | 200 |
| Neroli oil | 20 |
| Isocyclemone E (a product produced according to the process of Example VI of U.S. Patent 3,907,321, issued on Sept. 23, 1975, which comprises reacting myrcene with 3-methyl-3-pentene-2-one in the presence of aluminum chloride and then cyclizing the resulting Diels-Alder adduct.) | 40 |
| Gamma methyl ionone | 15 |
| Ylang estra | 5 |
| Auralva (The Shiff base of methyl anthranilate and hydroxy citronellal, specifically described in Section 1735 of Arctancer, "Perfume and Flavor Chemicals (Aroma Chemicals)" 1969) | 15 |
| Lyral 4-(4-methyl,4-hydroxyamyl) Δ³— cyclohexene carboxaldehyde | 30 |
| Grisalva (produced by the 50% sulfuric acid treatment of 3-ethyl-1[2,2,6-trimethyl-cyclohexene-5-yl-1]hexen-3-ol-6) | 10 |
| 3-(methallylthio)-2,6-dimethyl-4-heptanone, produced according to the process of Example II(C). | 50 |

The 3-(methallylthio)-2,6-dimethyl-4-heptanone, produced according to the process of Example II(C) imparts a sweet, orange-flower, green beta vetivone, woody character to this composition.

EXAMPLE XXV

NARCISSE FORMULATION

The following mixture is prepared:

| Ingredient | Parts by Weight |
|---|---|
| Benzyl alcohol | 50 |
| Benzyl benzoate | 25 |
| Terpineol | 30 |
| Nerol | 15 |
| Phenyl ethyl alcohol | 50 |
| Geraniol | 40 |
| Linalool | 50 |
| Para cresyl phenyl acetate | 10 |
| Benzyl acetate | 6 |
| Acetyl isoeugenol | 20 |
| Heliotropin | 30 |
| Ylang extra | 5 |
| Para cresol | 1 |
| 3-methylthio-4-heptanol, produced according to the process of Example I, Part "D" | 20 |

The 3-methylthio-4-heptanol, produced according to the process of Example I, Part D imparts a green, floral, tobacco-like oriental middle and undertone necessary for narcisse.

EXAMPLE XXVI

COMPARISON OF SUBSTITUTED THIOHEPTANONES AND THEIR CORRESPONDING ALCOHOLS 3-methylthio-4-heptanone (hereinafter referred to as "chemical I") has a powerful green, minty, herbaceous odor.

3-methylthio-4-heptanol (hereinafter referred to as "chemical II") has a green, floral, herbal odor, about one-fifth the strength of chemical I.

3(methallylthio)2,6-dimethyl-4-heptanone (hereinafter referred to as "chemical III") has a floral, herbaceous aroma with a fruity, grapefruit (nootkatone) character.

The foregoing materials, chemicals I, II, and III may be used in perfumery to give unusual and novel effects to various fragrance types. They are useful in creating modern blends which are in some cases far removed from the classical concepts of perfumery. The use of chemicals I, II and III may be demonstrated in the following modern herbal formulation:

| Ingredients | A | B | C |
|---|---|---|---|
| Oakmoss Absolute 50% in diethylphthalate | 20 | 20 | 20 |
| α-methyl-3,4-methylene-dioxy-hydrocinnamic aldehyde | 10 | 10 | 10 |
| methyl dihydrojasmonate (produced by Firmenich et Cie of Geneva, Switzerland) | 100 | 100 | 100 |
| Coumarin | 20 | 20 | 20 |
| Musk Ketone | 80 | 80 | 80 |
| Isocyclocitral (10% in diethylphthalate) | 10 | 10 | 10 |
| Galbanum Oil (10% in diethylphthalate) | 6 | 6 | 6 |
| Rosemary Oil | 10 | 10 | 10 |
| Pine Needle Oil | 60 | 60 | 60 |
| Fir Balsam Absolute (10% in diethylphthalate) | 10 | 10 | 10 |
| Bergamot Oil | 60 | 60 | 60 |
| Lemon Oil | 14 | 14 | 14 |
| Benzyl Acetate | 468 | 460 | 460 |
| Linalool | 80 | 80 | 80 |
| Indol (10% in diethylphthalate) | 6 | 6 | 6 |
| Undecalactone (10% in diethylphthalate) | 12 | 12 | 12 |
| Ylang Ylang Oil | 32 | 32 | 32 |
| Alkylthio chemical I | 2 | — | — |
| Alkylthio chemical II | — | 10 | — |
| Alkylthio chemical III | — | — | 10 |

The addition of 0.2% by weight of chemical I gives increased strength to the fragrance as well as modifying the herbal character and rendering it unusual and novel.

The material can be used in perfumery at from approximately 1 ppm (0.0001%) up to approximately 1%.

The weaker alcohol, chemical II, is added to the fragrance at 1% by weight. The addition of this material gives a softer but alters the herbal effect to an unusual and novel character. Chemical II may be used in perfumery from approximately 0.01% to 5% by weight. For special effects up to 50% may be used.

The addition of 1% of chemical III gives guite a different effect. In this case the herbal character is not altered as in the other examples, but the citrus notes the enhanced and strengthened. This chemical may be used in perfumery from approximately 0.01% to 10% by weight. For special effects up to 50% may be used.

In all cases of the above examples, the fragrance is improved by the addition of the alkylthio materials chemicals I, II and III and rendered more desirable and novel.

EXAMPLE XXVII

PREPARATION OF SOAP COMPOSITIONS 100 grams of soap chips are mixed with 1 gram of the chemical set forth in Table II below until a substantially homogeneous composition is obtained. The perfumed soap composition manifests an aroma according to the aroma set forth in Table II below:

| Compound | Aroma |
|---|---|
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oil-like aroma. |
| 3-isobutylthio-4-heptanone | A green, spicey and peppery aroma with an underlying bergamot note. |
| 3-isobutylthio-2,6-dimethyl-4-heptanol | A green aroma containing notes of hyacinth and narcisse. |
| 3-methylthio-2,6-dimethyl-4-heptanone | A sweet, slightly floral and woody aroma with fruity and berry nuances. |
| 3-(methallylthio)-2,6-dimethyl-4-heptanone | A fruity, grapefruit, somewhat floral aroma with underlying yara and neroli notes and bready, vegetative nuances. |

EXAMPLE XXVIII

PREPARATION OF A DETERGENT COMPOSITION

A total of 100 grams of a detergent powder (a nonionic detergent powder containing a proteolytic enzyme prepared according to Example I of Canadian Pat. No. 985,190 issued on Mar. 9, 1976) is mixed with 0.15 grams of the α-oxy(oxo) sulfides set forth in Table III below until a substantially homogeneous composition is obtained. This composition has an excellent aroma as defined in Table III below:

| Compound | Aroma |
|---|---|
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oil-like aroma. |
| 3-isobutylthio-4-heptanone | A green, spicey and peppery aroma with an underlying bergamot note. |
| 3-isobutylthio-2,6-dimethyl-4-heptanol | A green aroma containing notes of hyacinth and narcisse. |
| 3-methylthio-2,6-dimethyl-4-heptanone | A sweet, slightly floral and woody aroma with fruity and berry nuances. |
| 3-(methallylthio)-2,6-dimethyl-4-heptanone | A fruity, grapefruit, somewhat floral aroma with underlying yara and neroli notes and bready, vegetative nuances. |

EXAMPLE XXIX

PREPARATION OF COSMETIC POWDER COMPOSITIONS

Cosmetic powders are prepared by mixing in a ball mill 100 grams of talcum powder with 0.25 grams of each of the compounds set forth in Table IV below. Each of these powders has an excellent aroma as set forth in Table IV below.

Table IV

| Compound | Aroma |
|---|---|
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oil-like aroma. |
| 3-isobutylthio-4-heptanone | A green, spicey and peppery aroma with an underlying bergamot note. |
| 3-isobutylthio-2,6-dimethyl-4-heptanol | A green aroma containing notes of hyacinth and narcisse. |
| 3-methylthio-2,6-dimethyl-4-heptanone | A sweet, slightly floral and woody aroma with fruity and berry nuances. |
| 3-(methyllylthio)-2,6-dimethyl-4-heptanone | A fruity, grapefruit, somewhat fluoral aroma with underlying yara and neroli notes and bready, vegetative nuances. |

EXAMPLE XXX

PERFUMED LIQUID DETERGENT

Concentrated liquid detergents with rich, pleasant aromas as set forth in Table V below are prepared containing 0.10%, 0.15% and 0.20% of an α-oxy(oxo) sulfide as set forth in Table V below. They are prepared by adding and homogeneously admixing the appropriate quantity of α-oxy(oxo) sulfide in the liquid detergent. The liquid detergents are all produced using anionic detergents containing a 50:50 mixture of sodium lauroyl sarcosinate and potassium N-methyl lauroyl tauride. The detergents all possess a pleasant fragrance as defined in the table below, the intensity increasing with greater concentration of α-oxy(oxo) sulfide of this invention.

| Compound | Aroma |
|---|---|
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oil-like aroma. |
| 3-isobutylthio-4-heptanone | A green, spicey and peppery aroma with an underlying bergamot note. |
| 3-isobutylthio-2,6-dimethyl-4-heptanol | A green aroma containing notes of hyacinth and narcisse. |
| 3-methylthio-2,6-dimethyl- | A sweet, slightly floral and |

-continued

| Compound | Aroma |
|---|---|
| 4-heptanone | woody aroma with fruity and berry nuances. |
| 3-(methallylthio)-2,6-dimethyl-4-heptanone | A fruity, grapefruit, somewhat floral aroma with underlying yara and neroli notes and bready, vegetative nuances. |

EXAMPLE XXXI

An α-oxy(oxo) sulfide as set forth in Table VI below is incorporated in a cologne at a concentration of 2.5% in 85% aqueous ethanol; and into a handkerchief perfume at a concentration of 20% (in 95% aqueous ethanol). A distinct and definite strong fragrance as set forth in Table VI below is imparted to the cologne and to the handerchief perfume:

| Compound | Aroma |
|---|---|
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oil-like aroma. |
| 3-isobutylthio-4-heptanone | A green, spicey and peppery aroma with an underlying bergamot note |
| 3-isobutylthio-2,6-dimethyl-4-heptanol | A green aroma containing notes of hyacinth and narcisse. |
| 3-methylthio-2,6-dimethyl-4-heptanone | A sweet, slightly floral and woody aroma with fruity and berry nuances. |
| 3-(methallylthio)-2,6-dimethyl-4-heptanone | A fruity, grapefruit, somewhat floral aroma with underlying yara and neroli notes and bready, vegetative nuances. |

What is claimed is:

1. An alpha oxo sulfide or oxo ether having the structure:

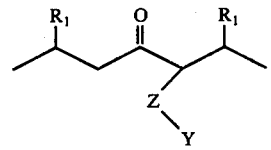

wherein Z is one of sulfur or oxygen; wherein $R_1$ is methyl or hydrogen; and Y is one of $C_1$-$C_4$ alkyl, $C_3$ or $C_4$ alkenyl, or 1,3-diethylacetonyl.

2. The compound of claim 1 wherein Y is methyl, Z is oxygen, and $R_1$ is hydrogen.

3. The compound of claim 1 wherein $R_1$ is methyl, Y is 1,3-diethylacetonyl, and Z is sulfur.

4. The compound of claim 1 wherein Y is methyl, $R_1$ is hydrogen, and Z is sulfur.

5. The compound of claim 1 wherein $R_1$ is hydrogen, Y is 2-methyl-1-propyl, and Z is sulfur.

6. The compound of claim 1 wherein $R_1$ is hydrogen, Y is n-propyl, and Z is sulfur.

7. The compound of claim 1 wherein $R_1$ is methyl, Y is methallyl, and Z is sulfur.

8. The compound of claim 1 wherein $R_1$ is methyl, Y is crotyl, and Z is sulfur.

9. The compound of claim 1 wherein $R_1$ is methyl, Y is allyl, and Z is sulfur.

* * * * *

UNITED STATES PATENT AND TRADEMARK OFFICE
CERTIFICATE OF CORRECTION

PATENT NO. : 4,045,491

DATED : August 30, 1977

INVENTOR(S) : William J. Evers; Howard H. Heinsohn, Jr.

It is certified that error appears in the above-identified patent and that said Letters Patent are hereby corrected as shown below:

Column 3, Line 12: "flack" should read --- black ---

Column 5, Lines 43-47: Left margin obscured; first words should be:
--- Furthermore
prior
indicated
type
ing Column 7, Line 5: "alliaceaus" should read --- alliaceous ---

Column 10, Table I: Flavor property of second compound, first word "Viole" should read --- Violet ---

Column 12, Table I: Flavor property of third compound, first line, "citronelleal" should read --- citronellal ---

Column 14, Table II Aroma property of first compound, last line, "vetetative" should read --- vegetative ---

Column 14, Table II Aroma property, sixth compound from top, third line, "vetetable" should read --- vegetable ---

Column 15, Line 2: "aliaceous" should read --- alliaceous ---

Column 15, Line 48: "litle" should read --- little ---

Column 17, Line 39: "etyl butyrate" should read --- ethyl butyrate ---

Column 22, Line 42: "thens" should read --- then ---

UNITED STATES PATENT AND TRADEMARK OFFICE
CERTIFICATE OF CORRECTION

PATENT NO. : 4,045,491
DATED : August 30, 1977
INVENTOR(S) : William J. Evers; Howard H. Heinsohn, Jr.

It is certified that error appears in the above-identified patent and that said Letters Patent are hereby corrected as shown below:

Column 23, Line 61: "Pat A" should read --- Part A ---

Column 28, Line 56: "anhdyrous" should read --- anhydrous ---

Column 28, Line 60: "MNR" should read --- NMR ---

Column 36, Line 34: "yellwo" should read --- yellow ---

Column 47, Line 34: "while" should read --- white ---

Signed and Sealed this

Eighteenth Day of April 1978

[SEAL]

Attest:

RUTH C. MASON
Attesting Officer

LUTRELLE F. PARKER
Acting Commissioner of Patents and Trademarks